(12) United States Patent
MacLean et al.

(10) Patent No.: US 12,329,158 B2
(45) Date of Patent: *Jun. 17, 2025

(54) LARGE-SCALE METHODS OF UNIFORMLY COATING PACKAGING SURFACES WITH A VOLATILE ANTIMICROBIAL TO PRESERVE FOOD FRESHNESS

(71) Applicant: AGROFRESH INC., Philadelphia, PA (US)

(72) Inventors: Daniel MacLean, Woodland, CA (US); Richard M. Jacobson, Chalfont, PA (US); Timothy Malefyt, Stroudsburg, PA (US)

(73) Assignee: AGROFRESH INC., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/373,376

(22) Filed: Sep. 27, 2023

(65) Prior Publication Data

US 2024/0049714 A1 Feb. 15, 2024

Related U.S. Application Data

(60) Continuation of application No. 17/346,446, filed on Jun. 14, 2021, now Pat. No. 11,771,089, which is a continuation of application No. 16/707,516, filed on Dec. 9, 2019, now Pat. No. 11,039,617, which is a continuation-in-part of application No. 16/123,735, filed on Sep. 6, 2018, now Pat. No. 10,765,117, which is a continuation of application No. 15/445,247, filed on Feb. 28, 2017, now Pat. No. 10,070,649, which is a continuation-in-part of application No. 14/690,929, filed on Apr. 20, 2015, now Pat. No. 9,585,396, which is a continuation-in-part of application No. 14/294,057, filed on Jun. 2, 2014, now Pat. No. 9,426,996, which is a continuation of application No. 14/167,093, filed on Jan. 29, 2014, now Pat. No. 9,138,001, said application No. 14/690,929 is a continuation-in-part of application No. 14/182,793, filed on Feb. 18, 2014, now Pat. No. 9,138,002, which is a division of application No. 13/945,577, filed on Jul. 18, 2013, now Pat. No. 8,669,207, said application No. 16/707,516 is a continuation-in-part of application No. 15/485,500, filed on Apr. 12, 2017, now abandoned.

(60) Provisional application No. 61/991,821, filed on May 12, 2014, provisional application No. 61/758,313, filed on Jan. 30, 2013, provisional application No. 61/831,187, filed on Jun. 5, 2013, provisional application No. 62/323,247, filed on Apr. 15, 2016.

(51) Int. Cl.
| | | |
|---|---|---|
| *A01N 55/08* | (2006.01) | |
| *A01N 25/18* | (2006.01) | |
| *A01N 55/00* | (2006.01) | |
| *A23B 2/721* | (2025.01) | |
| *A23B 4/16* | (2006.01) | |
| *A23B 4/20* | (2006.01) | |
| *A23B 7/152* | (2006.01) | |
| *A23B 7/154* | (2006.01) | |
| *A61K 9/00* | (2006.01) | |
| *A61K 9/70* | (2006.01) | |
| *A61K 31/69* | (2006.01) | |

(52) U.S. Cl.
CPC ............. *A01N 55/08* (2013.01); *A01N 25/18* (2013.01); *A01N 55/00* (2013.01); *A23B 2/721* (2025.01); *A23B 4/16* (2013.01); *A23B 4/20* (2013.01); *A23B 7/152* (2013.01); *A23B 7/154* (2013.01); *A61K 9/0034* (2013.01); *A61K 9/70* (2013.01); *A61K 31/69* (2013.01)

(58) Field of Classification Search
CPC ...................................... A01N 55/08
USPC .......................................... 514/64
See application file for complete search history.

(56) References Cited

U.S. PATENT DOCUMENTS

| | | | |
|---|---|---|---|
| 3,686,398 | A | 8/1972 | Mcmurtry et al. |
| 3,873,279 | A | 3/1975 | Singer |
| 4,421,774 | A | 12/1983 | Vidal et al. |
| 4,843,956 | A | 7/1989 | Lashlee |
| 5,880,188 | A | 3/1999 | Austin et al. |
| 5,958,463 | A | 9/1999 | Milne et al. |
| 6,305,148 | B1 | 10/2001 | Bowden et al. |
| 7,078,546 | B2 | 7/2006 | Piers et al. |
| 7,119,049 | B2 | 10/2006 | Rieck et al. |
| 7,176,228 | B2 | 2/2007 | Elbe et al. |
| 7,179,840 | B2 | 2/2007 | Rieck et al. |
| 7,208,169 | B2 | 4/2007 | Dunkel et al. |
| 7,390,806 | B2 | 6/2008 | Lee et al. |
| 7,393,856 | B2 | 7/2008 | Bellinger-Kawahara et al. |
| 7,465,836 | B2 | 12/2008 | Lee et al. |
| 7,582,621 | B2 | 9/2009 | Baker et al. |
| 7,652,000 | B2 | 1/2010 | Perry et al. |

(Continued)

FOREIGN PATENT DOCUMENTS

| | | |
|---|---|---|
| AU | 2010203096 A1 | 8/2010 |
| AU | 2012327171 A1 | 6/2013 |

(Continued)

OTHER PUBLICATIONS

Pubchem entry for AN2718 (https://pubchem.ncbi.nlm.nih.gov/compound/11845944) accessed Mar. 1, 2020.

(Continued)

*Primary Examiner* — Taofiq A Solola
(74) *Attorney, Agent, or Firm* — Barnes & Thornburg LLP

(57) ABSTRACT

The present application relates to large-scale methods of uniformly coating packaging surfaces with a benzoxaborole compound.

20 Claims, No Drawings

(56) References Cited

U.S. PATENT DOCUMENTS

| | | |
|---|---|---|
| 7,767,657 B2 | 8/2010 | Baker et al. |
| 7,816,344 B2 | 10/2010 | Baker et al. |
| 7,842,823 B2 | 11/2010 | Chang |
| 7,888,356 B2 | 2/2011 | Lee et al. |
| 7,968,752 B2 | 6/2011 | Lee et al. |
| 8,039,450 B2 | 10/2011 | Akama et al. |
| 8,039,451 B2 | 10/2011 | Baker et al. |
| 8,106,031 B2 | 1/2012 | Lee et al. |
| 8,110,259 B2 | 2/2012 | Siegel et al. |
| 8,115,026 B2 | 2/2012 | Baker et al. |
| 8,168,614 B2 | 5/2012 | Baker et al. |
| 8,343,944 B2 | 1/2013 | Xia et al. |
| 8,436,028 B2 | 5/2013 | Hunt et al. |
| 8,440,642 B2 | 5/2013 | Baker et al. |
| 8,461,134 B2 | 6/2013 | Hernandez et al. |
| 8,461,135 B2 | 6/2013 | Akama et al. |
| 8,461,336 B2 | 6/2013 | Zhou et al. |
| 8,461,364 B2 | 6/2013 | Wheeler et al. |
| 8,470,803 B2 | 6/2013 | Akama et al. |
| 8,501,712 B2 | 8/2013 | Baker et al. |
| 8,546,357 B2 | 10/2013 | Akama et al. |
| 8,669,207 B1 | 3/2014 | Jacobson et al. |
| 8,791,258 B2 | 7/2014 | Chang |
| 8,906,848 B2 | 12/2014 | Wuts et al. |
| 9,138,001 B2 | 9/2015 | Maclean et al. |
| 9,138,002 B2 | 9/2015 | Jacobson et al. |
| 9,145,429 B2 | 9/2015 | Jarnagin et al. |
| 9,185,914 B2 | 11/2015 | Frackenpohl et al. |
| 9,309,508 B2 | 4/2016 | Benkovic et al. |
| 9,346,834 B2 | 5/2016 | Zhou et al. |
| 9,426,996 B2 | 8/2016 | Maclean et al. |
| 9,493,489 B2 | 11/2016 | Jacobs et al. |
| 9,493,490 B1 | 11/2016 | Akama et al. |
| 9,512,148 B2 | 12/2016 | Chellappan et al. |
| 9,572,823 B2 | 2/2017 | Baker et al. |
| 9,585,396 B2 | 3/2017 | Malefyt et al. |
| 9,617,285 B2 | 4/2017 | Akama et al. |
| 9,676,796 B2 | 6/2017 | Kim et al. |
| 9,730,454 B2 | 8/2017 | Jacobson |
| 9,737,075 B2 | 8/2017 | Benkovic et al. |
| 9,889,146 B2 | 2/2018 | Alley et al. |
| 9,944,660 B2 | 4/2018 | Soni et al. |
| 10,011,616 B2 | 7/2018 | Zhang et al. |
| 10,040,806 B2 | 8/2018 | Rajan et al. |
| 10,051,864 B2 | 8/2018 | Stoller et al. |
| 10,070,649 B2 | 9/2018 | Malefyt et al. |
| 10,159,252 B2 | 12/2018 | Jacobson |
| 10,765,117 B2 | 9/2020 | Maclean et al. |
| 11,039,617 B2 | 6/2021 | Maclean et al. |
| 2004/0259842 A1 | 12/2004 | Mikoshiba et al. |
| 2007/0155699 A1 | 7/2007 | Baker et al. |
| 2007/0286822 A1 | 12/2007 | Sanders et al. |
| 2007/0293457 A1 | 12/2007 | Baker et al. |
| 2008/0153992 A1 | 6/2008 | Knott et al. |
| 2008/0293675 A1 | 11/2008 | Lee et al. |
| 2008/0317737 A1 | 12/2008 | Patel et al. |
| 2009/0148623 A1 | 6/2009 | Sandmeier et al. |
| 2009/0170861 A1 | 7/2009 | Ting et al. |
| 2009/0227541 A1 | 9/2009 | Baker et al. |
| 2009/0239824 A1 | 9/2009 | Lee et al. |
| 2009/0291917 A1 | 11/2009 | Akama et al. |
| 2010/0004205 A1 | 1/2010 | Mayer |
| 2010/0158992 A1 | 6/2010 | Black et al. |
| 2010/0190748 A1 | 7/2010 | Baker et al. |
| 2010/0256092 A1 | 10/2010 | Xia et al. |
| 2010/0267981 A1 | 10/2010 | Baker et al. |
| 2010/0292504 A1 | 11/2010 | Baker et al. |
| 2011/0059985 A1 | 3/2011 | Schmidts et al. |
| 2011/0076261 A1 | 3/2011 | Patel et al. |
| 2011/0082118 A1 | 4/2011 | Patel et al. |
| 2011/0123624 A1 | 5/2011 | Zasloff |
| 2011/0124597 A1 | 5/2011 | Hernandez et al. |
| 2011/0136763 A1 | 6/2011 | Xia et al. |
| 2011/0152217 A1 | 6/2011 | Wheeler et al. |
| 2011/0166103 A1 | 7/2011 | Akama et al. |
| 2011/0166104 A1 | 7/2011 | Zhou et al. |
| 2011/0172187 A1 | 7/2011 | Hernandez et al. |
| 2011/0183969 A1 | 7/2011 | Birch et al. |
| 2011/0190235 A1 | 8/2011 | Chen et al. |
| 2011/0207701 A1 | 8/2011 | Zhou et al. |
| 2011/0207702 A1 | 8/2011 | Jacobs et al. |
| 2011/0212918 A1 | 9/2011 | Hernandez et al. |
| 2011/0319361 A1 | 12/2011 | Baker et al. |
| 2012/0035132 A1 | 2/2012 | Jarnagin et al. |
| 2012/0115813 A1 | 5/2012 | Hernandez et al. |
| 2012/0214765 A1 | 8/2012 | Akama et al. |
| 2012/0264714 A1 | 10/2012 | Baker et al. |
| 2012/0289686 A1 | 11/2012 | Baker et al. |
| 2012/0295875 A1 | 11/2012 | Zhou et al. |
| 2013/0059802 A1 | 3/2013 | Baker et al. |
| 2013/0059803 A1 | 3/2013 | Baker et al. |
| 2013/0064783 A1 | 3/2013 | Baker et al. |
| 2013/0131016 A1 | 5/2013 | Akama et al. |
| 2013/0131017 A1 | 5/2013 | Akama et al. |
| 2013/0165411 A1 | 6/2013 | Gordeev et al. |
| 2013/0196433 A1 | 8/2013 | Raines et al. |
| 2013/0210770 A1 | 8/2013 | Baker et al. |
| 2013/0231304 A1 | 9/2013 | Jacobs et al. |
| 2013/0244980 A1 | 9/2013 | Baker et al. |
| 2013/0298290 A1 | 11/2013 | Haas et al. |
| 2013/0316979 A1 | 11/2013 | Baker et al. |
| 2014/0088041 A1 | 3/2014 | Koop et al. |
| 2014/0155305 A1 | 6/2014 | Hartshorne et al. |
| 2014/0259230 A1 | 9/2014 | Bobbio et al. |
| 2015/0202321 A1 | 7/2015 | Alam et al. |
| 2016/0199351 A1 | 7/2016 | Rappleye et al. |
| 2016/0340369 A1 | 11/2016 | Chen et al. |
| 2017/0000132 A1 | 1/2017 | Rajan et al. |
| 2017/0000133 A1 | 1/2017 | Rajan et al. |
| 2017/0037258 A1 | 2/2017 | Benkovic et al. |
| 2017/0042966 A1 | 2/2017 | Van Der Weerden et al. |
| 2017/0216327 A1 | 8/2017 | Coronado et al. |
| 2017/0251673 A1 | 9/2017 | Cifuentes et al. |
| 2017/0280724 A1 | 10/2017 | Jacobson |
| 2017/0295809 A1 | 10/2017 | Malefyt et al. |
| 2017/0319536 A1 | 11/2017 | Blaszczyk et al. |
| 2017/0327519 A1 | 11/2017 | Akama et al. |
| 2017/0340607 A1 | 11/2017 | Sibley et al. |
| 2017/0355719 A1 | 12/2017 | Hernandez et al. |
| 2018/0000089 A1 | 1/2018 | Stierli et al. |
| 2018/0000090 A1 | 1/2018 | Rajan et al. |
| 2018/0009831 A1 | 1/2018 | Kovi et al. |
| 2018/0016285 A1 | 1/2018 | Baker et al. |
| 2018/0065994 A1 | 3/2018 | Akama et al. |
| 2018/0139975 A1 | 5/2018 | Malefyt et al. |
| 2018/0179229 A1 | 6/2018 | Barbosa et al. |
| 2018/0179233 A1 | 6/2018 | Gamsey et al. |
| 2018/0201628 A1 | 7/2018 | James et al. |
| 2018/0213781 A1 | 8/2018 | Muehlebach et al. |
| 2018/0220654 A1 | 8/2018 | Jacobson et al. |
| 2018/0230169 A1 | 8/2018 | Ramanujachary et al. |
| 2018/0244699 A1 | 8/2018 | Rajan et al. |
| 2022/0361503 A1 | 11/2022 | MacLean et al. |

FOREIGN PATENT DOCUMENTS

| | | |
|---|---|---|
| AU | 2012327230 A1 | 7/2013 |
| CA | 2190155 A1 | 12/1995 |
| CA | 2635680 A1 | 7/2007 |
| CA | 2642583 A1 | 8/2007 |
| CA | 2680587 A1 | 9/2008 |
| CN | 101505603 A | 8/2009 |
| DE | 102012006458 A1 | 9/2013 |
| EP | 765331 A1 | 4/1997 |
| EP | 1444981 A1 | 8/2004 |
| EP | 1765358 A2 | 3/2007 |
| EP | 1765360 A2 | 3/2007 |
| EP | 1980564 A1 | 10/2008 |
| EP | 2343304 A1 | 7/2011 |
| EP | 2564857 A1 | 3/2013 |
| GB | 961280 A | 6/1964 |

(56) References Cited

FOREIGN PATENT DOCUMENTS

| | | |
|---|---|---|
| GB | 1006336 A | 9/1965 |
| GB | 1396904 A | 6/1975 |
| WO | 9531970 A1 | 11/1995 |
| WO | 9533754 A1 | 12/1995 |
| WO | 9821945 A1 | 5/1998 |
| WO | 2005087742 A1 | 9/2005 |
| WO | 2006089067 A2 | 8/2006 |
| WO | 2006102604 A2 | 9/2006 |
| WO | 2007071632 A2 | 6/2007 |
| WO | 2007078340 A2 | 7/2007 |
| WO | 2007079119 A2 | 7/2007 |
| WO | 2007095638 A2 | 8/2007 |
| WO | 2007131072 A2 | 11/2007 |
| WO | 2007146965 A2 | 12/2007 |
| WO | 2008064345 A2 | 5/2008 |
| WO | 2008070257 A2 | 6/2008 |
| WO | 2008115385 A2 | 9/2008 |
| WO | 2008156798 A1 | 12/2008 |
| WO | 2008157726 A1 | 12/2008 |
| WO | 2009046098 A1 | 4/2009 |
| WO | 2009053741 A2 | 4/2009 |
| WO | 2009111676 A2 | 9/2009 |
| WO | 2009130481 A1 | 10/2009 |
| WO | 2009140309 A2 | 11/2009 |
| WO | 2009144473 A1 | 12/2009 |
| WO | 2010027975 A1 | 3/2010 |
| WO | 2010028005 A1 | 3/2010 |
| WO | 2010045503 A1 | 4/2010 |
| WO | 2010045505 A1 | 4/2010 |
| WO | 2010080558 A1 | 7/2010 |
| WO | 2010136475 A1 | 12/2010 |
| WO | 2011017125 A1 | 2/2011 |
| WO | 2011019612 A1 | 2/2011 |
| WO | 2011019616 A1 | 2/2011 |
| WO | 2011019618 A1 | 2/2011 |
| WO | 2011022337 A1 | 2/2011 |
| WO | 2011037731 A1 | 3/2011 |
| WO | 2011043817 A1 | 4/2011 |
| WO | 2011049971 A1 | 4/2011 |
| WO | 2011060196 A1 | 5/2011 |
| WO | 2011060199 A1 | 5/2011 |
| WO | 2011063293 A1 | 5/2011 |
| WO | 2011094450 A1 | 8/2011 |
| WO | 2011116348 A1 | 9/2011 |
| WO | 2011150190 A2 | 12/2011 |
| WO | 2012033858 A2 | 3/2012 |
| WO | 2012067663 A1 | 5/2012 |
| WO | 2012069652 A2 | 5/2012 |
| WO | 2012139134 A2 | 10/2012 |
| WO | 2012154213 A1 | 11/2012 |
| WO | 2013033270 A2 | 3/2013 |
| WO | 2013050591 A2 | 4/2013 |
| WO | 2013057740 A2 | 4/2013 |
| WO | 2013058824 A1 | 4/2013 |
| WO | 2013078070 A1 | 5/2013 |
| WO | 2013078071 A1 | 5/2013 |
| WO | 2013093615 A1 | 6/2013 |
| WO | 2013108024 A1 | 7/2013 |
| WO | 2013110005 A1 | 7/2013 |
| WO | 2013154759 A1 | 10/2013 |
| WO | 2015097237 A1 | 7/2015 |
| WO | 2016015094 A1 | 2/2016 |
| WO | 2016151293 A1 | 9/2016 |
| WO | 2017102565 A1 | 6/2017 |
| WO | 2017125835 A1 | 7/2017 |
| WO | 2017136930 A1 | 8/2017 |
| WO | 2017180695 A1 | 10/2017 |
| WO | 2017183043 A1 | 10/2017 |
| WO | 2017207358 A1 | 12/2017 |
| WO | 2017216191 A1 | 12/2017 |
| WO | 2017216722 A2 | 12/2017 |
| WO | 2018060140 A1 | 4/2018 |
| WO | 2018102261 A2 | 6/2018 |
| WO | 2018156554 A1 | 8/2018 |
| WO | 2018160845 A1 | 9/2018 |

OTHER PUBLICATIONS

Dauthy, "Fruit and Vegetable processing: Chapter 5.3 Chemical Preservation," FAO Argricultural Services Bulletin, 1995, 119.
Reddy et al, "1-MCP, a novel plant growth regulator for regulation of ripening," Agricultural & Horticultural Sciences, 2014.
Seiradake E, et al., "Antifungal activity and mechanism of action of a benzoxaborole, AN2718, which is in development for the treatment of Tinea pedis," Abstract F1-1176, IDSA Poster Session: New Anti-Fungal Agents (2008).
Mao W, et al., "AN2718 has broad spectrum antifungal activity necessary for the topical treatment of skin and nail fungal infections," Abstract p. 2422, J. American Acad. Dermatology 60(3) Supplement 1, AB116 (2009).
Rolshausen PE, et al., "Use of boron for the control of Eutypa dieback of grapevines," Plant Diseases 89(7): 734-738 (2005).
Qin G, et al., "Inhibitory effect of boron against Botrytis cinerea on table grapes and its possible mechanisms of action," International Journal of Food Microbiology 138: 145-150 (2010).
Thomidis T and Exadaktylou E., "Effect of boron on the development of brown rot (*Monilinia laxa*) on peaches," Crop Prot. 29: 572-576 (2010).
Expert Declaration of Phillip M. Brannen, Ph.D., filed in an Inter Partes Review of U.S. Pat. No. 10,130,096, filed Nov. 5, 2019.
Boric Acid, Chemical Watch Factsheet, 21, 18-19 (2001).
Ligon JM, et al, "Natural products with antifungal activity from Pseudomonas biocontrol bacteria," Pest Management Science 56: 688-695 (2000).
Alumni Product Registration (Jun. 9, 2010).
Propi-Shield Product Registration (Aug. 11, 2005).
Tilt Label (2006).
Mahmoud Yag, et al., "Recent approaches for controlling brown spot disease of faba bean in Egypt," Egypt Acad. J. Biol. Sci. 3: 41-53 (2011).
Ware G, "Substituted aromatics," pp. 148-149, In: Fundamentals of Pesticides: a self-instruction guide, Tomson Publications, Fresno, CA (1991).
Bertelsen JR, et al., "Fungicidal effects of azoxystrobin and epoxiconazole on phyllosphere fungi, senescence and yield of winter wheat," Plant Pathology 50: 190-205 (2001).
Propi-Shield Label Amendment (Nov. 29, 2006).
Azotech Label Amendment (Sep. 7, 2007).
PptiShield Label (2009).
Abound label (2007).
Chlorosel label (2010).
Ultrex label (2005).
Chloroneb Fact Sheet (2005).
Dichloran Label Amendment (Aug. 5, 2010).
Expert Declaration of Dennis Hall, Ph.D. filed in an Inter Partes Review of U.S. Pat. No. 10,130,096, filed Nov. 5, 2019.
Patent Owner Preliminary Response filed in an Inter Partes Review of U.S. Pat. No. 10,130,096, filed Feb. 18, 2020.
Dictionary Reference filed in an Inter Partes Review of U.S. Pat. No. 10,130,096.
Petition for Inter Partes Review of U.S. Pat. No. 10,130,096, filed Nov. 5, 2019.
Marsh et al., J. Good Sc. 2007, vol. 72, R39-R54.
Rock, F.L.W. Matoe, et al., "An Antifungal Agent Inhibits an Aminoacyl-tRNA Synthetase by Trapping tRNA in the Editing Site," Science 316, 2007, 1759-1761.
Edwards, "Organoboron reagents and recent strategies in rhodium catalysed additions," Ph. D. Thesis submitted to University of Bath, 2011, pp. 1-293.
Ma, X. et al., "Synthesis of Boroxine-Linked Aluminium Complexes," Inorg. Chem., 2011, 50, 2010-2014.
Alexander, C. et al., "Imprinted Polymers as Protecting Groups for Regioselective Modifcation of Polyfunctional Substrates," J. Am. Chem. Soc., 1999, 121 , 6640-6651.
Greig, L. et al., "The dynamic covalent chemistry of mono- and bifunctional boroxoaromatics", Tetrahedron, 2006, 63, 2391-2403.
Weike, Z. et al.,"Preparation of 2-oxygen derivatives of 1,2-oxaborolane from 2-allyloxy-1,2-oxaborolane," Journal of Organometallic Chemistry, 1990, 387, 131-146.

(56) References Cited

OTHER PUBLICATIONS

Office Action for Japanese Patent Application No. 2016-517975, dated Dec. 24, 2019, 4 pages.

Kumar, J.S. et al., "Development of Practical Methodologies for the Synthesis of Functionalized Benzoboroxoles", Tetrahendron Letters, Elsevier, Amsterdam, NL, col. 51, No. 34, Aug. 24, 2010, pp. 4482-4485.

Mao, W., "AN2690, a topical antifungal agent in development for the treatment of onychmycosis represents a new class and has a novel mechanism of action", Anacor Pharmaceuticals AG, Aug. 20, 2008, XP007921849, www.anacor.com/pdf/SID_p769.pdf [retrieved on Jul. 11, 2013]. XP007921849, wwww.

Ding et al., "Design, Synthesis, and Structure—Activity Relationship of Trypanosoma brucei Leucyl-tRNA Synthetase Inhibitors as Antitrypanosomal Agents," J. Med. Chem. (2011), vol. 54(5), pp. 1276-1287.

Haynes et al., "Arylboronic Acids. VIII. Reactions of Boronophthalide", Noyes Chemical Laboratory, University of Illinois, Nov. 1964, pp. 3229-3233 Urbana, USA (5 pages).

Brown et al., "Convenient Procedures for the Preparation of Alkyl Borate Esters," Proc. for Prepn. Alkyl Borate Esters, Aug. 5, 1956, pp. 3613-3614.

Shen et al., "Changes of respiration and ethylene production and effects of 1-MCP during the fermentation softening of chinese winter jujube fruit," Zhongguo Nongye Daxue Xuebao (2004) vol. 9(2), pp. 36-39.

Guillen et al., "Efficacy of 1-MCP treatment in tomato fruit 2. Effect of cultivar and ripening stage at harvest," Postharvest Biology and Technol. (2006) vol. 42(3), pp. 235-242.

Carillo et al., "1-Methylcyclopropene delays araze a ripening and improves postharvest fruit quality," LWT—Food Sci. and Tech. (2011) vol. 44, pp. 250-255.

International Search Report for PCT/US2014/013510, Dow AgroSciences LLC, Jun. 25, 2014.

Brown et al. Proc. for Prepn. Alkyl Borate Esters, (1956), pp. 3613-3614.

Baker, Stephen et al., Discovery of new boron-containing antifungal agent, 5-fluoro-1,3,dihydroxy-2-1-benzoxabrole (AN2690), for the potential treatment of onychomycosis, Journal of Medicinal Chemistry, Jul. 1, 2006, 49, 4447-4450.

"Smart Fog ES-100 models Installation and Operation Manual", Jan. 1, 2012 (Jan. 1, 2012), pp. 1-30, XP055724760, U.S.A., Retrieved from the Internet: URL:https://www.smartfog.com/pdf/mn_es100.pdf [retrieved on Aug. 24, 2020].

EPO Examination Report for Application No. 17763834.3, dated Aug. 31, 2020 (Aug. 31, 2020) 10 pages.

LARGE-SCALE METHODS OF UNIFORMLY COATING PACKAGING SURFACES WITH A VOLATILE ANTIMICROBIAL TO PRESERVE FOOD FRESHNESS

CROSS-REFERENCE TO RELATED APPLICATION

This application is a continuation of U.S. patent application Ser. No. 17/346,446, filed Jun. 14, 2021, which is a continuation of U.S. patent application Ser. No. 16/707,516, filed Dec. 9, 2019, which is a continuation-in-part of U.S. patent application Ser. No. 15/485,500, filed Apr. 12, 2017, which claims the benefit of priority under 35 U.S.C. § 119(e) of U.S. Provisional Patent Application No. 62/323,247, filed Apr. 15, 2016, the content of which is incorporated by reference in its entirety.

This application is a continuation of U.S. patent application Ser. No. 17/346,446, filed Jun. 14, 2021, which is a continuation of U.S. patent application Ser. No. 16/707,516, filed Dec. 9, 2019, which is also a continuation-in-part of Ser. No. 16/123,735, filed Sep. 6, 2018, now U.S. Pat. No. 10,765,117, which is a continuation of Ser. No. 15/445,247, filed Feb. 28, 2017, now U.S. Pat. No. 10,070,649, which is a continuation-in-part of U.S. patent application Ser. No. 14/690,929, filed on Apr. 20, 2015, now U.S. Pat. No. 9,585,396, which claims the benefit of priority under 35 U.S.C. § 119(e) of U.S. Provisional Patent Application No. 61/991,821, filed May 12, 2014, the contents of all of which are incorporated by reference in their entireties.

U.S. patent application Ser. No. 14/690,929, now U.S. Pat. No. 9,585,396, filed on Apr. 20, 2015, is also a continuation-in-part of U.S. patent application Ser. No. 14/294,057, now U.S. Pat. No. 9,426,996, filed on Jun. 2, 2014, which is a continuation of U.S. patent application Ser. No. 14/167,093, now U.S. Pat. No. 9,138,001, filed on Jan. 29, 2014, which claims the benefit of priority under 35 U.S.C. § 119(e) of U.S. Provisional Patent Application No. 61/758,313, filed Jan. 30, 2013, the contents of all of which are hereby incorporated by reference in their entireties.

U.S. patent application Ser. No. 14/690,929, now U.S. Pat. No. 9,585,396, filed on Apr. 20, 2015, is also a continuation-in-part of U.S. patent application Ser. No. 14/182,793, now U.S. Pat. No. 9,138,002, filed on Feb. 18, 2014, which is a divisional of U.S. patent application Ser. No. 13/945,577, now U.S. Pat. No. 8,669,207, filed on Jul. 18, 2013, which claims the benefit of priority under 35 U.S.C. § 119(e) of 61/831,187, filed Jun. 5, 2013, and U.S. Provisional Patent Application No. 61/758,313, filed Jan. 30, 2013, the contents of all of which are hereby incorporated by reference in their entireties.

FIELD OF THE PRESENT APPLICATION

The present application relates to large-scale methods of uniformly coating packaging surfaces with a benzoxaborole compound.

BACKGROUND

Benzoxaborole is a drug known to be effective in treating eukaryotic fungal and parasitic infections. For example, benzoxaborole is used to treat fungal conditions affecting the toenails and fingernails of humans, such as Onychomycosis. Benzoxaborole is also known to be an effective treatment of Human African Trypanosomiasis, commonly called African Sleeping Sickness, which is caused by *T. brucei* parasites that infect thousands of people annually in sub-Saharan Africa.

Benzoxaborole has also been shown to have antimicrobial effects in plants. For example, benzoxaborole compounds have been proven to be effective as a volatile plant fungicide. However, coating packaging surfaces with a volatile biological control agent, such as a benzoxaborole compound, to provide antimicrobial protection to food, such as crops and meats, and to preserve food freshness has not been reported.

The present disclosure describes large-scale methods of applying volatile antimicrobial compounds on food containers and packaging materials to inhibit microorganisms responsible for decay. More specifically, the present disclosure provides methods of coating benzoxaboroles on the surface of food containers and packaging materials in mass in order to provide antimicrobial protection to food. In addition, the present disclosure describes methods to treat food products against microorganisms that are detrimental to the preservation of the freshness of food, such as plant, crops, or meats.

SUMMARY OF THE INVENTION

The present disclosure provides a method of treating food products with an antimicrobial agent. The method comprises administering an antimicrobial agent, sometimes called a benzoxaborole compound, to one or more surfaces of a chamber. The method also comprises drying the one or more surfaces of the chamber. The method further comprises placing a food product inside of the chamber. Finally, the method comprises vaporizing the benzoxaborole compound from the one or more surfaces of the chamber to treat the food product.

In the method described herein, the food product may be a plant crop or a meat, wherein the crop may be a fruit selected from the group consisting of a strawberry, a raspberry, a blackberry, or a blueberry. In addition, the benzoxaborole compound of the present method may be selected from the group consisting of Compound A, Compound B, and/or Compound C. The chamber of the method may be a clamshell, and the clamshell may comprise polyethylene terephthalate. Finally, the benzoxaborole compound of the present method may be administered to the chamber by drenching, spraying, painting, vaporizing, and/or sublimation.

The present disclosure is also directed to a large-scale method of treating a plurality of chambers with an antimicrobial agent. The method comprises placing a plurality of chambers in a position to be treated, wherein each of the plurality of chambers comprises one or more surfaces. The method further comprises administering a benzoxaborole compound to the one or more surfaces of the plurality of chambers. In addition, the method comprises drying the one or more surfaces of the plurality of chambers, wherein the drying may be instantaneous. Further, the large-scale method comprises affixing the benzoxaborole compound to the one or more surfaces of the plurality of chambers.

The benzoxaborole compound of the present large-scale method may be selected from the group consisting of Compound A, Compound B, and/or Compound C, and may be administered to the plurality of chambers by drenching, spraying, painting, vaporizing, or sublimation.

The benzoxaborole compound may also be administered to the plurality of chambers during preformation, formation, or postformation of the plurality of chambers. The surfaces of the plurality of chambers of the large-scale method may further comprise a liquid-absorbing material. The plurality of chambers of the large-scale method may comprise a plurality of clamshells, and the plurality of clamshells may comprise polyethylene terephthalate.

DETAILED DESCRIPTION

The following numbered embodiments are contemplated and are non-limiting:

1. A method of treating a food product with an antimicrobial agent, the method comprising:
    administering a benzoxaborole treatment to one or more surfaces of a food packaging material, wherein the benzoxaborole treatment comprises one or more benzoxaborole compounds,
    drying the one or more surfaces of the food packaging material,
    placing a food product inside of the food packaging material, and
    vaporizing the benzoxaborole compound from the one or more surfaces of the food packaging material to treat the food product located therein.
2. The method of clause 1, wherein the food product is a plant, a crop, or a meat.
3. The method of clause 1 or clause 2, wherein the food product is a fruit.
4. The method of any of clauses 1 to 3, wherein the food product is selected from the group consisting of a strawberry, a raspberry, a blackberry, and a blueberry.
5. The method of any one of clauses 1 to 4, wherein the benzoxaborole compound is selected from the group consisting of Compound A, Compound B, Compound C, and combinations thereof.
6. The method of any one of clauses 1 to 5, wherein Compound A has the structure:

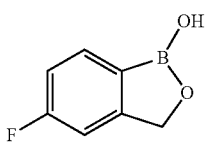

or an analog or a derivative thereof.

7. The method of any one of clauses 1 to 5, wherein Compound B has the structure:

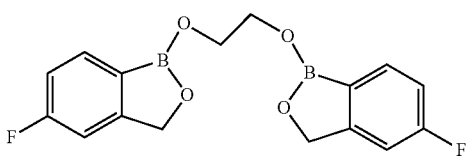 [SMILES: Fc1ccc2c(c1)COB2OCCOB1OCc2cc(F)ccc21]

or an analog or a derivative thereof.

8. The method of any one of clauses 1 to 5, wherein Compound C has the structure:

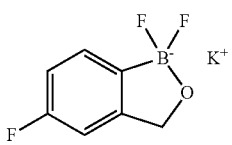

or an analog or a derivative thereof.

9. The method of any one of clauses 1 to 8, wherein the benzoxaborole compound is in the form of a liquid, a gas, or a solid.
10. The method of any one of clauses 1 to 9, wherein the food packaging material is comprised by a chamber.
11. The method of clause 10, wherein the chamber is selected from the group consisting of a container, a liner material, one chamber, and a plurality of chambers.
12. The method of clause 10 or clause 11, wherein the chamber is a clamshell.
13. The method of clause 12, wherein the clamshell comprises polyethylene terephthalate (PET).
14. The method of any one of clauses 1 to 13, wherein the benzoxaborole treatment is embedded into, impregnated within, or coated onto the food packaging material.
15. The method of any one of clauses 1 to 14, wherein the benzoxaborole treatment is embedded into the food packaging material.
16. The method of any one of clauses 1 to 14, wherein the benzoxaborole treatment is coated onto the food packaging material.
17. The method of any one of clauses 1 to 14, wherein the benzoxaborole treatment is impregnated into the food packaging material.
18. The method of any one of clauses 1 to 17, wherein the benzoxaborole treatment is in the form of a spray, a liquid, a mist, a gel, a thermal fog, a non-thermal fog, a dip, a drench, a vapor, a gas, or sublimation.
19. The method of any one of clauses 1 to 18, wherein the benzoxaborole treatment further comprises a treatment carrier.
20. The method of clause 19, wherein the treatment carrier comprises a liquid, a gas, a solution, a solvent, and a chemical.
21. The method of clause 19 or clause 20, wherein the treatment carrier is a liquid.
22. The method of any one of clauses 19 to 21, wherein the treatment carrier is selected from the group consisting of water, saline, a buffer, a solution, a solvent, a solvent-based solution, and a combination thereof.
23. The method of clause any one of clauses 19 to 22, wherein the treatment carrier is supercritical $CO_2$.
24. The method of clause 19 or clause 20, wherein the treatment carrier is a gas.
25. The method of any one of clauses 19, 20, or 24, wherein the treatment carrier is selected from the group consisting of nitrogen ($N_2$), carbon dioxide ($CO_2$), and sulfur dioxide ($SO_2$).
26. The method of any one of clauses 19, 20, 24, or 25, wherein the treatment carrier is nitrogen ($N_2$).
27. The method of any one of clauses 19, 20, 24, or 25, wherein the treatment carrier is carbon dioxide ($CO_2$).
28. The method of any one of clauses 19, 20, 24, or 25, wherein the treatment carrier is sulfur dioxide ($SO_2$).
29. The method of any one of clauses 1 to 28, wherein the benzoxaborole treatment is effective against plant pathogens.
30. The method of clause 29, wherein the plant pathogens are fungal pathogens.
31. The method of clause 29 or clause 30, wherein the plant pathogens are selected from the group consisting of *Acremonium* spp., *Albugo* spp., *Alternaria* spp., *Ascochyta* spp., *Aspergillus* spp., *Botryodiplodia* spp., *Botryospheria* spp., *Botrytis* spp., *Byssochlamys* spp., *Candida* spp., *Cephalosporium* spp., *Ceratocystis* spp., *Cercospora* spp., *Chalara* spp., *Cladosporium* spp., *Colletotrichum* spp.,

*Cryptosporiopsis* spp., *Cylindrocarpon* spp., *Debaryomyces* spp., *Diaporthe* spp., *Didymella* spp., *Diplodia* spp., *Dothiorella* spp., *Elsinoe* spp., *Fusarium* spp., *Geotrichum* spp., *Gloeosporium* spp., *Glomerella* spp., *Helminthosporium* spp., *Khuskia* spp., *Lasiodiplodia* spp., *Macrophoma* spp., *Macrophomina* spp., *Microdochium* spp., *Monilinia* spp., *Monilochaethes* spp., *Mucor* spp., *Mycocentrospora* spp., *Mycosphaerella* spp., *Nectria* spp., *Neofabraea* spp., *Nigrospora* spp., *Penicillium* spp., *Peronophythora* spp., *Peronospora* spp., *Pestalotiopsis* spp., *Pezicula* spp., *Phacidiopycnis* spp., *Phoma* spp., *Phomopsis* spp., *Phyllosticta* spp., *Phytophthora* spp., *Polyscytalum* spp., *Pseudocercospora* spp., *Pyricularia* spp., *Pythium* spp., *Rhizoctonia* spp., *Rhizopus* spp., *Sclerotium* spp., *Sclerotinia* spp., *Septoria* spp., *Sphaceloma* spp., *Sphaeropsis* spp., *Stemphyllium* spp., *Stilbella* spp., *Thielaviopsis* spp., *Thyronectria* spp., *Trachysphaera* spp., *Uromyces* spp., *Ustilago* spp., *Venturia* spp., and *Verticillium* spp., and bacterial pathogens, such as *Bacillus* spp., *Campylobacter* spp., *Clavibacter* spp., *Clostridium* spp., *Erwinia* spp., *Escherichia* spp., *Lactobacillus* spp., *Leuconostoc* spp., *Listeria* spp., *Pantoea* spp., *Pectobacterium* spp., *Pseudomonas* spp., *Ralstonia* spp., *Salmonella* spp., *Shigella* spp., *Staphylococcus* spp., *Vibrio* spp., *Xanthomonas* spp., and *Yersinia* spp.

32. The method of any one of clauses 29 to 31, wherein the plant pathogens are selected from the group consisting of *Botrytis cinerea, Mucor piriformis, Fusarium sambucinum, Aspergillus brasiliensis,* and *Peniciliium expansum.*

33. The method of any one of clauses 10 to 32, wherein the chamber is open, closed, or sealed.

34. The method of any one of clauses 10 to 33, wherein the chamber is sealed.

35. The method of any one of clauses 10 to 34, wherein the chamber is air-tight.

36. The method of any one of clauses 10 to 35, wherein the chamber is semipermeable or impermeable.

37. The method of any one of clauses 10 to 36, wherein the chamber is made of a material selected from the group consisting of cardboard, paper, paperboard, corrugated paper, plastic, glass, polyester, polystyrene, cellulosic material, metal, and cement.

38. The method of clause 37, wherein the metal is selected from the group consisting of aluminum, foils, laminates, tinplate, and steel.

39. The method of clause 38, wherein the steel is tin-free steel.

40. The method of clause 37, wherein the plastic is selected from the group consisting of thermosets and thermoplastics.

41. The method of clause 37, wherein the polyester is selected from the group consisting of polycarbonate, polyethylene naphthalate, and polyethylene terephthalate (PET).

42. The method of any one of clauses 10 to 41, wherein the chamber comprises a port, an outlet, or both.

43. The method of any one of clauses 10 to 42, wherein the chamber has a volume from between about 0.1 L to about 50 L.

44. The method of any one of clauses 10 to 43, wherein the chamber comprises a plurality of individual clamshells.

45. The method of any one of clauses 10 to 44, wherein the chamber comprises between about 2 clamshells to about 384,000,000 clamshells.

46. The method of any one of clauses 10 to 45, wherein the chamber further comprises a liquid-absorbing material.

47. The method of clause 46, wherein the liquid-absorbing material is comprised on the interior of the chamber or on the exterior of the chamber.

48. The method of clause 46 or clause 47, wherein the liquid-absorbing material is comprised on the interior of the chamber.

49. The method of clause 47 or clause 48, wherein the liquid-absorbing material is comprised on the internal top, the internal bottom, or the internal side panels of the chamber.

50. The method of clause 46 or clause 47, wherein the liquid-absorbing material is comprised on the exterior of the chamber.

51. The method of clause 47 or clause 50, wherein the liquid-absorbing material is comprised on the external top, the external bottom, or the external side panels of the chamber.

52. The method of any one of clauses 46 to 51, wherein the liquid-absorbing material is attached or affixed to the chamber.

53. The method of any one of clauses 46 to 52, wherein the liquid-absorbing material is comprised in a chamber component selected from the group consisting of a liner, a wrapping, a label, a tag, a sticker, and a pad.

54. The method of any one of clauses 45 to 53, wherein the liquid-absorbing material is selected from the group consisting of cotton, paper, and foam.

55. The method of any one of clauses 46 to 54, wherein the liquid-absorbing material is a reservoir capable of releasing the benzoxaborole treatment to the food product comprised in the chamber.

56. The method of any one of clauses 46 to 55, wherein the liquid-absorbing material provides for quick-release or slow-release of the benzoxaborole treatment to the food product comprised in the chamber over a time period.

57. The method of any one of clauses 46 to 56, wherein the liquid-absorbing material provides for quick-release of the benzoxaborole treatment to the food product comprised in the chamber over a time period.

58. The method of any one of clauses 46 to 56, wherein the liquid-absorbing material provides for slow-release of the benzoxaborole treatment to the food product comprised in the chamber over a time period.

59. The method of clause 56 or clause 57, wherein the time period for quick-release of the benzoxaborole treatment by the liquid-absorbing material is about 12 hours or less.

60. The method of any one of clauses 56, 57, or 59, wherein the time period for quick-release of the benzoxaborole treatment by the liquid-absorbing material is between about 5 seconds to about 12 hours or less.

61. The method of clause 56 or clause 58, wherein the time period for slow-release of the benzoxaborole treatment by the liquid-absorbing material is over 12 hours.

62. The method of any one of clauses 56, 58, or 61, wherein the time period for slow-release of the benzoxaborole treatment by the liquid-absorbing material is between over 12 hours to about 31 days.

63. The method of any one of clauses 10 to 62, wherein the chamber further comprises one or more apertures.

64. The method of clause 63, wherein the one or more apertures has a size between about 2 mm to about 2 cm.

65. The method of clause 63 or clause 64, wherein the one or more apertures has a location on the chamber selected from the group consisting of the base, the lid, the sides, or a combination thereof.

66. The method of any one of clauses 63 to 65, wherein the one or more apertures enables introduction of the benzoxaborole treatment, the treatment carrier, or a combination thereof to the chamber.

67. The method of any one of clauses 63 to 65, wherein the one or more apertures enables release of the benzoxaborole treatment, the treatment carrier, or a combination thereof from the chamber.

68. The method of any one of clauses 1 to 67, wherein the food products are manually or robotically placed in the chamber.

69. The method of any one of clauses 1 to 68, wherein the food products are treated post-harvest.

70. The method of any one of clauses 1 to 69, wherein the distance between the food products and the food packaging material comprising the benzoxaborole treatment is no greater than 6 feet.

71. The method of any one of clauses 1 to 70, wherein the distance between the food products and the food packaging material comprising the benzoxaborole treatment is between about 0.1 inches and about 6 feet.

72. The method any one of clauses 1 to 71, wherein the one or more food products are treated for an initial time period ranging from about 12 hours to about 5 days.

73. The method of any one of clauses 1 to 72, wherein the benzoxaborole treatment concentration ranges from about 0.1 mg/chamber to about 10 mg/chamber.

74. The method of any one of clauses 1 to 73, wherein drying the one or more surfaces of the food packaging material occurs at room temperature, wherein room temperature is between about 21° C. and about 23° C.

75. The method of any one of clauses 1 to 74, wherein drying the one or more surfaces of the food packaging material occurs instantaneously or within seconds.

76. The method of any one of clauses 1 to 75, wherein drying the one or more surfaces of the food packaging material occurs instantaneously.

77. The method of any one of clauses 1 to 75, wherein drying the one or more surfaces of the food packaging material occurs within seconds 78. The method of any one of clauses 1 to 75 or 77, wherein drying the one or more surfaces of the food packaging material occurs between about 0.1 seconds and about 60 seconds.

79. The method of any one of clauses 1 to 78, wherein the method results in greater uniformity and consistency in application of benzoxaborole treatment to the food packaging material.

80. The method of any one of clauses 1 to 79, wherein the method provides one month of extended antimicrobial protection to the treated food products.

A large-scale method of treating a plurality of chambers with an
    antimicrobial agent, the method comprising:
    placing a plurality of chambers in a position to be treated wherein each of the chambers comprise one or more surfaces,
    administering the benzoxaborole treatment to one or more surfaces of the plurality of chambers during preformation, formation, or postformation of the plurality of chambers, wherein the benzoxaborole treatment comprises one or more benzoxaborole compounds,
    drying the one or more surfaces of the plurality of chambers, and
    affixing the benzoxaborole compound to the one or more surfaces of the
plurality of chambers.

The method of clause 81, wherein the plurality of chambers further
    comprise a food product that is a plant, a crop, or a meat.

The method of clause 82, wherein the food product is a fruit.

The method of any of clauses 82 or clause 83, wherein the food product
    is selected from the group consisting of a strawberry, a raspberry, a blackberry, and a blueberry.

The method of any one of clauses 81 to 84, wherein the benzoxaborole
    compound is selected from the group consisting of Compound A, Compound B, Compound C, and combinations thereof.

86. The method of any one of clauses 81 to 85, wherein Compound A has the structure:

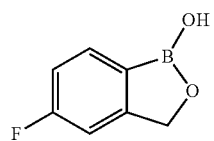

or an analog or a derivative thereof.

87. The method of any one of clauses 81 to 85, wherein Compound B has the structure:

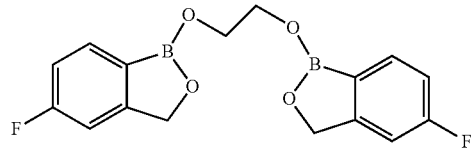 [SMILES: Fc1ccc2c(c1)COB2OCCOB1OCc2cc(F)ccc21]

or an analog or a derivative thereof.

88. The method of any one of clauses 81 to 85, wherein Compound C has the structure:

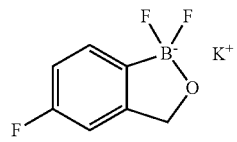

or an analog or a derivative thereof.

89. The method of any one of clauses 81 to 88, wherein the benzoxaborole compound is in the form of a liquid, a gas, or a solid.

90. The method of any one of clauses 81 to 89, wherein the plurality of chambers comprise one or more containers.

91. The method of any one of clauses 81 to 90, wherein the plurality of chambers comprise one or more liner materials.

92. The method of any one of clauses 81 to 91, wherein the plurality of chambers comprise one or more clamshells.

93. The method of any one of clauses 81 to 92, wherein the clamshells comprise polyethylene terephthalate (PET).

94. The method of any one of clauses 81 to 93, wherein the benzoxaborole treatment is embedded into, impregnated within, or coated onto the plurality of chambers.

95. The method of any one of clauses 81 to 94, wherein the benzoxaborole treatment is embedded into the plurality of chambers.

96. The method of any one of clauses 81 to 94, wherein the benzoxaborole treatment is coated onto the plurality of chambers.

97. The method of any one of clauses 81 to 94, wherein the benzoxaborole treatment is impregnated into the plurality of chambers.

98. The method of any one of clauses 81 to 97, wherein the benzoxaborole treatment is in the form of a spray, a liquid, a mist, a gel, a thermal fog, a non-thermal fog, a dip, a drench, a vapor, a gas, or sublimation.

99. The method of any one of clauses 81 to 98, wherein the benzoxaborole treatment further comprises a treatment carrier.

100. The method of clause 99, wherein the treatment carrier comprises a liquid, a gas, a solution, a solvent, and a chemical.

101. The method of clause 99 or clause 100, wherein the treatment carrier is a liquid.

102. The method of any one of clauses 99 to 101, wherein the treatment carrier is selected from the group consisting of water, saline, a buffer, a solution, a solvent, a solvent-based solution, and a combination thereof.

103. The method of clause any one of clauses 99 to 102, wherein the treatment carrier is supercritical $CO_2$.

104. The method of clause 99 or clause 100, wherein the treatment carrier is a gas.

105. The method of any one of clauses 99, 100, or 104, wherein the treatment carrier is selected from the group consisting of nitrogen ($N_2$), carbon dioxide ($CO_2$), and sulfur dioxide ($SO_2$).

106. The method of any one of clauses 99, 100, 104, or 105, wherein the treatment carrier is nitrogen ($N_2$).

107. The method of any one of clauses 99, 100, 104, or 105, wherein the treatment carrier is carbon dioxide ($CO_2$).

108. The method of any one of clauses 99, 100, 104, or 105, wherein the treatment carrier is sulfur dioxide ($SO_2$).

109. The method of any one of clauses 81 to 108, wherein the benzoxaborole treatment is effective against plant pathogens.

110. The method of clause 109, wherein the plant pathogens are fungal pathogens.

111. The method of clause 109 or clause 110, wherein the plant pathogens are selected from the group consisting of *Acremonium* spp., *Albugo* spp., *Alternaria* spp., *Ascochyta* spp., *Aspergillus* spp., *Botryodiplodia* spp., *Botryospheria* spp., *Botrytis* spp., *Byssochlamys* spp., *Candida* spp., *Cephalosporium* spp., *Ceratocystis* spp., *Cercospora* spp., *Chalara* spp., *Cladosporium* spp., *Colletotrichum* spp., *Cryptosporiopsis* spp., *Cylindrocarpon* spp., *Debaryomyces* spp., *Diaporthe* spp., *Didymella* spp., *Diplodia* spp., *Dothiorella* spp., *Elsinoe* spp., *Fusarium* spp., *Geotrichum* spp., *Gloeosporium* spp., *Glomerella* spp., *Helminthosporium* spp., *Khuskia* spp., *Lasiodiplodia* spp., *Macrophoma* spp., *Macrophomina* spp., *Microdochium* spp., *Monilinia* spp., *Monilochaethes* spp., *Mucor* spp., *Mycocentrospora* spp., *Mycosphaerella* spp., *Nectria* spp., *Neofabraea* spp., *Nigrospora* spp., *Penicillium* spp., *Peronophythora* spp., *Peronospora* spp., *Pestalotiopsis* spp., *Pezicula* spp., *Phacidiopycnis* spp., *Phoma* spp., *Phomopsis* spp., *Phyllosticta* spp., *Phytophthora* spp., *Polyscytalum* spp., *Pseudocercospora* spp., *Pyricularia* spp., *Pythium* spp., *Rhizoctonia* spp., *Rhizopus* spp., *Sclerotium* spp., *Sclerotinia* spp., *Septoria* spp., *Sphaceloma* spp., *Sphaeropsis* spp., *Stemphyllium* spp., *Stilbella* spp., *Thielaviopsis* spp., *Thyronectria* spp., *Trachysphaera* spp., *Uromyces* spp., *Ustilago* spp., *Venturia* spp., and *Verticillium* spp., and bacterial pathogens, such as *Bacillus* spp., *Campylobacter* spp., *Clavibacter* spp., *Clostridium* spp., *Erwinia* spp., *Escherichia* spp., *Lactobacillus* spp., *Leuconostoc* spp., *Listeria* spp., *Pantoea* spp., *Pectobacterium* spp., *Pseudomonas* spp., *Ralstonia* spp., *Salmonella* spp., *Shigella* spp., *Staphylococcus* spp., *Vibrio* spp., *Xanthomonas* spp., and *Yersinia* spp.

112. The method of any one of clauses 109 to 111, wherein the plant pathogens are selected from the group consisting of *Botrytis cinerea, Mucor piriformis, Fusarium sambucinum, Aspergillus brasiliensis*, and *Peniciliium expansum*.

113. The method of any one of clauses 90 to 112, wherein the chamber is open, closed, or sealed.

114. The method of clause 113, wherein the chamber is sealed.

115. The method of clause 113 or clause 114, wherein the chamber is sealed air-tight.

116. The method of any one of clauses 90 to 115, wherein the chamber is semipermeable or impermeable.

117. The method of any one of clauses 90 to 116, wherein the chamber is made of a material selected from the group consisting of cardboard, paper, paperboard, corrugated paper, plastic, glass, polyester, polystyrene, cellulosic material, metal, and cement.

118. The method of clause 117, wherein the metal is selected from the group consisting of aluminum, foils, laminates, tinplate, and steel.

119. The method of clause 118, wherein the steel is tin-free steel.

120. The method of clause 117, wherein the plastic is selected from the group consisting of thermosets and thermoplastics.

121. The method of clause 117, wherein the polyester is selected from the group consisting of polycarbonate, polyethylene naphthalate, and polyethylene terephthalate (PET).

122. The method of any one of clauses 90 to 121, wherein the chamber comprises a port, an outlet, or both.

123. The method of any one of clauses 81 to 122, wherein the chamber has a volume from between about 0.1 L to about 50 L.

124. The method of any one of clauses 81 to 123, wherein the chamber comprises a plurality of individual clamshells.

125. The method of any one of clauses 81 to 124, wherein the chamber comprises between about 2 clamshells to about 384,000,000 clamshells.

126. The method of any one of clauses 81 to 125, wherein the chamber further comprises a liquid-absorbing material.

127. The method of clause 126, wherein the liquid-absorbing material is comprised on the interior of the chamber or on the exterior of the chamber.

128. The method of clause 126 or clause 127, wherein the liquid-absorbing material is comprised on the interior of the chamber.

129. The method of clause 127 or clause 128, wherein the liquid-absorbing material is comprised on the internal top, the internal bottom, or the internal side panels of the chamber, or combinations thereof.

130. The method of clause 126 or clause 127, wherein the liquid-absorbing material is comprised on the exterior of the chamber.

131. The method of clause 127 or clause 130, wherein the liquid-absorbing material is comprised on the external top, the external bottom, or the external side panels of the chamber, or combinations thereof.

132. The method of any one of clauses 126 to 131, wherein the liquid-absorbing material is attached or affixed to the chamber.

133. The method of any one of clauses 126 to 132, wherein the liquid-absorbing material is comprised in a chamber component selected from the group consisting of a liner, a wrapping, a label, a tag, a sticker, and a pad.

134. The method of any one of clauses 126 to 133, wherein the liquid-absorbing material is selected from the group consisting of cotton, paper, and foam.

135. The method of any one of clauses 126 to 134, wherein the liquid-absorbing material is a reservoir capable of releasing the benzoxaborole treatment to the food product comprised in the chamber.

136. The method of any one of clauses 126 to 135, wherein the liquid-absorbing material provides for quick-release or slow-release of the benzoxaborole treatment to the food product comprised in the chamber over a time period.

137. The method of any one of clauses 126 to 136, wherein the liquid-absorbing material provides for quick-release of the benzoxaborole treatment to the food product comprised in the chamber over a time period.

138. The method of any one of clauses 126 to 136, wherein the liquid-absorbing material provides for slow-release of the benzoxaborole treatment to the food product comprised in the chamber over a time period.

139. The method of clause 136 or clause 137, wherein the time period for quick-release of the benzoxaborole treatment by the liquid-absorbing material is about 12 hours or less.

140. The method of any one of clauses 136, 137, or 139, wherein the time period for quick-release of the benzoxaborole treatment by the liquid-absorbing material is between about 5 seconds to about 12 hours or less.

141. The method of clause 136 or clause 138, wherein the time period for slow-release of the benzoxaborole treatment by the liquid-absorbing material is over 12 hours.

142. The method of any one of clauses 136, 138, or 141, wherein the time period for slow-release of the benzoxaborole treatment by the liquid-absorbing material is between over 12 hours to about 31 days.

143. The method of any one of clauses 81 to 142, wherein the plurality of chambers further comprises one or more apertures.

144. The method of clause 143, wherein the one or more apertures has a size between about 2 mm to about 2 cm.

145. The method of clause 143 or clause 144, wherein the one or more apertures is in a location on the chamber selected from the group consisting of the base, the lid, the sides, or a combination thereof.

146. The method of any one of clauses 143 to 145, wherein the one or more apertures enables introduction of the benzoxaborole treatment, the treatment carrier, or a combination thereof to the chamber.

147. The method of any one of clauses 143 to 145, wherein the one or more apertures enables release of the benzoxaborole treatment, the treatment carrier, or a combination thereof from the chamber.

148. The method of any one of clauses 81 to 147, wherein the food products are manually or robotically placed in the chamber.

149. The method of any one of clauses 81 to 148, wherein the food products are treated post-harvest.

150. The method of any one of clauses 81 to 149, wherein the distance between the food products and the plurality of chambers comprising the benzoxaborole treatment is no greater than 6 feet.

151. The method of any one of clauses 81 to 150, wherein the distance between the food products and the plurality of chambers comprising the benzoxaborole treatment is between about 0.1 inches and about 6 feet.

152. The method any one of clauses 81 to 151, wherein the one or more food products are treated for an initial time period ranging from about 12 hours to about 5 days.

153. The method of any one of clauses 81 to 152, wherein the benzoxaborole treatment concentration ranges from about 0.1 mg/chamber to about 10 mg/chamber.

154. The method of any one of clauses 81 to 153, wherein drying the one or more surfaces of the plurality of chambers occurs at room temperature, wherein room temperature is between about 21° C. and about 23° C.

155. The method of any one of clauses 81 to 154, wherein drying the one or more surfaces of the plurality of chambers occurs instantaneously or within seconds.

156. The method of any one of clauses 81 to 155, wherein drying the one or more surfaces of the plurality of chambers occurs instantaneously.

157. The method of any one of clauses 81 to 155, wherein drying the one or more surfaces of the plurality of chambers occurs within seconds.

158. The method of any one of clauses 81 to 155 or 157, wherein drying the one or more surfaces of the plurality of chambers occurs between about 0.1 seconds and about 60 seconds.

159. The method of any one of clauses 81 to 158, wherein the method results in greater uniformity and consistency in application of benzoxaborole treatment to the plurality of chambers.

160. The method of any one of clauses 81 to 159, wherein the method provides one month of extended antimicrobial protection to the treated food products.

The terms "chamber," "container," "material," or the phrase "packaging material" are interchangeable and refer to any material that is used to box, wrap, store, or package a food or food product, such as a plant, crop, or meat. A plurality of chambers comprises from about 1000 to tens of thousands to one or more millions of chambers.

The term "carrier" refers to a material, composition, or control, such as a liquid or solid filler, diluent, excipient, solvent, gas, or encapsulating material, involved in carrying or transporting an active ingredient, compound, analog, or derivative from one location to another location. A carrier must be acceptable in the sense of being compatible with the other ingredients of the formulation and not injurious to food, such as plant, crops, or meat products.

Exemplary embodiments of the compounds of the present disclosure are described herein. In some embodiments, the antimicrobial compound, sometimes called a benzoxaborole, comprises Compounds A, B, and/or C, which may encompass diastereomers and enantiomers of the illustrative compounds. Enantiomers are defined as one of a pair of molecular entities which are mirror images of each other and non-superimposable. Diastereomers or diastereoisomers are defined as stereoisomers other than enantiomers. Diastereomers or diastereoisomers are stereoisomers not related as mirror images. Diastereoisomers are characterized by differences in physical properties.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg, *Advanced Organic Chemistry* $4^{th}$ Ed., Vols. A (2000) and B (2001), Plenum Press, New York, N.Y.

As used herein, the phrase "moiety" refers to a specific segment or functional group of a molecule. Chemical moieties are often recognized chemical entities embedded in or appended to a molecule.

As used herein, the phrases "heteroatom" and "hetero-" refer to atoms other than carbon (C) and hydrogen (H). Examples of heteroatoms include oxygen (O), nitrogen (N) sulfur (S), silicon (Si), germanium (Ge), aluminum (Al) and boron (B).

As used herein, the phrases "halo" and "halogen" are interchangeable and refer to fluoro (—F), chloro (—Cl), bromo (—Br), and iodo (—I).

As used herein, the phrase "alkyl" refers to an unsubstituted or substituted, hydrocarbon group and can include straight, branched, cyclic, saturated and/or unsaturated features. Although the alkyl moiety may be an "unsaturated alkyl" moiety, which means that it contains at least one alkene or alkyne moiety, typically, the alkyl moiety is a "saturated alkyl" group, which means that it does not contain any alkene or alkyne moieties. Likewise, although the alkyl moiety may be cyclic, the alkyl moiety typically is acyclic group. Thus, in some embodiments, "alkyl" refers to an optionally substituted straight-chain, or optionally substituted branched-chain saturated hydrocarbon monoradical having from about one to about thirty carbon atoms in some embodiments, from about one to about fifteen carbon atoms in some embodiments, and from about one to about six carbon atoms in further embodiments. Examples of saturated alkyl radicals include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, sec-butyl, tert-butyl, n-pentyl, isopentyl, neopentyl, and n-hexyl, and longer alkyl groups, such as heptyl, and octyl. It should be noted that whenever it appears herein, a numerical range such as "1 to 6" refers to each integer in the given range; e.g., "1 to 6 carbon atoms" or "$C_{1-6}$" or "$C_1-C_6$" means that the alkyl group may consist of 1 carbon atom, 2 carbon atoms, 3 carbon atoms, 4 carbon atoms, 5 carbon atoms, and/or 6 carbon atoms, although the present definition also covers the occurrence of the term "alkyl" where no numerical range is designated.

As used herein, the phrase "substituted alkyl" refers to an alkyl group, as defined herein, in which one or more (up to about five, preferably up to about three) hydrogen atoms is replaced by a substituent independently selected from the substituent group defined herein.

As used herein, the phrases "substituents" and "substituted" refer to groups which may be used to replace another group on a molecule. Such groups are known to those of skill in the chemical arts and may include, without limitation, one or more of the following independently selected groups, or designated subsets thereof: halogen, —CN, —OH, —$NO_2$, —$N_3$, =O, =S, =NH, —$SO_2$, —$NH_2$, —COOH, nitroalkyl, amino, including mono- and di-substituted amino groups, cyanato, isocyanato, thiocyanato, isothiocyanato, guanidinyl, O-carbamyl, N-carbamyl, thiocarbamyl, uryl, isouryl, thiouryl, isothiouryl, mercapto, sulfanyl, sulfinyl, sulfonyl, sulfonamidyl, phosphonyl, phosphatidyl, phosphoramidyl, dialkylamino, diarylamino, diarylalkylamino; and the protected compounds thereof. The protecting groups that may form the protected compounds of the above substituents are known to those of skill in the art and may be found in references such as Greene and Wuts, *Protective Groups in Organic Synthesis*, 3rd ed.; John Wiley & Sons, New York, N.Y. (1999) and Kocienski, *Protective Groups*; Thieme Verlag, New York, N.Y. (1994) which are incorporated herein by reference in their entirety.

As used herein, the phrase "alkoxy" refers to the group —O-alkyl, where alkyl is as defined herein. In one embodiment, alkoxy groups include, e.g., methoxy, ethoxy, n-propoxy, isopropoxy, n-butoxy, tert-butoxy, sec-butoxy, n-pentoxy, n-hexoxy, 1,2-dimethylbutoxy, and the like. The alkoxy can be unsubstituted or substituted.

As used herein, the phrases "cyclic" and "membered ring" refer to any cyclic structure, including alicyclic, heterocyclic, aromatic, heteroaromatic and polycyclic fused or non-fused ring systems as described herein. The term "membered" is meant to denote the number of skeletal atoms that constitute the ring. Thus, for example, pyridine, pyran, and pyrimidine are six-membered rings and pyrrole, tetrahydrofuran, and thiophene are five-membered rings.

As used herein, the phrase "aromatic" refers to a cyclic or polycyclic moiety having a conjugated unsaturated $(4n+2)\pi$ electron system (where n is a positive integer), sometimes referred to as a delocalized $\pi$ electron system.

As used herein, the phrase "aryl" refers to an optionally substituted, aromatic, cyclic, hydrocarbon monoradical of from six to about twenty ring atoms, preferably from six to about ten carbon atoms and includes fused (or condensed) and non-fused aromatic rings. A fused aromatic ring radical contains from two to four fused rings where the ring of attachment is an aromatic ring, and the other individual rings within the fused ring may be cycloalkyl, cycloalkenyl, cycloalkynyl, heterocycloalkyl, heterocycloalkenyl, heterocycloalkynyl, aromatic, heteroaromatic or any combination thereof. A non-limiting example of a single ring aryl group includes phenyl; a fused ring aryl group includes naphthyl, anthryl, azulenyl; and a non-fused bi-aryl group includes biphenyl.

As used herein, the phrase "substituted aryl" refers to an aryl group, as defined herein, in which one or more (up to about five, preferably up to about three) hydrogen atoms is replaced by a substituent independently selected from the group defined herein, (except as otherwise constrained by the definition for the aryl substituent).

As used herein, the phrase "heteroaryl" refers to an optionally substituted, aromatic, cyclic monoradical containing from about five to about twenty skeletal ring atoms, preferably from five to about ten ring atoms and includes fused (or condensed) and non-fused aromatic rings, and which have one or more (one to ten, preferably about one to about four) ring atoms selected from an atom other than carbon (i.e., a heteroatom) such as, for example, oxygen, nitrogen, sulfur, selenium, phosphorus or combinations thereof. The term heteroaryl includes optionally substituted fused and non-fused heteroaryl radicals having at least one heteroatom. A fused heteroaryl radical may contain from two to four fused rings where the ring of attachment is a heteroaromatic ring and the other individual rings within the fused ring system may be alicyclic, heterocyclic, aromatic, heteroaromatic or any combination thereof. The term heteroaryl also includes fused and non-fused heteroaryls having from five to about twelve skeletal ring atoms, as well as those having from five to about ten skeletal ring atoms. Examples of heteroaryl groups include, but are not limited to, acridinyl, benzo[1,3]dioxole, benzimidazolyl, benzindazolyl, benzoisooxazolyl, benzokisazolyl, benzofuranyl, benzofurazanyl, benzopyranyl, benzothiadiazolyl, benzothiazolyl, benzo[b]thienyl, benzothiophenyl, benzothiopyranyl, benzotriazolyl, benzoxazolyl, carbazolyl, carbolinyl, chromenyl, cinnolinyl, furanyl, furazanyl, furopyridinyl, furyl, imidazolyl, indazolyl, indolyl, indolidinyl, indolizinyl, isobenzofuranyl, isoindolyl, isoxazolyl, isoquinolinyl, isothiazolyl, naphthylidinyl, naphthyridinyl, oxadiazolyl, oxazolyl, phenoxazinyl, phenothiazinyl, phenazinyl, phenoxathiynyl, thianthrenyl, phenathridinyl, phenathrolinyl, phthalazinyl, pteridinyl, purinyl, puteridinyl, pyrazyl, pyrazolyl, pyridyl, pyridinyl, pyridazinyl, pyrazinyl, pyrimidinyl, pyrimidyl, pyrrolyl, quinazolinyl, quinolinyl, quinoxalinyl, tetrazolyl, thiadiazolyl, thiazolyl, thienyl, triazinyl, (1,2,3,)- and (1,2,4)-triazolyl and the like, and their oxides where appropriate, such as for example pyridyl-N-oxide.

As used herein, the phrase "substituted heteroaryl" refers to a heteroaryl group, as defined herein, in which one or more (up to about five, preferably up to about three) hydrogen atoms is replaced by a substituent independently selected from the group defined herein.

As used herein, the phrase "leaving group" refers to a group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like. In some embodiments, a leaving group can be HC(O)—COOH or RC(O)—COOH, wherein R is a $C_1$-$C_6$ alkyl or substituted $C_1$-$C_6$ alkyl.

The compounds of the invention as described herein may be synthesized using standard synthetic techniques known to those of skill in the art or using methods known in the art in combination with methods described herein. The starting materials used for the synthesis of the compounds of the invention as described herein, can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, *Advanced Organic Chemistry* 4th Ed. (1992) John Wiley & Sons, New York, N.Y.; Carey and Sundberg, *Advanced Organic Chemistry* 4th Ed., Vols. A (2000) and B (2001) Plenum Press, New York, N.Y. and Greene and Wuts, *Protective Groups in Organic Synthesis*, 3rd Ed. (1999) John Wiley & Sons, New York, N.Y., (all of which are incorporated by reference in their entirety). General methods for the preparation of compounds as disclosed herein may be derived from known reactions in the field, and the reactions may be modified by the use of appropriate reagents and conditions, as would be recognized by the skilled person, for the introduction of the various moieties found in the formulae as provided herein. For example, the compounds described herein can be modified using various electrophiles or nucleophiles to form new functional groups or substituents.

The terms "food" or "food product" refer to a plant or plant parts.

The term "plant(s)" and "plant parts" include, but not limited to, plant tissues, such as leaves, calli, stems, roots, flowers, fruits, vegetables, pollen, and seeds. A class of plants that may be used in the present invention is generally as broad as the class of higher and lower plants including, but not limited to, dicotyledonous plants, monocotyledonous plants, and plant crops, including, but not limited to, vegetable crops, fruit crops, ornamental crops, and meats.

"Vegetable crops" include, but are not limited to, asparagus, beet (e.g., sugar beet and fodder beet), beans, broccoli, cabbage, carrot, cassava, cauliflower, celery, cucumber, eggplant, garlic, gherkin, leafy greens (lettuce, kale, spinach, and other leafy greens), leek, lentils, mushroom, onion, peas, pepper (e.g., sweet peppers, bell peppers, and hot peppers), potato, pumpkin, sweet potato, snap bean, squash, tomato, and turnip.

"Fruit crops" include, but are not limited to, apple, avocado, banana, soft fruits, such as, strawberry, blueberry, raspberry, blackberry, cranberry, currents and other types of soft fruit berries, carambola, cherry, citrus (e.g., oranges, lemon, lime, mandarin, grapefruit, and other citrus), coconut, fig, grapes, guava, kiwifruit, mango, nectarine, melons (including cantaloupe, muskmelon, watermelon, and other melons), olive, papaya, passionfruit, peach, pear, persimmon, pineapple, plum, and pomegranate. More specifically, horticultural crops of the present disclosure include, but are not limited to, soft fruits (e.g., grape, apple, pear, and persimmon) and berries (e.g., strawberries, blackberries, blueberries, and raspberries).

"Ornamental crops" include, but are not limited to, baby's breath, carnation, dahlia, daffodil, geranium, gerbera, lily, orchid, peony, Queen Anne's lace, rose, snapdragon, or other cut-flowers or ornamental flowers, potted flowers, flower bulbs, shrub, and deciduous or coniferous tree.

"Meat" or "Meats" include, but are not limited to beef, bison, chicken, deer, goat, turkey, pork, sheep, fish, shellfish, mollusks, or dry-cured meat products.

The term "subliming" refers the ability of a chemical, compound, or composition or other solid substance to evaporate or to disperse into vapor or gas when heated. Often the substance can transition back to a solid upon cooling.

The term "vaporizing" refers to transitioning or converting into vapor.

The term "volatile" or "volatilizes" refers to the ability of a chemical, compound, or composition or other substance to evaporate or to disperse into vapor or gas.

Compounds and Components of the Present Methods

The methods of the present disclosure are directed to treating food packaging materials or containers with one or more volatile antimicrobial compounds. More specifically, the methods described herein provide for coating benzoxaborole compounds on surfaces of food packaging materials or containers in order to delay or inhibit microorganism growth and food decay. Accordingly, the methods of the present disclosure comprise, consist of, or consist essentially of benzoxaborole compounds.

Exemplary embodiments of the compounds of the present disclosure are described herein. In some embodiments, the antimicrobial compound, sometimes called a benzoxabroole, comprises Compounds A, B, or C, which may encompass diastereomers and enantiomers of the illustrative compounds. Enantiomers are defined as one of a pair of molecular entities which are mirror images of each other and non-superimposable. Diastereomers or diastereoisomers are defined as stereoisomers other than enantiomers. Diastereomers or diastereoisomers are stereoisomers not related as mirror images. Diastereoisomers are characterized by differences in physical properties.

One exemplary embodiment of a benzoxaborole compound of the present method is Compound A:

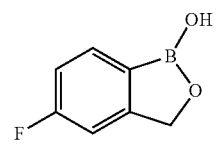

or an analog or derivative thereof.

An additional illustrative embodiment of a benzoxaborole compound of the present method is Compound B:

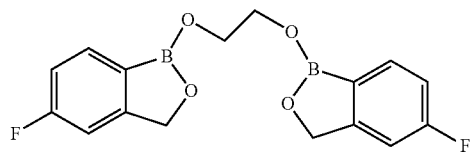 [SMILES: Fc1ccc2c(c1)COB2OCCOB1OCc2cc(F)ccc21]

or an analog or derivative thereof.

Another exemplary embodiment of a benzoxaborole compound of the present method is Compound C, which is a salt version of Compounds A and/or B:

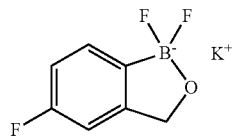 [SMILES: Fc1ccc2c(c1)CO[B-]2(F)F ; [K+]]

or an analog or derivative thereof.

In some other exemplary embodiments, the benzoxaborole, sometimes called a volatile antimicrobial compound, of the invention has a structure of formula (I), (II), or (III):

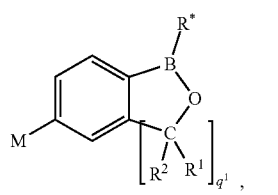
(I)

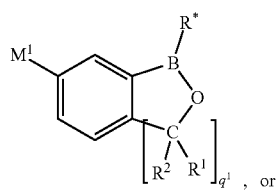
(II)

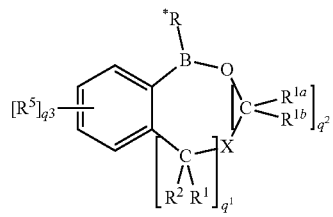

wherein q1 and q2 are independently 1, 2, or 3;
q3=0, 1, 2, 3, or 4;
M is hydrogen, halogen, —OCH$_3$, or —CH$_2$—O—CH$_2$—O—CH$_3$;
M$^1$ is halogen, —CH$_2$OH, or —OCH$_3$;
X is O, S, or NR$^{1c}$, wherein R$^{1c}$ is hydrogen, substituted alkyl, or unsubstituted alkyl;
R$^1$, R$^{1a}$, R$^{1b}$, R$^2$, and R$^5$ are independently hydrogen, OH, NH$_2$, SH, CN, NO$_2$, SO$_2$, OSO$_2$OH, OSO$_2$NH$_2$, substituted or unsubstituted cycloalkyl, substituted or unsubstituted heterocycloalkyl, substituted or unsubstituted aryl, or substituted or unsubstituted heteroaryl;

R* is substituted or unsubstituted aryl, substituted or unsubstituted arylalkyl, substituted or unsubstituted heteroaryl, substituted or unsubstituted heteroarylalkyl, or substituted or unsubstituted vinyl;
with a proviso that when M is F, R* is not a member selected from:

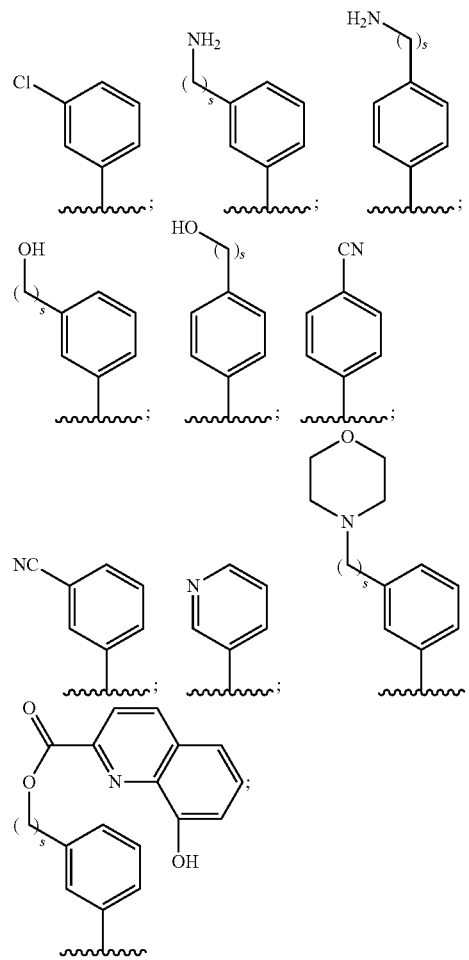

and with a proviso that when M is Cl, R* is not a member selected from:

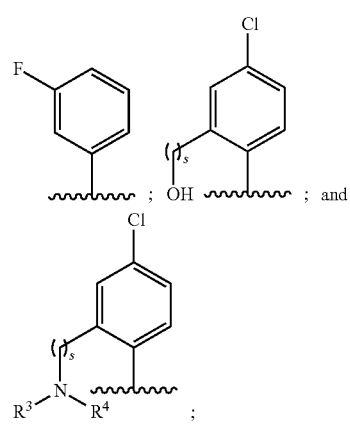

and with a proviso that when M is hydrogen, R* is not a member selected from:

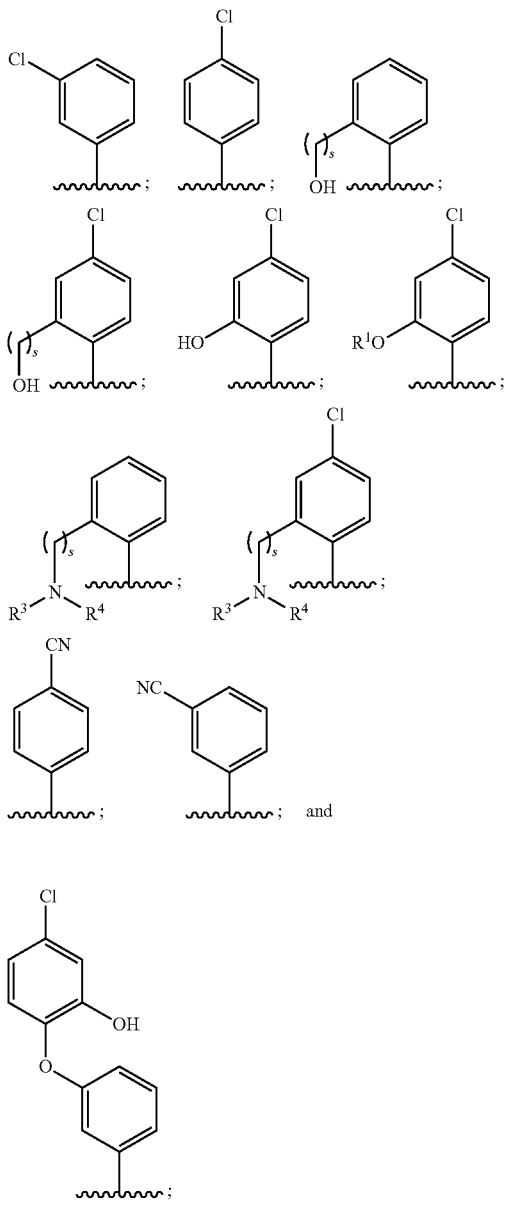

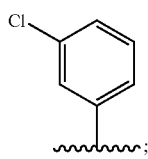

wherein s=1 or 2; and $R^3$ and $R^4$ are independently methyl or ethyl;

and with a provision that when M is $OCH_3$, R* is not a member selected from:

and with a provision that when $M^1$ is F, R* is not a member selected from:

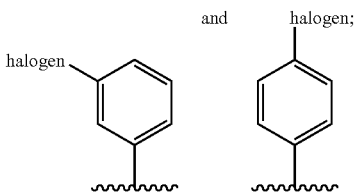

and pharmaceutically acceptable salts thereof.

In one embodiment, the R* has a structure selected from:

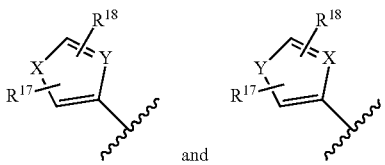

wherein X is a member selected from CH=CH, N=CH, $NR^{14}$, O and S;

wherein $R^{14}$ is a member selected from H, substituted or unsubstituted alkyl, substituted or unsubstituted aryl and substituted or unsubstituted arylalkyl;

Y is a member selected from CH and N;

$R^{17}$ and $R^{18}$ are members independently selected from H, substituted or unsubstituted alkyl, substituted or unsubstituted aryl, substituted or unsubstituted arylalkyl, $(CH_2)_vOH$, $(CH_2)_wNR^{15}R^{16}$, $CO_2H$, $CO_2$-alkyl, $CONH_2$, S-alkyl, S-aryl, SO-alkyl, SO-aryl, $SO_2$-alkyl, $SO_2$-aryl, $SO_2H$, $SCF_2$, CN, halogen, $CF_3$ and $NO_2$;

wherein $R^{15}$ and $R^{16}$ are members independently selected from hydrogen, substituted or unsubstituted alkyl and substituted or unsubstituted alkanoyl;

v=1, 2, or 3; and w=0, 1, 2, or 3.

In another embodiment, the R* has the following structure:

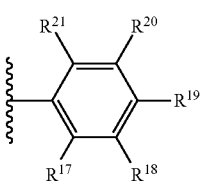

wherein $R^{17}$, $R^{18}$, $R^{19}$, $R^{20}$, and $R^{21}$ are independently selected from H, substituted or unsubstituted alkyl, substituted or unsubstituted aryl, substituted or unsubstituted arylalkyl, substituted or unsubstituted alkyloxy, substituted or unsubstituted aryloxy, substituted or unsubstituted oxazolidin-2-yl, $(CH_2)_tOH$, $CO_2H$, $CO_2$-alkyl, $CONH_2$, CONH-alkyl, $CON(alkyl)_2$, OH, SH, S-alkyl, S-aryl, SO-alkyl, SO-aryl, $SO_2$-alkyl, $SO_2$-aryl, $SO_2H$, $SCF_3$, CN, halogen, $CF_3$, $NO_2$, $(CH_2)_u NR^{22}R^{23}$, $SO_2NH_2$, $OCH_2CH_2NH_2$, $OCH_2CH_2NH$-alkyl and $OCH_2CH_2N(alkyl)_2$;

wherein t=1, 2 or 3;

u=0, 1, or 2;

$R^{22}$ and $R^{23}$ are independently selected from H, substituted or unsubstituted alkyl, and substituted or unsubstituted alkanoyl.

In another embodiment, the R* has the following structure:

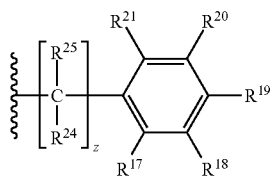

wherein $R^{17}$, $R^{18}$, $R^{19}$, $R^{20}$, and $R^{21}$ are independently selected from H, substituted or unsubstituted alkyl, substituted or unsubstituted aryl, substituted or unsubstituted arylalkyl, substituted or unsubstituted alkyloxy, substituted or unsubstituted aryloxy, substituted or unsubstituted oxazolidin-2-yl, $(CH_2)_tOH$, $CO_2H$, $CO_2$-alkyl, $CONH_2$, CONH-alkyl, $CON(alkyl)_2$, OH, SH, S-alkyl, S-aryl, SO-alkyl, SO-aryl, $SO_2$-alkyl, $SO_2$-aryl, $SO_2H$, $SCF_3$, CN, halogen, $CF_3$, $NO_2$, $(CH_2)_uNR^{22}R^{23}$, $SO_2NH_2$, $OCH_2CH_2NH_2$, $OCH_2CH_2NH$-alkyl and $OCH_2CH_2N(alkyl)_2$;

wherein t=1, 2 or 3;
u=0, 1, or 2;
$R^{22}$ and $R^{23}$ are independently selected from H, substituted or unsubstituted alkyl, and substituted or unsubstituted alkanoyl;
$R^{24}$ and $R^{25}$ are independently selected from H, substituted or unsubstituted alkyl, substituted or unsubstituted aryl, substituted or unsubstituted arylalkyl, substituted or unsubstituted alkyloxy, substituted or unsubstituted aryloxy, substituted or unsubstituted oxazolidin-2-yl, $(CH_2)_tOH$, $CO_2H$, $CO_2$-alkyl, $CONH_2$, CONH-alkyl, $CON(alkyl)_2$, OH, SH, S-alkyl, S-aryl, SO-alkyl, SO-aryl, $SO_2$-alkyl, $SO_2$-aryl, $SO_3H$, $SCF_3$, CN, halogen, $CF_3$, $NO_2$, $(CH_2)_uNR^{22}R^{23}$, $SO_2NH_2$, $OCH_2CH_2NH_2$, $OCH_2CH_2NH$-alkyl and $OCH_2CH_2N(alkyl)_2$;
Z=1, 2, 3, 4, 5, or 6.

Additional antimicrobial compounds are also disclosed previously in U.S. Pat. No. 8,106,031, and International Patent Application WO 2007/131072A2, the contents of which are hereby incorporated by reference in their entireties.

In some embodiments, the volatile antimicrobial compound of the invention has the structure of formula (IV):

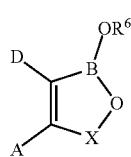

(IV)

wherein A and D together with the carbon atoms to which they are attached form a 5-, 6-, or 7-membered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings;
X is a group —$CR^7R^8$ wherein $R^7$ and $R^8$ are each independently hydrogen, $C_1$-$C_6$-alkyl, nitrile, nitro, aryl, arylalkyl or $R^7$ and $R^8$ together with the carbon atom to which they are attached form an alicyclic ring; and
$R^6$ is hydrogen, $C_1$-$C_{18}$-alkyl, $C_1$-$C_{18}$-alkyl substituted by $C_1$-$C_6$-alkoxy, $C_1$-$C_6$-alkylthio, hydroxy, amino, amino substituted by $C_1$-$C_{18}$-alkyl, carboxy, aryl, aryloxy, carbonamido, carbonamido substituted by $C_1$-$C_6$-alkyl, aryl or arylalkyl, arylalkyl, aryl, heteroaryl, cycloalkyl, $C_1$-$C_{18}$-alkyleneamino, $C_1$-$C_{18}$-alkyleneamino substituted by phenyl, $C_1$-$C_6$-alkoxy or $C_1$-$C_6$-alkylthio, carbonyl alkyleneamino or a radical of formula (V):

(V)

wherein A, D and X are as defined herein before except for boronophthalide;
and pharmaceutically acceptable salts thereof.

In one embodiment, the volatile antimicrobial compound of the invention has the structure of formula (IX):

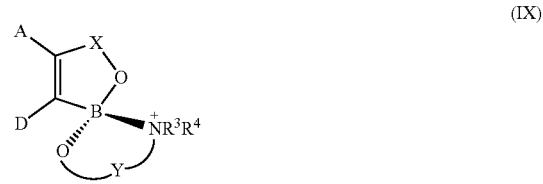

(IX)

wherein A, D, and X are defined as above;
Y is a divalent alkylene linking group containing up to 18 carbon atoms or a divalent alkylene linking group containing up to 18 carbon atoms which is substituted by phenyl, $C_1$-$C_6$ alkoxy, $C_1$-$C_6$-alkylthio; carbonyl alkylene amino; and
$R^3$ and $R^4$ are each, independently, hydrogen, $C_1$-$C_{18}$-alkyl or phenyl or $R^3$ together with Y or part of Y forms a 5-, 6- or 7-membered ring containing the nitrogen atom.

In another embodiment, the volatile antimicrobial compound of the invention has the structure of formula (X):

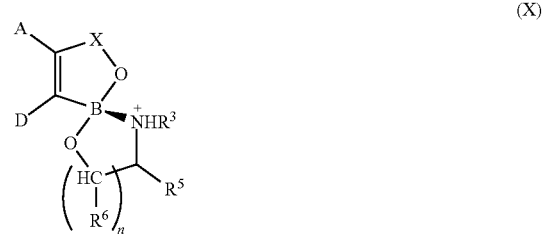

(X)

wherein A, D, and X are defined as above;
n is 1, 2, or 3;
$R^3$ is hydrogen, $C_1$-$C_{18}$-alkyl or phenyl; and
$R^5$ and $R^6$ are each, independently, hydrogen, alkyl containing up to a total of 16 carbon atoms or phenyl.

Additional antimicrobial compounds are also disclosed previously in U.S. Pat. No. 5,880,188, the content of which is hereby incorporated by reference in its entirety.

In another aspect, the volatile antimicrobial compound of the invention has the structure of formula (VI):

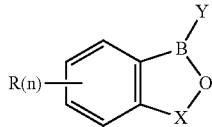

(VI)

wherein each R is independently hydrogen, alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, halogen, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

n=1, 2, 3, or 4;

B is boron;

X=(CR$_2$)$_m$ where m=1, 2, 3, or 4;

Y is alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

with a proviso that R is not aryloxy or heteroaryloxy when Y is hydroxyl;

and pharmaceutically acceptable salts thereof.

In one embodiment, the volatile antimicrobial compound has a structure of formula (VII):

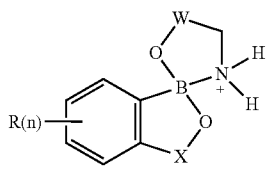

(VII)

wherein W=(CH$_2$)$_q$ where q is 1, 2, or 3.

In another embodiment, the volatile antimicrobial compound has a structure of

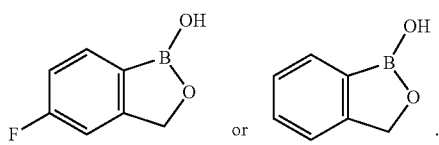 [SMILES: OB1OCc2cc(F)ccc21 ; OB1OCc2ccccc21]

In another embodiment, the volatile antimicrobial compound of the invention has the structure of formula (VIII):

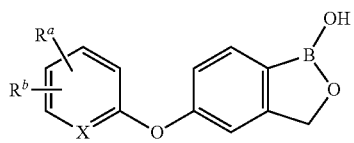

(VIII)

wherein R$^a$ is CN, C(O)NR$^9$R$^{10}$, or C(O)OR$^{11}$ wherein R$^{11}$ is hydrogen, substituted alkyl, or unsubstituted alkyl, X is N, CH and CR$^b$;

R$^b$ is halogen, substituted or unsubstituted alkyl, C(O)R$^{12}$, C(O)OR$^{12}$, OR$^{12}$, NR$^{12}$R$^{13}$, wherein R$^9$, R$^{10}$, R$^{12}$, and R$^{13}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

with a proviso that R$^9$ and R$^{10}$, together with the atoms to which they are attached, are optionally combined to form a 4- to 8-membered substituted or unsubstituted heterocycloalkyl ring;

and with a proviso that R$^{12}$ and R$^{13}$, together with the atoms to which they are attached, are optionally combined to form a 4- to 8-membered substituted or unsubstituted heterocycloalkyl ring;

and pharmaceutically acceptable salts thereof.

In one embodiment, the volatile antimicrobial compound of the invention has the structure of formula (XI):

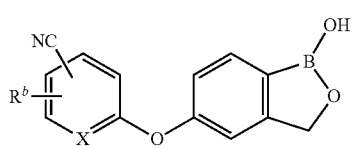

(XI)

In another embodiment, the volatile antimicrobial compound of the invention is selected from:

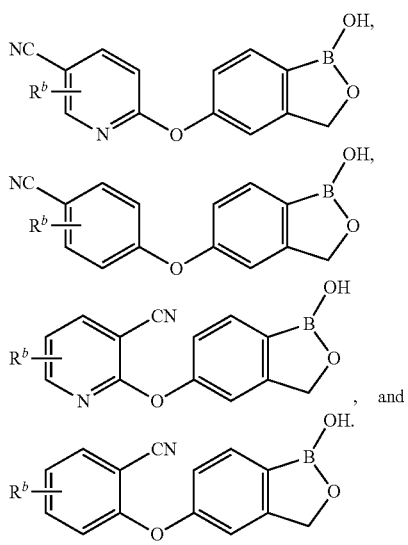

In another embodiment, the volatile antimicrobial compound of the invention is selected from:

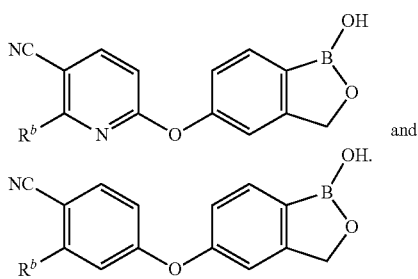

In another embodiment, the volatile antimicrobial compound of the invention is selected from:

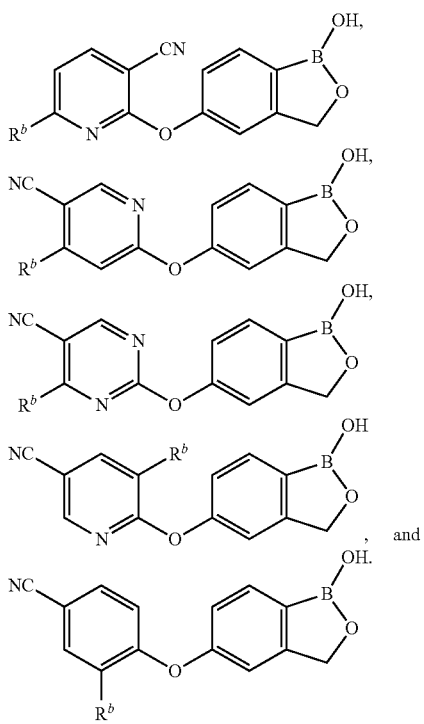

In one embodiment, the volatile antimicrobial compound of the invention has the structure of formula (XII):

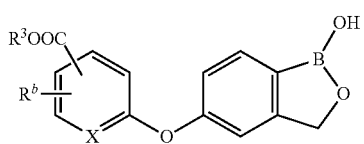

In another embodiment, the volatile antimicrobial compound of the invention is selected from:

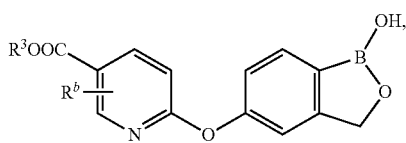

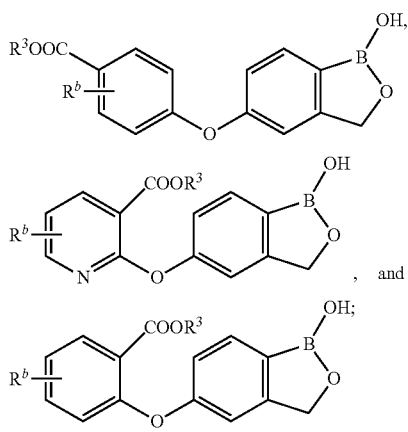

wherein $R^3$ is hydrogen, substituted or unsubstituted alkyl, or substituted or unsubstituted heteroalkyl.

In another embodiment, the volatile antimicrobial compound of the invention is selected from:

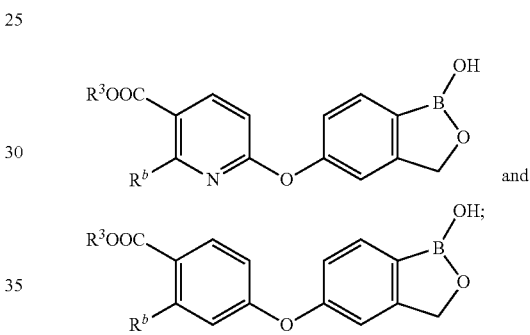

wherein $R^3$ is hydrogen, substituted or unsubstituted alkyl, or substituted or unsubstituted heteroalkyl.

In another embodiment, the volatile antimicrobial compound of the invention is selected from:

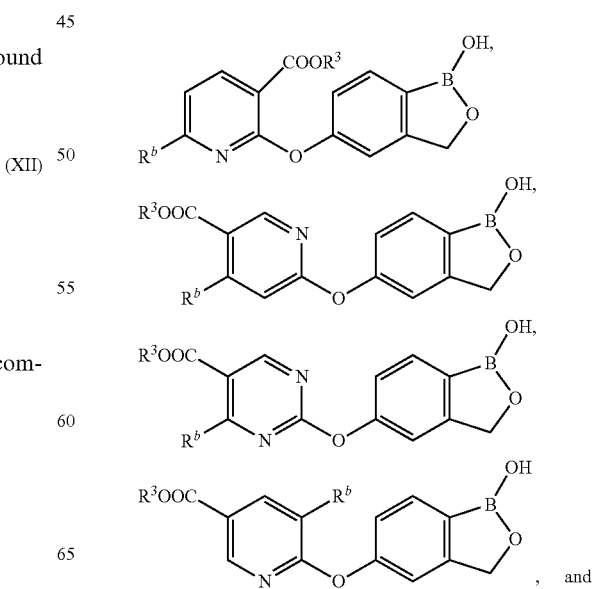

-continued

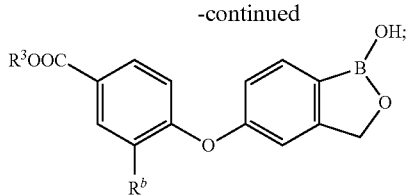

wherein $R^3$ is hydrogen, substituted or unsubstituted alkyl, or substituted or unsubstituted heteroalkyl.

In one embodiment, the volatile antimicrobial compound of the invention has the structure of formula (XIII):

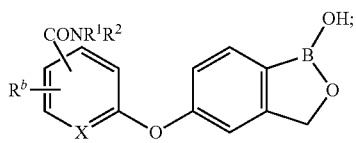

(XIII)

wherein each of $R^1$ and $R^2$ is independently hydrogen, substituted or unsubstituted alkyl, or substituted or unsubstituted heteroalkyl.

In another embodiment, the volatile antimicrobial compound of the invention is selected from:

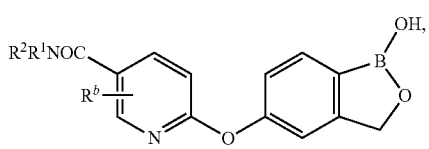

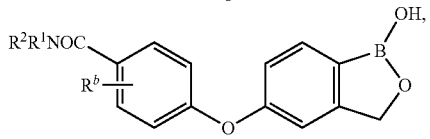

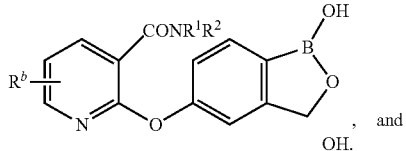

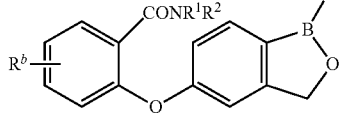

In another embodiment, the volatile antimicrobial compound of the invention is selected from:

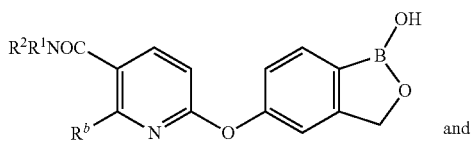

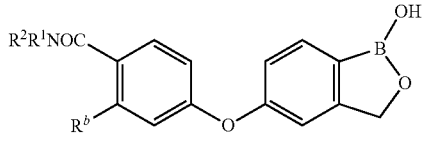

wherein each of $R^1$ and $R^2$ is independently hydrogen, substituted or unsubstituted alkyl, or substituted or unsubstituted heteroalkyl.

In another embodiment, the volatile antimicrobial compound of the invention is selected from:

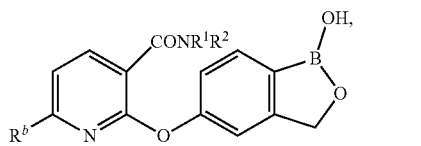

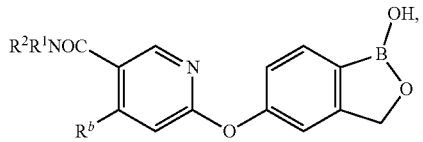

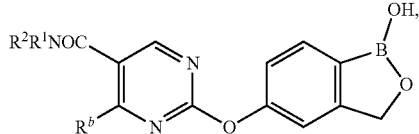

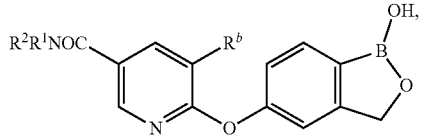

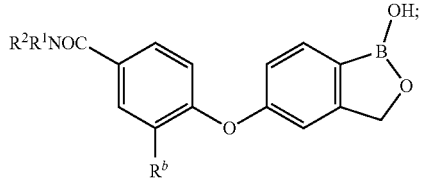

wherein each of $R^1$ and $R^2$ is independently hydrogen, substituted or unsubstituted alkyl, or substituted or unsubstituted heteroalkyl.

In one embodiment, $R^b$ is selected from fluorine and chlorine. In another embodiment, $R^b$ is selected from $OR^{26}$ and $NR^{27}R^{28}$. In another embodiment when $R^b$ is $OR^{26}$, $R^{26}$ is selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In another embodiment when $R^b$ is $OR^{26}$, $R^{26}$ is selected from H, substituted or unsubstituted alkyl, substituted or unsubstituted heteroalkyl and substituted or unsubstituted cycloalkyl. In another embodiment when $R^b$ is $OR^{26}$, $R^{26}$ is unsubstituted $C_1$-$C_6$ alkyl. In another embodiment when $R^b$ is $OR^{26}$, $R^{26}$ is unsubstituted cycloalkyl. In another embodiment when $R^b$ is $OR^{26}$, $R^{26}$ is alkyl, substituted with a member selected from substituted or unsubstituted $C_1$-$C_6$ alkoxy. In another embodiment when $R^b$ is $OR^{26}$, $R^{26}$ is alkyl, substituted with at least one halogen. In another embodiment when $R^b$ is $OR^{26}$, $R^{26}$ is alkyl, substituted with at least one oxo moiety.

In another embodiment when $R^b$ is $OR^{26}$, $R^{26}$ is a member selected from —$CH_3$, —$CH_2CH_3$, —$(CH_2)_2CH_3$, —$CH(CH_3)_2$, —$CH_2CF_3$, —$CH_2CHF_2$, —$CH_2CH_2(OH)$, —$CH_2CH_2(OCH_3)$, —$CH_2CH_2(OC(CH_3)_3)$, —$C(O)CH_3$, —$CH_2CH_2OC(O)CH_3$, —$CH_2C(O)OCH_2CH_3$, —$CH_2C(O)OC(CH_3)_3$, —$(CH_2)_3C(O)CH_3$, —$CH_2C(O)OC(CH_3)_3$, cyclopentyl, cyclohexyl,

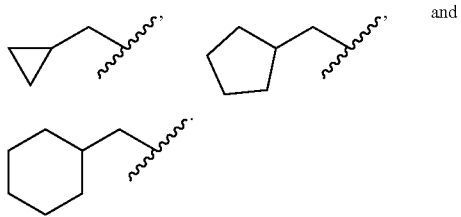

In another embodiment when $R^b$ is $NR^{27}R^{28}$, $R^{27}$ and $R^{28}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In another embodiment when $R^b$ is $NR^{27}R^{28}$, $R^{27}$ is H or unsubstituted alkyl; and $R^{28}$ is unsubstituted alkyl or alkyl substituted with a member selected from hydroxyl, phenyl, unsubstituted alkoxy and alkoxy substituted with a phenyl. In a further embodiment when $R^b$ is $NR^{27}R^{28}$, $R^{27}$ is H or $CH_3$.

In another embodiment when $R^b$ is $NR^{27}R^{28}$, $R^{27}$ and $R^{28}$ are independently selected from substituted or unsubstituted alkyl. In another embodiment when $R^b$ is $NR^{27}R^{28}$, $R^{27}$ is unsubstituted alkyl; and $R^{28}$ is substituted or unsubstituted alkyl. In another embodiment when $R^b$ is $NR^{27}R^{28}$, $R^{27}$ is unsubstituted alkyl; and $R^{28}$ is alkyl, substituted with a member selected from substituted or unsubstituted alkoxy and hydroxyl. In another embodiment when $R^b$ is $NR^{27}R^{28}$, $R^{27}$ is unsubstituted alkyl; and $R^{28}$ is alkyl, substituted with unsubstituted alkoxy. In another embodiment when $R^b$ is $NR^{27}R^{28}$, $R^{27}$ is unsubstituted alkyl; and $R^{28}$ is alkyl, substituted with alkoxy, substituted with phenyl. In another embodiment when $R^b$ is $NR^{27}R^{28}$, $R^{27}$ is unsubstituted alkyl; and $R^{28}$ is alkyl, substituted with unsubstituted alkoxy. In another embodiment when $R^b$ is $NR^{27}R^{28}$, $R^{27}$ and $R^{28}$ together with the nitrogen to which they are attached, are combined to form a 4- to 8-membered substituted or unsubstituted heterocycloalkyl ring. In another embodiment when $R^b$ is $NR^{27}R^{28}$, $R^{27}$ and $R^{28}$ together with the nitrogen to which they are attached, are combined to form a 5- or 6-membered substituted or unsubstituted heterocycloalkyl ring.

In another embodiment, $R^b$ is selected from $N(CH_3)_2$, $N(CH_3)(CH_2CH_2(OCH_3))$, $N(CH_3)(CH_2CH_2OH)$, $NH_2$, $NHCH_3$, $NH(CH_2CH_2(OCH_3))$, $NH(CH_2CH_2(OCH_2Ph))$, $NH(CH_2Ph)$, $NH(C(CH_3)_3)$ and $NH(CH_2CH_2OH)$. In another embodiment, $R^b$ is selected from,

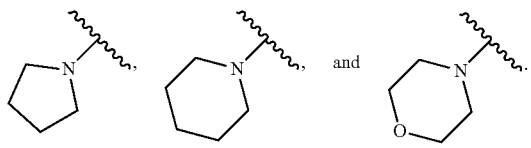 [SMILES: *N1CCCC1 ; *N1CCCCC1 ; *N1CCOCC1]

Additional antimicrobial compounds are also disclosed previously in U.S. Pat. No. 8,039,450, and patent application publication US 2009/0291917, the contents of which are hereby incorporated by reference in their entireties.

In one aspect, the volatile antimicrobial compound of the invention has the structure of formula (A):

$R^A-L^A-G-L^B-R^B$ (A), wherein
each of $R^A$ and $R^B$ is independently a radical comprising an oxaborole moiety;
each of $L^A$ and $L^B$ is independently —O— or

each of R and R' is independently hydrogen, unsubstituted or substituted $C_{1-18}$-alkyl, arylalkyl, aryl, or heterocyclic moiety; and
G is a substituted or unsubstituted $C_{1-18}$-alkylene, arylalkylene, arylene, or heterocyclic moiety; and pharmaceutically acceptable salts thereof.

In one embodiment, the volatile compound is an antimicrobial compound. In another embodiment, the volatile compound has use against pathogens affecting meats, plants, or plant parts, comprising contacting the meats, plants, or plant parts. In another embodiment, the $-L^A-G-L^B-$ portion of formula (A) is derived from a diol or diamine compound. In a further embodiment, the diol compound is selected from the group consisting of 1,2-ethylene glycol; 1,2-propylene glycol; 1,3-propylene glycol; 1,1,2,2-tetramethyl-1,2-ethylene glycol; 2,2-dimethyl-1,3-propylene glycol; 1,6-hexanediol; 1,10-decanediol; and combinations thereof. In another embodiment, the diamine compound is 1,2-ethylene diamine; 1,3-propylene diamine; or combinations thereof. In another embodiment, $L^A$ and $L^B$ are identical. In another embodiment, $L^A$ and $L^B$ are different. In another embodiment, each of $L^A$ and $L^B$ is independently —O— or —NH—. In another embodiment, $L^A$ and $L^B$ are identical. In another embodiment, $L^A$ and $L^B$ are different.

In another embodiment, the $-L^A-G-L^B-$ portion of formula (A) comprises asymmetrical functional groups (i.e., asymmetrical bridges). In a further embodiment, the $-L^A-G-L^B-$ portion of formula (A) comprises one hydroxyl group and one amine group. In a further embodiment, the $-L^A-G-L^B-$ portion of formula (A) comprises an amino alcohol. In another embodiment, G is a substituted or unsubstituted $C_{1-8}$-alkylene. In a further embodiment, G is a substituted or unsubstituted $C_{1-4}$-alkylene. In a further embodiment, G is selected from —$CH_2$—, —$CH_2$—$CH_2$—, and —$CH_2$—$CH_2$—$CH_2$—.

In another embodiment, each of $R^A$ and $R^B$ is independently derived from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof. In another embodiment, $R^A$ and $R^B$ are identical. In another embodiment, $R^A$ and $R^B$ are different.

In another embodiment, at least one of $R^A$ and $R^B$ is selected from formula (B), (C), or (D):

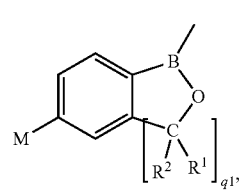

(B)

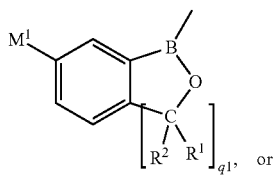
(C)

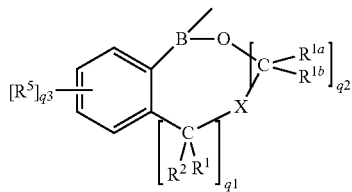
(D)

wherein q1 and q2 are independently 1, 2, or 3;
q3=0, 1, 2, 3, or 4;
B is boron;
M is hydrogen, halogen, —OCH$_3$, or —CH$_2$—O—CH$_2$—O—CH$_3$;
M$^1$ is halogen, —CH$_2$OH, or —OCH$_3$;
X is O, S, or NR$^{1c}$, wherein R$^{1c}$ is hydrogen, substituted alkyl, or unsubstituted alkyl;
R$^1$, R$^{1a}$, R$^{1b}$, R$^2$, and R$^5$ are independently hydrogen, OH, NH$_2$, SH, CN, NO$_2$, SO$_2$, OSO$_2$OH, OSO$_2$NH$_2$, substituted or unsubstituted cycloalkyl, substituted or unsubstituted heterocycloalkyl, substituted or unsubstituted aryl, or substituted or unsubstituted heteroaryl;
and pharmaceutically acceptable salts thereof.

Additional oxaborole moieties are also disclosed previously in U.S. Pat. No. 8,106,031, and International Patent Application WO 2007/131072A2, the contents of which are hereby incorporated by reference in their entireties.

In another embodiment, at least one of R$^A$ and R$^B$ has a structure of formula (F):

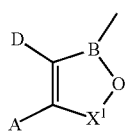
(F)

wherein A and D together with the carbon atoms to which they are attached form a 5, 6, or 7-membered fused ring which may be substituted by C$_{1-6}$-alkyl, C$_{1-6}$-alkoxy, hydroxy, halogen, nitro, nitrile, amino, amino substituted by one or more C$_{1-6}$-alkyl groups, carboxy, acyl, aryloxy, carbonamido, carbonamido substituted by C$_{1-6}$-alkyl, sulphonamido or trifluoromethyl or the fused ring may link two oxaborole rings; B is boron;
X$^1$ is a group —CR$^7$R$^8$ wherein R$^7$ and R$^8$ are each independently hydrogen, C$_{1-6}$-alkyl, nitrile, nitro, aryl, aralkyl or R$^7$ and R$^8$ together with the carbon atom to which they are attached form an alicyclic ring; and
and pharmaceutically acceptable salts thereof.

Additional oxaborole moieties are also disclosed previously in U.S. Pat. No. 5,880,188, the content of which is hereby incorporated by reference in its entirety.

In another embodiment, at least one of R$^A$ and R$^B$ is selected from formula (E) or (G):

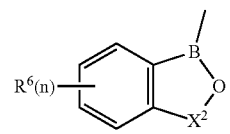
(E)

wherein each R$^6$ is independently hydrogen, alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, halogen, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;
n=1, 2, 3, or 4;
B is boron;
X$^2$=(CR$^{62}$)$_m$ where m=1, 2, 3, or 4; or

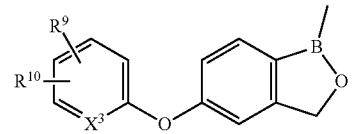
(G)

wherein R$^9$ is CN, C(O)NR$^{11}$R$^{12}$, or C(O)OR$^3$ wherein R$^3$ is hydrogen, substituted alkyl, or unsubstituted alkyl,
X$^3$ is N, CH and CR$^{10}$;
R$^{10}$ is halogen, substituted or unsubstituted alkyl, C(O)R$^{14}$, C(O)OR$^{14}$, OR$^{14}$, NR$^{14}$R$^{15}$, wherein each of R$^{11}$, R$^{12}$, R$^{14}$, and R$^{15}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
and pharmaceutically acceptable salts thereof.

In a further embodiment when at least one of R$^A$ and R$^B$ has a structure of formula (G), R$^9$ is CN and R$^{10}$ is R$^b$.

In another embodiment, at least one of R$^A$ and R$^B$ has a structure selected from:

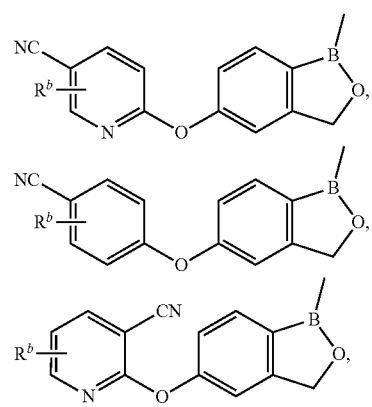

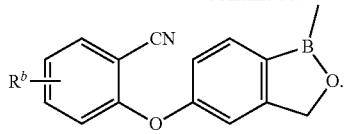

In another embodiment, at least one of $R^A$ and $R^B$ has a structure selected from:

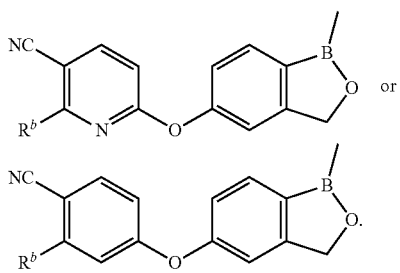

In another embodiment, at least one of $R^A$ and $R^B$ has a structure selected from:

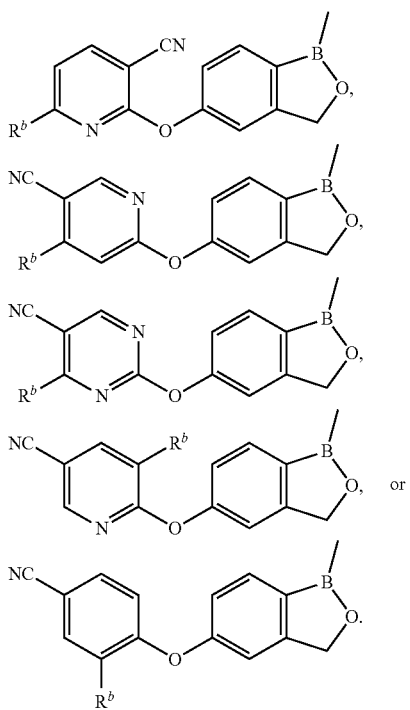

In another embodiment when at least one of $R^A$ and $R^B$ has a structure of formula (G), $R^9$ is —COOR$^3$ and $R^{10}$ is $R^b$.
In another embodiment, at least one of $R^A$ and $R^B$ has a structure selected from:

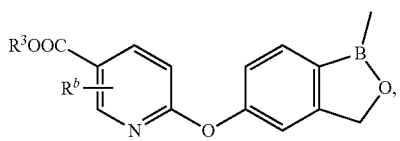

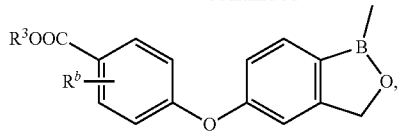

In another embodiment, at least one of $R^A$ and $R^B$ has a structure selected from:

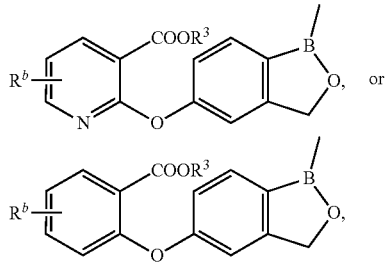

In another embodiment, at least one of $R^A$ and $R^B$ has a structure selected from:

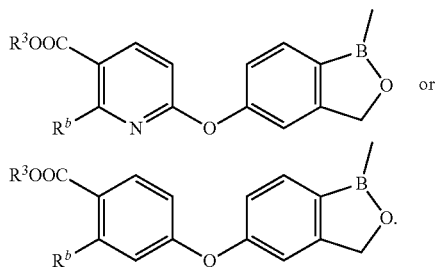

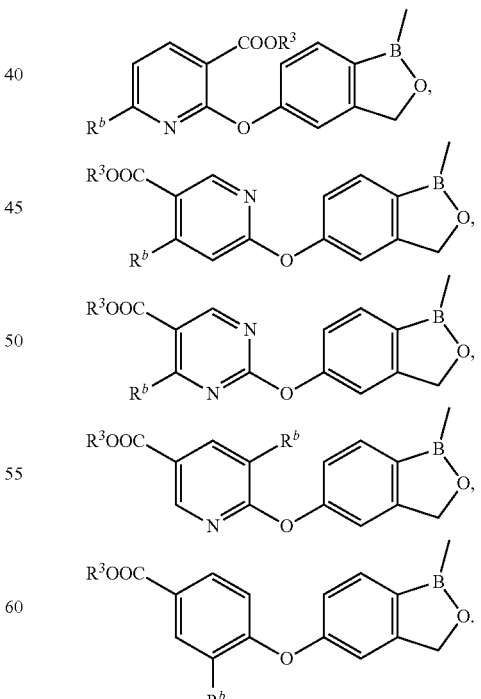

In another embodiment when at least one of $R^A$ and $R^B$ has a structure of formula (G), $R^9$ is —CONR$^1$R$^2$ and $R^{10}$ is $R^b$.

In another embodiment, each of $R^A$ and $R^B$ is independently selected from formula (B), (C), (D), (E), (F), or (G).

In another embodiment, the volatile compound of the invention is selected from:

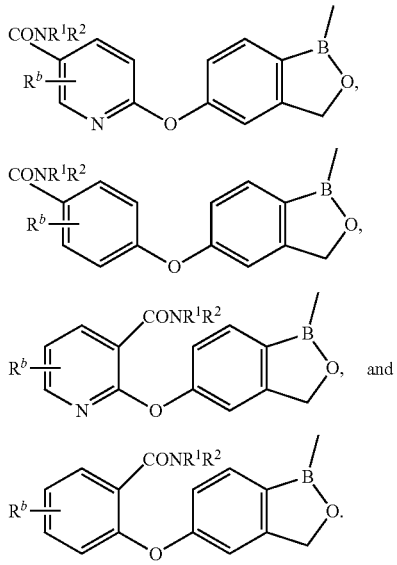

In another embodiment, the volatile compound of the invention is selected from:

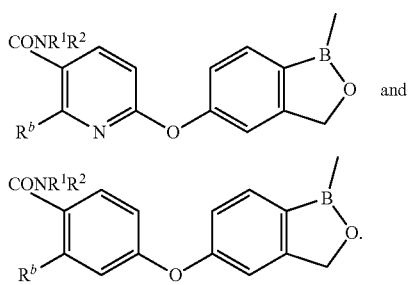

In another embodiment, the volatile compound of the invention is selected from:

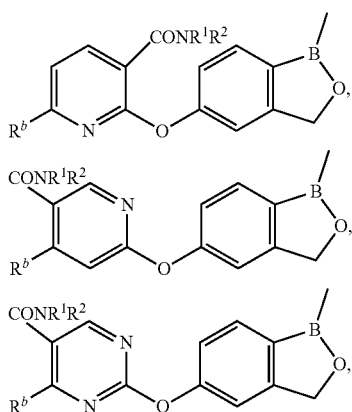

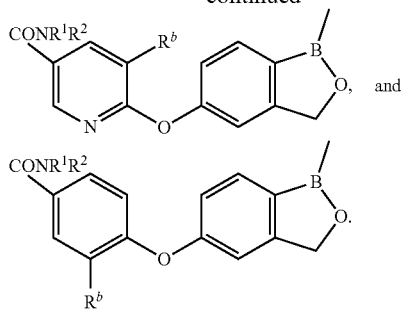

In one embodiment, $R^b$ is selected from fluorine and chlorine. In another embodiment, $R^b$ is selected from $OR^{20}$ and $NR^{21}R^{22}$. In another embodiment when $R^b$ is $OR^{20}$, $R^{20}$ is selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In another embodiment when $R^b$ is $OR^{20}$, $R^{20}$ is selected from H, substituted or unsubstituted alkyl, substituted or unsubstituted heteroalkyl and substituted or unsubstituted cycloalkyl. In another embodiment when $R^b$ is $OR^{20}$, $R^{20}$ is unsubstituted $C_{1-6}$ alkyl. In another embodiment when $R^b$ is $OR^{20}$, $R^{20}$ is unsubstituted cycloalkyl. In another embodiment when $R^b$ is $OR^{20}$, $R^{20}$ is alkyl, substituted with a member selected from substituted or unsubstituted $C_{1-6}$ alkoxy. In another embodiment when $R^b$ is $OR^{20}$, $R^{20}$ is alkyl, substituted with at least one halogen. In another embodiment when $R^b$ $OR^{20}$, $R^{20}$ is alkyl, substituted with at least one oxo moiety.

In another embodiment when $R^b$ is $OR^{20}$, $R^{20}$ is a member selected from —$CH_3$, —$CH_2CH_3$, —$(CH_2)_2CH_3$, —$CH(CH_3)_2$, —$CH_2CF_3$, —$CH_2CHF_2$, —$CH_2CH_2(OH)$, —$CH_2CH_2(OCH_3)$, —$CH_2CH_2(OC(CH_3)_2)$, —$C(O)CH_3$, —$CH_2CH_2OC(O)CH_3$, —$CH_2C(O)OCH_2CH_3$, —$CH_2C(O)OC(CH_3)_3$, —$(CH_2)_3C(O)CH_3$, —$CH_2C(O)OC(CH_3)_3$, cyclopentyl, cyclohexyl,

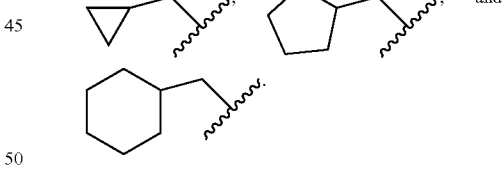

In another embodiment when $R^b$ is $NR^{21}R^{22}$, $R^{21}$ and $R^{22}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In another embodiment when $R^b$ is $NR^{21}R^{22}$, $R^{21}$ is H or unsubstituted alkyl; and $R^{22}$ is unsubstituted alkyl or alkyl substituted with a member selected from hydroxyl, phenyl, unsubstituted alkoxy and alkoxy substituted with a phenyl. In a further embodiment when $R^b$ is $NR^{21}R^{22}$, $R^{21}$ is H or $CH_3$.

In another embodiment when $R^b$ is $NR^{21}R^{22}$, $R^{21}$ and $R^{22}$ are independently selected from substituted or unsubstituted alkyl. In another embodiment when $R^b$ is $NR^{21}R^{22}$, $R^{21}$ is unsubstituted alkyl; and $R^{22}$ is substituted or unsubstituted alkyl. In another embodiment when $R^b$ is $NR^{21}R^{22}$, $R^{21}$ is unsubstituted alkyl; and $R^{22}$ is alkyl, substituted with a member selected from substituted or unsubstituted alkoxy and hydroxyl. In another embodiment when $R^b$ is $NR^{21}R^{22}$, $R^{21}$ is unsubstituted alkyl; and $R^{22}$ is alkyl, substituted with unsubstituted alkoxy. In another embodiment when $R^b$ is $NR^{21}R^{22}$, $R^{21}$ is unsubstituted alkyl; and $R^{22}$ is alkyl, substituted with alkoxy, substituted with phenyl. In another embodiment when $R^b$ is $NR^{21}R^{22}$, $R^{21}$ is unsubstituted alkyl; and $R^{22}$ is alkyl, substituted with unsubstituted alkoxy. In another embodiment when $R^b$ is $NR^{21}R^{22}$, $R^{21}$ and $R^{22}$ together with the nitrogen to which they are attached, are combined to form a 4- to 8-membered substituted or unsubstituted heterocycloalkyl ring. In another embodiment when $R^b$ is $NR^{21}R^{22}$, $R^{21}$ and $R^{22}$ together with the nitrogen to which they are attached, are combined to form a 5- or 6-membered substituted or unsubstituted heterocycloalkyl ring.

In another embodiment, $R^b$ is selected from $N(CH_3)_2$, $N(CH_3)(CH_2CH_2(OCH_3))$, $N(CH_3)(CH_2CH_2OH)$, $NH_2$, $NHCH_3$, $NH(CH_2CH_2(OCH_3))$, $NH(CH_2CH_2(OCH_2Ph))$, $NH(CH_2Ph)$, $NH(C(CH_3)_3)$ and $NH(CH_2CH_2OH)$. In another embodiment, $R^b$ is selected from

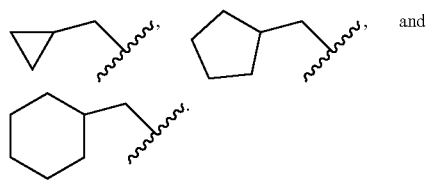

and

Additional oxaborole moieties are also disclosed previously in U.S. Pat. No. 8,039,450, and patent application publication US 2009/0291917, the contents of which are hereby incorporated by reference in their entireties.

In another embodiment, the compound provided has a structure of formula (A1) or (A2):

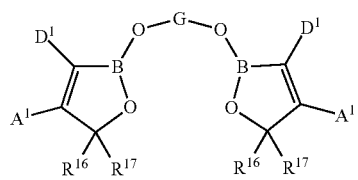

(A1)

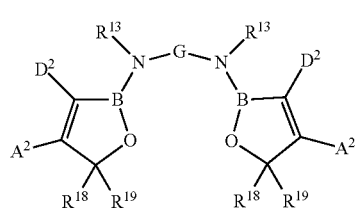

(A2)

wherein each of $A^1$, $A^2$, $D^1$, and $D^2$ is independently hydrogen, substituted or unsubstituted $C_{1-18}$-alkyl, arylalkyl, aryl, or heterocyclic; or $A^1$ and $D^1$, or $A^2$ and $D^2$ together form a 5, 6, or 7-membered fused ring which is substituted or unsubstituted;

each of $R^{13}$, $R^{16}$, $R^{17}$, $R^{18}$, and $R^{19}$ is independently hydrogen, substituted or unsubstituted $C_{1-6}$-alkyl, nitrile, nitro, aryl or aryl alkyl; or $R^{16}$ and $R^{17}$, or $R^{18}$ and $R^{19}$ together form an alicyclic ring which is substituted or unsubstituted;

B is boron; and

G is a substituted or unsubstituted $C_{1-18}$-alkylene, arylalkylene, arylene, or heterocyclic moiety.

In another embodiment, each of $R^A$ and $R^B$ is independently

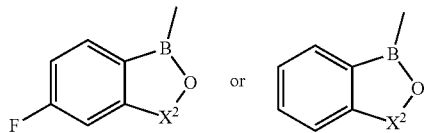

wherein $X^2=(CR^{62})_m$ and m=1, 2, 3, or 4.

In another embodiment, each of $R^A$ and $R^B$ is independently

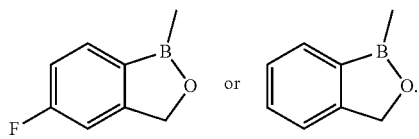

In another embodiment, the compound provided has the structure of

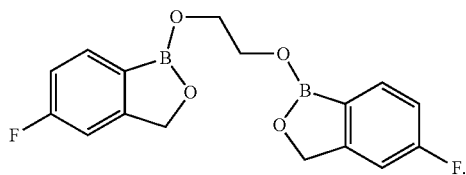 [SMILES: Fc1ccc2c(c1)COB2OCCOB1OCc2cc(F)ccc21]

Additional oxaborole moieties are also disclosed previously in U.S. Pat. No. 5,880,188, the content of which is hereby incorporated by reference in its entirety.

In another aspect, the antimicrobial compound, sometimes called a benzoxaborole, is a compound having a structure of formula (AX):

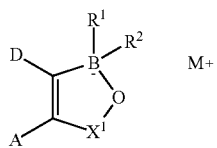

(AX)

wherein A and D together with the carbon atoms to which they are attached form a 5-, 6-, or 7-membered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings; B is boron; $R^1$ and $R^2$ are each independently halogen or nitrile; $X^1$ is a group $—(CR^3R^4)_p$ wherein $R^3$ and $R^4$ are each independently hydrogen, $C_1$-$C_6$-alkyl, nitrile, nitro, aryl, arylalkyl or $R^3$ and $R^4$ together with the carbon atom to which they are attached form an alicyclic ring; p is 1, 2, 3, or 4;

M+ is a counterion;
and agriculturally acceptable salts thereof.

Additional disclosure and methods for making a compound of formula AX can be found in U.S. Pat. No. 9,730,454, issued Aug. 15, 2017, the disclosure of which is incorporated by reference in its entirety.

In one embodiment, the compound is volatile. In another embodiment, the compound has antimicrobial activity.

In one embodiment, the compound of formula (AX) is prepared from a (precursor) compound selected from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof. In another embodiment, the compound of formula (A) is prepared from a (precursor) compound selected from the group consisting of 5-fluorobenzo[c][1,2]oxaborol-1(3H)-ol; 5-chlorobenzo[c][1,2]oxaborol-1(3H)-ol; benzo[c][1,2]oxaborol-1(3H)-ol; and combinations thereof.

In another embodiment, the compound of formula (AX) is

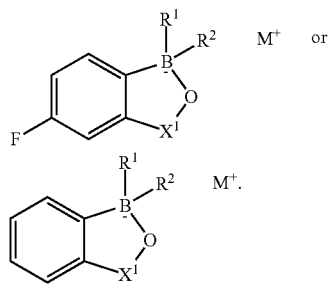

In a further embodiment, the compound of formula (AX) is selected from the group consisting of

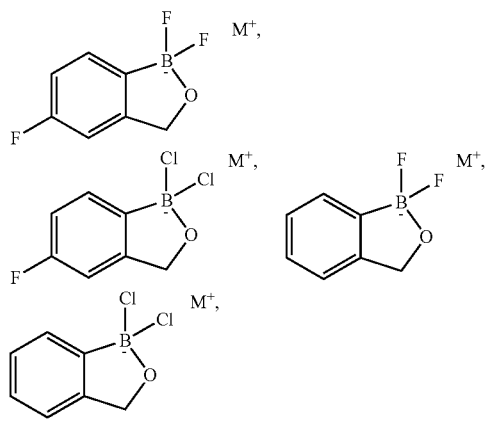

and combinations thereof. In another embodiment, the compound of formula (A) is selected from the group consisting of

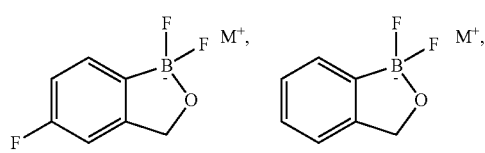

and combinations thereof. In another embodiment, the compound of formula (AX) is

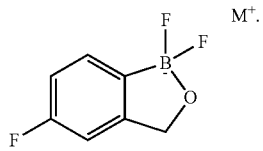

Additional oxaborole compounds useful for preparing compounds of formula (AX) are also disclosed in U.S. Pat. No. 5,880,188, the content of which is hereby incorporated by reference in its entirety. In another aspect, provided is a mixture or composition comprising the compound of formula (AX).

In another aspect, provided is a method of using a compound against pathogens affecting meats, plants, or plant parts, comprising contacting the meats, plants, or plant parts with an effective amount of the compound having a structure of formula (A):

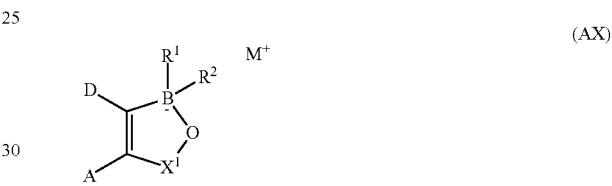

(AX)

wherein A and D together with the carbon atoms to which they are attached form a 5-, 6-, or 7-membered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings; B is boron;

$R^1$ and $R^2$ are each independently halogen or nitrile;

$X^1$ is a group —$(CR^3R^4)_p$ wherein $R^3$ and $R^4$ are each independently hydrogen, $C_1$-$C_6$-alkyl, nitrile, nitro, aryl, arylalkyl or $R^3$ and $R^4$ together with the carbon atom to which they are attached form an alicyclic ring;

p is 1, 2, 3, or 4;

and agriculturally acceptable salts thereof.

In one embodiment, the compound is volatile. In another embodiment, the compound is a fungicide. In another embodiment, the contacting comprises direct contact or contact as a volatile compound, i.e., via direct contact or via volatile activity. In a further embodiment, the contacting comprises application of a liquid formulation.

In one embodiment, the method of using a volatile compound against pathogens affecting meats, plants, or plant parts, comprises providing a compound of formula (AX) in gaseous form; and contacting a meat, plant, or plant part with an effective amount of the compound of formula (AX) in gaseous form.

In another embodiment, the method of using a volatile compound against pathogens affecting meats, plants, or plant parts, comprises placing a meat, plant, or plant part in a container; and introducing into the container and in contact with the meat, plant, or plant part an effective amount of the compound of formula (A) in gaseous form.

In another embodiment, the method of using a volatile compound against pathogens affecting meats, plants, or plant parts, comprises contacting the meats, plants, or plant parts with an atmosphere comprising an effective amount of the compound of formula (A) in gaseous form.

In one embodiment, the compound of formula (A) is prepared from a (precursor) compound selected from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof. In another embodiment, the compound of formula (A) is prepared from a (precursor) compound selected from the group consisting of 5-fluorobenzo[c][1,2]oxaborol-1(3H)-ol; 5-chlorobenzo[c][1,2]oxaborol-1(3H)-ol; benzo[c][1,2]oxaborol-1(3H)-ol; and combinations thereof.

In another embodiment, the compound of formula (AX) is

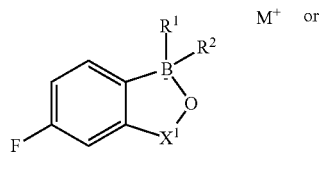

In a further embodiment, the compound of formula (AX) is selected from the group consisting of

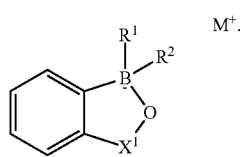

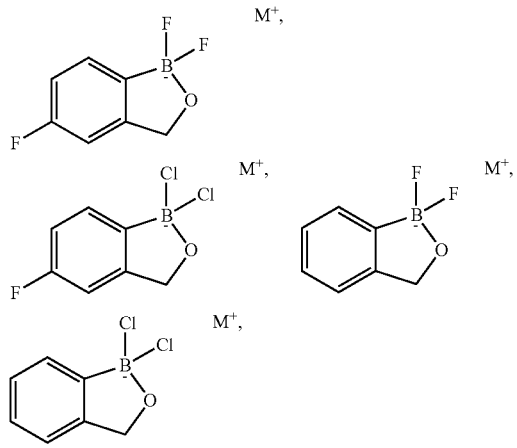

and combinations thereof. In another embodiment, the compound of formula (A) is selected from the group consisting of

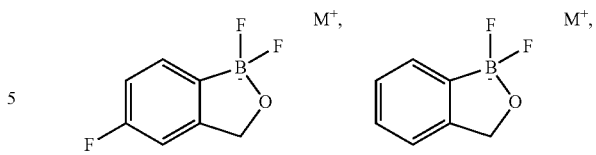

and combinations thereof. In another embodiment, the compound of formula (AX) is

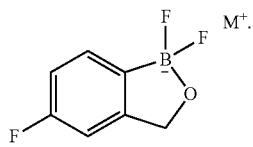

In some aspects, $M^+$ is an alkali metal ion.

Compounds A, B, and/or C may be used individually or as a mixture or combination. The benzoxaborole compounds may also be used in combination with a carrier to form a benzoxaborole treatment. The benzoxaborole treatment provides antimicrobial protection to food, such as plants, crops, or meats, when administered, applied, or exposed to the plants, crops, or meats. While the mechanism of action of the benzoxaborole compound is not fully understood, it is thought to proceed via blocking or inhibition of protein synthesis in microorganisms and/or blocking cytoplasmic leucyl-tRNA synthetase (LeuRS) activity, thereby preventing growth of microorganisms on food.

Benzoxaboroles, including Compounds A, B, and/or C, may be used in any form, including, but not limited to, a liquid, a solid, or a gaseous composition. In particular, the present method provides application of a benzoxaborole compound to food product packaging materials as a spray, a mist, a gel, a thermal and non-thermal fog, a dip, a drench, a vapor, a gas, or via sublimation.

Carriers of the present disclosure may be combined with one or more active benzoxaborole compounds to form a benzoxaborole treatment. Treatment carriers of the present disclosure may comprise gases, solutions, solvents, or chemicals. For example, a liquid carrier of the present disclosure may comprise water, buffer, saline solution, a solvent, or solvent-based solution, etc. Illustrative liquid solvent carriers of the present disclosure include, but are not limited to, liquid carbon dioxide ($CO_2$), such as supercritical $CO_2$. Gaseous carriers of the benzoxaborole compounds may comprise nitrogen ($N_2$), carbon dioxide ($CO_2$), or sulfur dioxide ($SO_2$).

Benzoxaborole compound treatments, such as those comprising Compounds A, B, and/or C, with or without a carrier, may be applied to packaging materials. More specifically, the benzoxaborole treatments of the present disclosure may be applied, imbedded, impregnated, or coated onto or into one or more surfaces of a packaging material (e.g., PET clamshells or liner materials) or a device (e.g., a container or a chamber), collectively and interchangeably called a "chamber." When coated onto or imbedded into surfaces of packaging materials, the benzoxaborole compound treatment volatilizes to treat food products, which ultimately preserves freshness of the food. Thus, the compound treatments of the present disclosure allow for the uniform treatment of food packaging materials to protect food products comprised therein.

A chamber of the present disclosure may be any container in which a food product may be comprised therein for harvest, storage, and/or retail usage. For example, a chamber may be made of any material sufficient to hold food including, but not limited to, cardboard, paper, paperboard, corrugated paper, plastic (e.g., thermosets and thermoplastics), glass, polystyrene, cellulosic material, metals (e.g., aluminum, foils, laminates, tinplate, and/or steel, such as tin-free steel), or any other semipermeable or impermeable material. Exemplary chambers of the present disclosure may be made of polyester, such as polycarbonate, polyethylene naphthalate, and polyethylene terephthalate (i.e., PET or PETE). Thus, an illustrative embodiment of a chamber of the present disclosure is a PET clamshell.

The chamber of the present disclosure may be of any size to hold food products within the packaging materials, such as an individual or singulated chamber embodiment. For example, illustrative individual chambers may have a volume ranging from about 0.1 liters (L) to about 50 L, from about 0.1 L to about 40 L, from about 0.1 L to about 30 L, from about 0.1 L to about 20 L, from about 0.1 L to about 10 L, from about 0.1 L to about 5 L, from about 0.1 L to about 4 L, from about 0.1 L to about 3 L, from about 0.1 L to about 2 L, from about 1 L to about 50 L, from about 5 L to about 40 L, from about 20 L to about 40 L, from about 25 L to about 50 L, from about 30 L to about 40 L, from about 35 L to about 40 L, and at about 0.1 L, about 0.2 L, about 0.3 L, about 0.4 L, about 0.5 L, about 1 L, about 2 L, about 10 L, about 20 L, about 30 L, about 35 L, about 40 L, and about 50 L.

An additional chamber embodiment may be capable of holding a plurality of individual chambers. A plurality of individual chambers, such a PET clamshells, may include two or more to thousands, to many thousands to tens or hundreds of thousands or millions of PET clamshells. For example, one box may comprise about 384 clamshells, and a chamber embodiment may comprise thousands of boxes of clamshells (e.g., from about 384,000 to about 3,840,000 to about 384,000,000 of clamshells). Thus, a plurality of PET clamshells is also an illustrative embodiment of the chamber of the present disclosure, which is particularly utilized for large-scale and/or commercial treatment methods of chambers.

A further embodiment of the chamber of the present disclosure may comprise a liquid-absorbing material. The liquid-absorbing material may be comprised within the chamber, such as on the internal top, bottom or side panels of the chamber. The liquid-absorbing material may be comprised on the exterior of the chamber, such as on the external top, bottom or side panels of the chamber. The liquid-absorbing material may also be comprised on or in one or more liners, wrapping, labels, tags, stickers, pads, or other packing components located, attached, and/or affixed to the inside or the outside of the chamber.

The liquid-absorbing material may comprise any material that is able to absorb and retain a liquid composition of the active compound. For example, illustrative embodiments of the liquid-absorbing material include, but are not limited to, cotton, paper, foam, etc.

Absorption of an active ingredient (i.e., benzoxaborole) into the liquid-absorbing material enables the liquid-absorbing material to serve as a reservoir capable of releasing the benzoxaborole treatment to the food product comprised in the chamber over a time period. The liquid-absorbing material may provide for slow-release or quick-release of the benzoxaborole treatment to the food product. Thus, the liquid-absorbing material enables differential treatment of the food product based on the time period required for protection of food products comprised therein. For example, food products that need limited antimicrobial protection may be packaged in a chamber comprising a quick-release liquid-absorbing material, while food products requiring an extended term of antimicrobial protection may be packaged in a chamber comprising a slow-release liquid-absorbing material.

Slow-release liquid-absorbing materials include, but are not limited to, materials that enable the release of the active ingredient to the food product for a time period of over 12 hours, such as from over 12 hours to about 31 days, including from over 12 hours to about 25 days, from over 12 hours to about 20 days, from over 12 hours to about 15 days, from over 12 hours to about 10 days, from over 12 hours to about 5 days, from over 12 hours to about 30 days, from over 12 hours to about 24 days, from about 24 hours to about 30 days, from about 2 days to about 28 days, from about 3 days to about 25 days, from about 4 days to about 20 days, and about 5 days, about 10 days, about 15 days, about 20 days, about 25 days, about 30 days, and any number of days between 1 day to 30 days.

Quick-release liquid-absorbing materials include, but are not limited to, materials that enable the release of the active ingredient to the food product for a time period ranging from about 12 hours or less, such as from about 5 seconds to about 12 hours, from about 5 seconds to about 10 hours, from about 10 seconds to about 8 hours, from about 15 seconds to about 6 hours, from about 20 seconds to about 4 hours, from about 25 seconds to about 2 hours, from about 5 seconds to about 1 hour, from about 10 seconds to about 45 minutes, from about 15 seconds to about 30 minutes, from about 20 seconds to about 15 minutes, from about 25 seconds to about 5 minutes, from about 5 seconds to about 1 minute, from about 5 seconds to about 30 seconds, from about 5 seconds to about 15 seconds, and from about 5 seconds to about 10 seconds.

The chamber may also comprise one or more holes or apertures. The apertures may have any shape, and may have a size ranging from about 2 mm to about 2 cm, and from about 2.5 mm to about 1.5 cm, from about 5 mm to about 1.5 cm, from about 7.5 mm to about 1.25 cm, from about 10 mm to about 1 cm, from about 15 mm to about 0.75 cm, from about 20 mm to about 0.5 cm, and from about 25 mm to about 0.25 cm. In addition, the apertures may be in any location on the chamber material, but typically, the apertures are located at the base, the lid, the sides, or a combination thereof on the chamber. The apertures allow for introduction of treatment to the chamber and/or release of treatment from the chamber.

Upon introduction of compound treatment into or onto the chamber, the apertures permit uniform distribution of treatment vapor, gas, or fog particles throughout the chamber. The apertures also allow for full drainage, venting, and/or release of the unused portion of the treatment or treatment carrier from the chamber. Unused treatment and/or treatment carrier may be recycled to treat subsequent and/or additional containers, materials, or chambers.

An illustrative example of a product of the method described herein is one or more benzoxaborole-treated PET clamshell, such as a plurality of PET clamshells. PET clamshells are commonly used to transport strawberries and other soft fruits. Therefore, a benzoxaborole-treated PET clamshell would provide the greatest protection to the fruit contained therein since the active ingredient is coated on the surfaces of the primary packaging of the fruit. Primary protection of the fruit could also occur via treatment of a material contained within the PET clamshell, such as a liquid-absorbing material in the form of a tag, a pad, or other embodiments described herein. Secondary protection of the fruit would occur by applying the active ingredient to a liner, a box, a bag, a wrap or other packaging material in which the primary chambers are placed for storage or transport.

Methods of Administering Benzoxaborole Compounds

The present disclosure is directed to methods of uniformly treating food products by providing antimicrobial protection to food, such as plants, crops, and meats. The present methods are directed to large-scale treatment of food packaging materials to uniformly protect plants from plant pathogens and microorganisms that cause food decay. More specifically, plant pathogens that inhibit, reduce, or compromise food freshness may be treated, prevented, or eradicated by the methods described herein.

Exemplary, microorganisms encompassed by the present disclosure include, but are not limited to, *Botrytis cinerea, Mucor piriformis, Fusarium sambucinum, Aspergillus brasiliensis*, and *Peniciliium expansum*. Additional pathogens encompassed by the present invention include, but are not limited to *Acremonium* spp., *Albugo* spp., *Alternaria* spp., *Ascochyta* spp., *Aspergillus* spp., *Botryodiplodia* spp., *Botryospheria* spp., *Botrytis* spp., *Byssochlamys* spp., *Candida* spp., *Cephalosporium* spp., *Ceratocystis* spp., *Cercospora* spp., *Chalara* spp., *Cladosporium* spp., *Colletotrichum* spp., *Cryptosporiopsis* spp., *Cylindrocarpon* spp., *Debaryomyces* spp., *Diaporthe* spp., *Didymella* spp., *Diplodia* spp., *Dothiorella* spp., *Elsinoe* spp., *Fusarium* spp., *Geotrichum* spp., *Gloeosporium* spp., *Glomerella* spp., *Helminthosporium* spp., *Khuskia* spp., *Lasiodiplodia* spp., *Macrophoma* spp., *Macrophomina* spp., *Microdochium* spp., *Monilinia* spp., *Monilochaethes* spp., *Mucor* spp., *Mycocentrospora* spp., *Mycosphaerella* spp., *Nectria* spp., *Neofabraea* spp., *Nigrospora* spp., *Penicillium* spp., *Peronophythora* spp., *Peronospora* spp., *Pestalotiopsis* spp., *Pezicula* spp., *Phacidiopycnis* spp., *Phoma* spp., *Phomopsis* spp., *Phyllosticta* spp., *Phytophthora* spp., *Polyscytalum* spp., *Pseudocercospora* spp., *Pyricularia* spp., *Pythium* spp., *Rhizoctonia* spp., *Rhizopus* spp., *Sclerotium* spp., *Sclerotinia* spp., *Septoria* spp., *Sphaceloma* spp., *Sphaeropsis* spp., *Stemphyllium* spp., *Stilbella* spp., *Thielaviopsis* spp., *Thyronectria* spp., *Trachysphaera* spp., *Uromyces* spp., *Ustilago* spp., *Venturia* spp., and *Verticillium* spp., and bacterial pathogens, such as *Bacillus* spp., *Campylobacter* spp., *Clavibacter* spp., *Clostridium* spp., *Erwinia* spp., *Escherichia* spp., *Lactobacillus* spp., *Leuconostoc* spp., *Listeria* spp., *Pantoea* spp., *Pectobacterium* spp., *Pseudomonas* spp., *Ralstonia* spp., *Salmonella* spp., *Shigella* spp., *Staphylococcus* spp., *Vibrio* spp., *Xanthomonas* spp., and *Yersinia* spp.

Benzoxaborole treatments may be applied, administered, or coated on the inside or the outside of a chamber or packaging material. When the benzoxaborole treatment is in any form, but particularly in liquid, spray, vapor, or gas form, a drying step may be provided in the present method that allows excess treatment carrier to dry.

This step may also produce a residue of the active benzoxaborole ingredient at the proper levels of efficacy on the surface of the food packaging material in order to provide extended antimicrobial control and inhibition for plants, crops, and meats contained therein.

Any food product, including plants, crops, or meats, may be treated using the present method. Minimally-processed packaged products (e.g., packaged vegetables, fruits, or meats) may also be treated with the method described herein. Horticultural crops of the present method include, but are not limited to, vegetable crops, fruit crops, edible nuts, flowers and ornamental crops, nursery crops, aromatic crops, and medicinal crops.

Plants and agricultural crops in any production cycle may be used in the method of the present application. For example, post-harvest plants and crops may be treated during field packing, palletization, in-box, storage, and throughout the distribution network. Further, plants being transported by any mode, including, but not limited to local vehicles, transport trailers, marine containers, aircraft containers, etc. may be treated using the method described herein.

Ideally, the chamber or plurality of chambers of the present disclosure are treated prior to use during food field-packaging of plants, meats, or crops, such as soft fruits. For example, treated chambers may be located, stored, and/or kept at the site of clamshell manufacturers, at the central facility of farmers or ranchers, or in a portable unit for immediate in-field treatments. Additionally, treated chambers or materials may be provided to a food producer directly from the manufacturer, wherein the manufacturer has previously applied benzoxaborole to the surface of the packaging. Alternatively, a food producer may independently use a method, machine, or instrument to treat containers or packaging materials with the benzoxaborole compositions as described herein.

Large-scale treatment of food product packaging materials and chambers are comprised in the methods of the present disclosure. Large-scale treatment comprises treatment of chambers or a plurality of chambers in mass, and typically for commercial and/or industrial use. For example, the methods of the present disclosure may comprise treating a plurality of chambers with the benzoxaborole active ingredient described herein. Large-scale treatment methods of the present disclosure may occur before the chamber has been formed (i.e., preformation), during formation of the chamber (i.e., formation), and after the chamber has been formed (i.e., postformation). Formation is the process of forming or producing one or more chambers of the present disclosure, which may include thermoforming.

Preformation treatment of the chamber comprises contacting a packaging material, such as plastic, that will be formed into the chamber with an active ingredient of the present disclosure (e.g., benzoxaborole) prior to the beginning of the formation process. Formation comprises treatment of the packaging material of the chamber with the active ingredient after the formation process has started. Postformation treatment of the chamber occurs when the packaging material has been formed into a chamber and the chamber is then treated with the active ingredient. For example, the chambers may be treated with the active ingredient prior to, during, or after formation of the chamber using methods including, but not limited to, dipping, drenching, spraying, painting, vaporizing, and/or sublimation.

One embodiment of the large-scale method described herein comprises use of a printer to print the active compound treatment on the lining or material of a plurality of chambers. Another embodiment of the large-scale treatment method comprises spraying the plurality of chambers with the active compound treatment. A further embodiment of the large-scale treatment method comprises dipping a plurality of chambers into a vat of active compound treatment and removing the treated chambers to dry onto the chamber material. Additionally, fogging or spraying a plurality of chambers with the active compound during manufacturing in an industrial-sized device is also an embodiment of the large-scale method of the present disclosure.

Food products may or may not be inside of the chamber during application of the benzoxaborole treatment. If the food product is already inside the chamber, treatment of the chamber with the active ingredient may be applied while the chamber is open, closed, or sealed. Typically, however, after the treated chambers are produced, food products, such as plants, crops, or meats, may be manually or robotically (e.g., by a machine) placed in the treated chamber in preparation for antimicrobial treatment of the food.

The proximity and/or distance between the emitting source of active ingredient and the food product is critical. Notably, the distance from the benzoxaborole coated surfaces of the packaging material or chamber and the food product is inversely related to the efficacy of antimicrobial protection of the food. In other words, the greater the distance between the coated/treated surfaces of the material or chamber and the food product, the lesser is the level of antimicrobial protection conveyed to the treated food product, including plants, crops, or meat.

Related to this property, treated surfaces of a chamber or packaging material, such as a bag, a box, a wrap, a liner, or other packaging material that is placed over an entire pallet of clamshells of food products may be less effective in delivering the active ingredient to the food than a treated surface that is immediately adjacent to or in contact with the plant, crop, or meat food products, such as the clamshell surfaces themselves. Therefore, having the treatment coated directly on a surface or imbedded into the individual product chamber that is the primary packaging material, meaning the first layer of packaging of the food product, provides the greatest antimicrobial protection to the food product. Similarly, treating the internal surface of the primary packaging material, such as a chamber, provides even greater antimicrobial effect than treating an external surface of the chamber. Therefore, the distance between the emitting source of the active ingredient and the food product should be minimized for best results.

More specifically, the distance between the emitting source and the food product should remain less than about 6 feet. In an illustrative embodiment, the distance between the emitting source and the food product ranges from about 0.1 inches to about 6 feet, from about 0.5 inches to about 5 feet, from about 1 inch to about 4 feet, from about 1.5 inches to about 3 feet, from about 2 inches to about 2 feet, from about 0.5 inches to about 12 inches, from about 1 inch to about 24 inches, from about 0.5 inches to about 6 inches, from about 0.5 inches to about 5 inches, from about 0.5 inches to about 4 inches, from about 0.5 inches to about 3 inches, from about 0.5 inches to about 2 inches, and from about 0.5 inches to about 1 inch. Close proximity of the emitting source of the benzoxaborole active ingredient applied to the primary PET clamshell ensures that the food product is exposed to the active ingredient which inhibits microorganisms that may infect the food.

An exemplary embodiment of the method described herein comprises vaporizing or subliming the benzoxaborole compound or molecule into a gaseous form. The benzoxaborole compound gas or vapor may be at any concentration that allows the compound or molecule to adhere to the chamber (e.g., a clamshell) or packaging surfaces prior to taking the chamber or material into a field for the harvest operation.

For example, the benzoxaborole compound vapor or gas may be effectively administered to a chamber at a concentration ranging from about 0.1 mg/chamber to about 10 mg/chamber, from about 0.1 mg/chamber to about 8 mg/chamber, from about 0.1 mg/chamber to about 7 mg/chamber, from about 0.1 mg/chamber to about 6 mg/chamber, from about 0.1 mg/chamber to about 5.5 mg/chamber, from about 0.1 mg/chamber to about 5 mg/chamber, from about 0.1 mg/chamber to about 4 mg/chamber, from about 0.1 mg/chamber to about 3.5 mg/chamber, from about 0.1 mg/chamber to about 3.2 mg/chamber, from about 0.1 mg/chamber to about 2 mg/chamber, from about 0.1 mg/chamber to about 1.5 mg/chamber, from about 0.1 mg/chamber to about 1 mg/chamber, from about 0.1 mg/chamber to about 0.35 mg/chamber, from about 0.1 mg/chamber to about 0.32 mg/chamber, from about 0.1 mg/chamber to about 0.25 mg/chamber, from about 0.1 mg/chamber to about 0.22 mg/chamber, 0.2 mg/chamber to about 8 mg/chamber, from about 0.2 mg/chamber to about 7 mg/chamber, from about 0.2 mg/chamber to about 6 mg/chamber, from about 0.2 mg/chamber to about 5.5 mg/chamber, from about 0.2 mg/chamber to about 5 mg/chamber, from about 0.2 mg/chamber to about 4 mg/chamber, from about 0.2 mg/chamber to about 3.5 mg/chamber, from about 0.2 mg/chamber to about 3.2 mg/chamber, from about 0.2 mg/chamber to about 2 mg/chamber, from about 0.2 mg/chamber to about 1.5 mg/chamber, from about 0.2 mg/chamber to about 1 mg/chamber, from about 0.2 mg/chamber to about 0.35 mg/chamber, from about 0.2 mg/chamber to about 0.32 mg/chamber, from about 0.2 mg/chamber to about 0.25 mg/chamber, from about 0.2 mg/chamber to about 0.22 mg/chamber, 0.2 mg/chamber to about 8 mg/chamber, from about 0.3 mg/chamber to about 7 mg/chamber, from about 0.3 mg/chamber to about 6 mg/chamber, from about 0.3 mg/chamber to about 5.5 mg/chamber, from about 0.3 mg/chamber to about 5 mg/chamber, from about 0.3 mg/chamber to about 4 mg/chamber, from about 0.3 mg/chamber to about 3.5 mg/chamber, from about 0.3 mg/chamber to about 3.2 mg/chamber, from about 0.3 mg/chamber to about 2 mg/chamber, from about 0.3 mg/chamber to about 1.5 mg/chamber, from about 0.3 mg/chamber to about 1 mg/chamber, from about 0.3 mg/chamber to about 0.35 mg/chamber, from about 0.3 mg/chamber to about 0.32 mg/chamber, and at about 0.2 mg/chamber, 0.316 mg/chamber, 1 mg/chamber, 3.16 mg/chamber, and 5 mg/chamber.

Alternatively, the benzoxaborole compound may be prepared as a liquid formulation. Preparing a liquid composition of the benzoxaborole treatment requires mixing the benzoxaborole compound with a liquid carrier, such as a solvent or water or combination thereof. Once the liquid treatment is prepared, the chamber or material is drenched or flooded with the liquid treatment, such that the liquid treatment touches all internal surfaces. Most of the liquid treatment carrier may then be drained from an aperture or hole in the chamber or material. After the carrier is substantially removed from the chamber, residue of the active ingredient (i.e., benzoxaborole) in the remaining liquid is allowed to dry, such as at room temperature (e.g., about 21° C. to about 23° C.).

Drying of the treatment composition, including the liquid carrier, may occur instantaneously or within seconds (secs). In particular, the higher the concentration of active ingredient (i.e., benzoxaborole) and the lower the volume of compound treatment, the less time is required for drying the treatment composition onto the chamber. For example, drying time of the treatment composition onto the chamber material may range from about 0.1 secs to about 60 secs, from about 0.2 secs to about 45 secs, from about 0.3 secs to about 30 secs, from about 0.4 secs to about 20 sec, from about 0.5 secs to about 15 secs, from about 1 sec to about 10 secs, from about 5 secs to about 60 secs, and at about 5 secs. Once dried, the active benzoxaborole ingredient is coated onto the surface of the chamber to provide immediate antimicrobial protection to food, such as plants, crops, or meats placed therein.

As previously mentioned, a liquid benzoxaborole treatment may be administered to a fruit or a vegetable clamshell, such that all internal surfaces of the chamber come into contact with the active ingredient. After draining the treatment carrier (e.g., water or solvent) from the clamshell, warm air (i.e., room temperature) is applied to dry the remaining liquid on the clamshells. The treated clamshells comprising the coated surfaces and active ingredient may then go immediately to the field for picking operations. Food, such as fresh fruits and berries placed within the treated clamshells, is protected from disease microorganisms by the volatile active ingredient (i.e., benzoxaborole) emitted from the surface of the clamshells from the time the fruit is placed inside of the chamber.

In yet another embodiment of the present method, the benzoxaborole active ingredient may be administered by fogging as a fine mist into a suitable chamber. The compound may be fogged using any cold, thermal, ultrasonic, or similar fogging-based technologies. The micron particles of water, solvent, or other carriers in the formulations may assist distribution and deposition of the benzoxaborole particles on the chamber surfaces. Upon drying, the method will result in a thin coating of active ingredient on the chamber surfaces. This thin coating of benzoxaborole will volatilize over time, and uniformly protect the food contents of the chamber from pathogenic infection and decay.

Accordingly, the method described herein provides a large-scale administration of an antimicrobial agent, such as benzoxaborole, to the packaging surfaces of food product chambers. Importantly, the presently described method enables greater uniformity and consistency of application of the active benzoxaborole treatment composition to the food packaging materials. Ultimately, the present large-scale method of uniformly treating food chambers results in a significantly extended time period (i.e., up to about 31 days or a full month) of antimicrobial protection of the food product comprised within the treated chambers.

EXAMPLES

Illustrative embodiments of the methods of the present disclosure are provided herein by way of examples. While the concepts and technology of the present disclosure are susceptible to broad application, various modifications, and alternative forms, specific embodiments will be described here in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

The following experiments were used to determine the effect of different concentrations of benzoxaborole compounds when administered onto the surfaces of packaging materials or chambers by various application techniques. In the following experiments, benzoxaborole treatment compositions are applied to chambers such that food products may be exposed to the antimicrobial treatment for an initial time period.

For example, food products may be exposed to the benzoxaborole treatment on the surfaces of the treated chamber for the initial time period ranging from less than 1 day to about 8 days, and at about 5 days. Treatment temperatures of the chamber during the initial time period ranged from about 0.5° C. to about 5° C., and at about 1° C.

After the initial time period in which the food is exposed to the active ingredient of the treated chamber, the chamber may be unsealed (if previously sealed), and allowed to vent for a secondary time period. The food may remain in the chamber for the secondary time period ranging from about 1 day to about 8 days, and at about 6 days. The temperature of the chamber during the second time period remains at room temperature, which ranges from about 20° C. to about 23° C., and at about 21° C.

After expiration of the secondary time period, inhibition of plant pathogens and infection may be assessed. For example, in vitro samples may have the growth of the microorganism or pathogen on agar or in media assessed, evaluated, and compared to a control sample where no benzoxaborole treatment was administered. Similarly, in vivo samples may have the severity and incidence of pathogenic disease assessed, evaluated, and compared to a control sample where no benzoxaborole treatment was administered or different treatment conditions were applied.

Example 1: Benzoxaborole Compound Treatment of Fruit Clamshells by Spraying, Painting, and Sublimation (In Vivo)

An in vivo assay was used to evaluate the ability of Compound A to volatilize from a clamshell chamber and control pathogenic infection when applied by various techniques. Multiple empty 1-lb PET clamshells (ProducePackaging.com, #036QT) were placed inside triplicate air-tight 36 L chamber (Fisher Scientific, Catalogue #08-642-23C) fitted with a bulkhead septum port (Swagelok, SS-401-61, Solon, OH).

An appropriate amount of Compound A, to achieve a final treatment rate of 5 mg per clamshell (i.e., 5 mg/clamshell), was dissolved in acetone and 100 μL of the solution was pipetted into a small glass tube. The tube was then placed inside a pre-heated sublimation device (0.5" OD by 6" long thermostatically healed copper tube mounted to a 2 L/min aquarium pump) set at 60° C. for 1 minute to allow the acetone to evaporate. Compound A was then introduced into the cabinets of the chamber through the bulkhead port containing the clamshells by using the sublimation device set at 180° C. Compound A headspace was permitted to equilibrate overnight at 21° C.

Five milligrams of Compound A was dissolved in 1 ml of ethanol prior to being uniformly administered to the interior of the clamshell by painting or spraying, and then dried for 5 minutes. After coating the clamshells with Compound A using various application techniques (i.e., sublimation, spraying, or painting), eight ethanol-washed strawberries were placed in the clamshell with stem end facing downwards. Each strawberry fruit was wounded using a T15 screwdriver tip to a uniform depth of eight mm (8 mm). Each fruit wound was inoculated with 20 μL of $1 \times 10^5$ spores/ml pathogen spore suspension of *Botrytis cinerea*, which is a fungal pathogen known to cause gray mold infection of fruits, such as grapes and strawberries. Uninoculated strawberries were removed from their commercial package, and directly transferred into treated clamshells without any washing or inoculation steps.

Treated clamshells lids were closed, and then placed at 1° C. for an initial time period of 5 days. Clamshells were then removed from low temperature, and held for a second time period of 6 days at room temperature where the point of inoculation on the strawberry fruits was assessed for indication of disease incidence reported as a percentage (%). Severity of disease incidence was also reported. Disease severity was rated on a scale ranging from 0 to 4, where "0" indicated no disease severity, "1" indicated minimal disease severity, "2" indicated medium disease severity, "3" indicated high disease severity, and "4" indicated exceptionally high disease severity.

The outcome of this in vivo experiment is summarized in Table 1. Results demonstrate good in vivo antimicrobial activity of Compound A against *B. cinerea*, with a reduction in disease incidence and severity with all three application techniques (i.e., painting, spraying, and sublimation). In particular, each method of treating clamshells showed significant inhibition of gray mold incidence and severity in strawberries as compared to control. More specifically, on Days 1-6, the percentage of gray mold incidence increased from 30.5% to 100% and 0% to a maximum of 0.9% in control fruits and treated inoculated fruits, respectively. Even in uninoculated fruit, the percentage of gray mold incidence increased from 1.5% to 100% and 0% to a maximum of 21.7% in control fruits and treated fruits, respectively. In both inoculated and uninoculated fruits, the spraying technique was comparable to or better than painting or sublimation in minimizing the incidence or severity of gray mold. Ultimately, treating the clamshells with benzoxaborole Compound A significantly inhibited the growth of *B. cinerea* in the strawberries and preserved the freshness of the fruit for at least 3 days longer than the untreated strawberries.

Example 2: Benzoxaborole Compound Treatment of Clamshells Containing Agar Plates by Spraying, Painting, and Sublimation (In Vitro)

An in vitro assay was used to evaluate the ability of Compound A to volatilize from a clamshell to control fungal pathogenic infection when applied to the clamshell by various application techniques. Multiple empty 1-lb PET clamshells (ProducePackaging.com, #036QT) were placed inside triplicate air-tight 36 L chamber (Fisher Scientific, Catalogue #08-642-23C) fitted with a bulkhead septum port (Swagelok, SS-401-61, Solon, OH).

An appropriate amount of Compound A to achieve a final treatment rate of 5 mg/clamshell, 1 mg/clamshell, or 0.2 mg/clamshell, was dissolved in acetone and 100 μL of the solution was pipetted into a small glass tube. The tube was then placed inside a pre-heated sublimation device (0.5" OD by 6" long thermostatically healed copper tube mounted to a 2 L/min aquarium pump) set at 60° C. for 1 minute to allow the acetone to evaporate. Compound A was then introduced into the cabinets of the chamber through the bulkhead port containing the clamshells by using the sublimation device set at 180° C. Compound A headspace was permitted to equilibrate overnight at 21° C.

For paint and spray applications, 5 mg of Compound A was dissolved in 1 ml of ethanol prior to uniformly painting or spraying the interior of the clamshell. After spraying or painting, the clamshell was then permitted to dry for 5 minutes. After coating the clamshells with Compound A using various applications (i.e., sublimation, spraying, or painting), 10-cm Petri plates containing half strength Potato Dextrose Agar were inoculated with 1 μL of 1×10$^5$ spores/ml *Botrytis cinerea* spore suspension. The inoculated petri plates were then sealed with a breathable film (AeraSeal; P/N: B-100, Excel Scientific, Victorville, CA), and placed inside the treated clamshell.

To determine the period of time coated packaging could release effective levels of the active ingredient, treated clamshells containing the inoculated plates were then placed inside a 2.55 L SnapWare airtight container (Model #109842) for three (3) days at 21° C. (Series I). After incubation, plates were removed and cultures were evaluated for percent growth relative to a control based on measurement of fungal colony diameter (mm).

TABLE 1

Comparison of in-clamshell Compound A application techniques to control growth of *Botrytis cinerea* inoculated strawberries as compared to uninoculated fruit.

| Inoculated Fruit | Gray Mold Incidence (%) | | | | | | |
|---|---|---|---|---|---|---|---|
| | Day 0 | Day 1 | Day 2 | Day 3 | Day 4 | Day 5 | Day 6 |
| Control | 30.5 | 62.1 | 84.3 | 93.5 | 100.0 | 100.0 | 100.0 |
| Paint | 0.0 | 0.0 | 0.0 | 0.0 | 0.0 | 0.0 | 0.0 |
| Spray | 0.0 | 0.0 | 0.0 | 0.0 | 0.0 | 0.0 | 0.0 |
| Sublimation | 0.0 | 0.0 | 0.0 | 0.0 | 0.0 | 0.9 | 0.9 |

| | Gray Mold Severity (0-4) | | | | | | |
|---|---|---|---|---|---|---|---|
| | Day 0 | Day 1 | Day 2 | Day 3 | Day 4 | Day 5 | Day 6 |
| Control | 0.2 | 0.4 | 1.1 | 2.1 | 2.6 | 4.0 | 4.0 |
| Paint | 0.0 | 0.0 | 0.0 | 0.0 | 0.0 | 0.0 | 0.0 |
| Spray | 0.0 | 0.0 | 0.0 | 0.0 | 0.0 | 0.0 | 0.0 |
| Sublimation | 0.0 | 0.0 | 0.0 | 0.0 | 0.0 | 0.0 | 0.0 |

| Uninoculated Fruit | Gray Mold Incidence (%) | | | | | | |
|---|---|---|---|---|---|---|---|
| | Day 0 | Day 1 | Day 2 | Day 3 | Day 4 | Day 5 | Day 6 |
| Control | 1.5 | 7.1 | 39.9 | 96.7 | 96.7 | 100.0 | 100.0 |
| Paint | 0.0 | 0.3 | 3.9 | 5.1 | 7.4 | 17.0 | 21.7 |
| Spray | 0.0 | 0.6 | 2.1 | 4.8 | 6.0 | 17.9 | 19.9 |
| Sublimation | 0.0 | 0.3 | 1.5 | 3.3 | 5.7 | 16.7 | 20.2 |

TABLE 1-continued

Comparison of in-clamshell Compound A application techniques to control growth of *Botrytis cinerea* inoculated strawberries as compared to uninoculated fruit.

| | Gray Mold Severity (0-4) | | | | | | |
|---|---|---|---|---|---|---|---|
| | Day 0 | Day 1 | Day 2 | Day 3 | Day 4 | Day 5 | Day 6 |
| Control | 0.3 | 0.9 | 1.5 | 2.8 | 3.5 | 4.0 | 4.0 |
| Paint | 0.0 | 0.1 | 0.5 | 0.8 | 0.9 | 1.1 | 1.1 |
| Spray | 0.0 | 0.2 | 0.3 | 0.5 | 0.7 | 1.2 | 1.3 |
| Sublimation | 0.0 | 0.1 | 0.3 | 0.7 | 0.9 | 1.1 | 1.3 |

Meanwhile, freshly prepared inoculated plates were placed inside the clamshell for an additional three (3) days of incubation (Series 2). This process, where freshly prepared inoculated plates were placed inside the clamshell, was repeated twice more, to produce a 12 full day evaluation of 4 series of 3 days each. The outcome of this in vitro experiment is summarized in Table 2. Results demonstrate good volatile in vitro antimicrobial activity of Compound A against *Botrytis cinerea* with all three application techniques (i.e., painting, spraying, and sublimation). In addition, greater inhibition of pathogenic growth was observed at higher treatment rates.

In particular, each technique of treating clamshells showed significant inhibition of mycelial growth. More specifically, administration of 5 mg/clamshell of benzoxaborole treatment by all three techniques were effective to completely inhibit mycelial cell growth the first six days (Table 2). In the remaining six days, sublimation most effectively inhibited mycelial growth (84.4%), followed by spraying (64.9%), and painting (44.7%). At lower treatment concentrations (i.e., 1 mg/clamshell and 0.2 mg/clamshell), all of the treatment techniques failed to inhibit mycelial cell growth by Days 6 to 9. Ultimately, treating the clamshells with benzoxaborole Compound A significantly inhibited the growth of *B. cinerea* inoculated on agar plates placed therein for time periods typical of fruit storage by the supply chain and consumers.

TABLE 2

Comparison of treatment techniques of Compound A to volatilize from clamshells and provide in vitro inhibition of *Botrytis cinerea*

| | | Mycelial Growth Inhibition (%) | | | |
|---|---|---|---|---|---|
| Method | Rate (mg/ clamshell) | Series 1 (0 to 3 days) | Series 2 (3 to 6 days) | Series 3 (6 to 9 days) | Series 4 (9 to 12 days) |
| Sublimation | 5 | 100.0 | 100.0 | 83.1 | 84.4 |
| | 1 | 90.1 | 0.0 | 0.0 | . . . |
| | 0.2 | 90.9 | 0.0 | 0.0 | . . . |
| Paint | 5 | 100.0 | 100.0 | 57.5 | 44.7 |
| | 1 | 100.0 | 18.8 | 0.0 | — |
| | 0.2 | 3.4 | 0.0 | 0.0 | — |
| Spray | 5 | 100.0 | 100.0 | 61.2 | 64.9 |
| | 1 | 100.0 | 18.6 | 0.0 | . . . |
| | 0.2 | 81.2 | 0.0 | 0.0 | |

Example 3: Dose Response of Benzoxaborole Compound Treatment of Fruit Clamshells by Vapor-Coating (In Vivo)

This in vivo assay was used to evaluate the ability of vaporized Compound A to volatilize from a clamshell in order to control or inhibit pathogenic microorganisms. This experiment was conducted exactly as described in Example 1, with a few exceptions. After equilibrating the clamshell overnight at 21° C., Compound A was administered to the clamshell as a vapor only. In addition, Compound A was vapor-coated onto the surface of the clamshell at a final treatment rate of 3.16 mg/clamshell, 1 mg/clamshell, or 0.316 mg/clamshell. After vapor-coating application, Compound A headspace was permitted to equilibrate overnight at 21° C. Strawberries were inoculated with *Botrytis cinerea*, placed within the clamshells for an initial time period, and assessed for disease incidence and severity over a second time period as described in Example 1.

The outcome of this in vivo experiment is summarized in Table 3. Results demonstrate good in vivo antimicrobial activity of Compound A against *B. cinerea*, with a greater reduction in disease incidence and severity observed at higher treatment rates.

In particular, each concentration of active ingredient on treated clamshells showed inhibition of gray mold severity in inoculated strawberries as compared to control (see Table 3). More specifically, on Days 1-6, the percentage of gray mold severity increased from 0.8 to 4.0 in control fruits as compared to 0 to 0.2 and 0 to 0.7 for inoculated fruits treated with 3.16 mg/clamshell or 1 mg/clamshell of Compound A, respectively. At the lower treatment concentration of 0.316 mg/clamshell, the percentage of gray mold severity increased from 0.4 to 3.9. Ultimately, treating the clamshells with different concentrations of benzoxaborole Compound A significantly inhibited the growth of *B. cinerea* in the strawberries in a dose dependent manner.

TABLE 3

Dose response of in-clamshell Compound A applied by sublimation to control growth of *Botrytis cinerea* inoculated on strawberries.

| Inoculated Fruit Rate | Gray Mold Severity (0-4) | | | | | |
|---|---|---|---|---|---|---|
| (mg per clamshell) | Day 1 | Day 2 | Day 3 | Day 4 | Day 5 | Day 6 |
| 3.16 | 0.0 | 0.0 | 0.0 | 0.0 | 0.1 | 0.2 |
| 1.00 | 0.0 | 0.0 | 0.0 | 0.1 | 0.4 | 0.7 |
| 0.316 | 0.4 | 1.3 | 2.2 | 3.4 | 3.8 | 3.9 |
| Control | 0.8 | 1.8 | 2.7 | 3.6 | 4.0 | 4.0 |

Example 4: Dose Response of Benzoxaborole Compound Treatment of Fruit Clamshells by Spraying (In Vivo)

This in vivo assay was used to evaluate the ability of different concentrations of Compound A to volatilize from clamshell in order to control or inhibit fruit infection by pathogenic microorganism, *Botrytis cinerea*. This experiment was conducted exactly as described in Example 1, with a few exceptions. After equilibrating the clamshell overnight at 21° C., Compound A was administered to the clamshells by spraying only. Compound A was sprayed onto the surface of the clamshells at a final treatment rate of 5 mg/clamshell or 1 mg/clamshell. The clamshells were then permitted to dry for 5 minutes. Strawberries were inoculated with *Botrytis cinerea*, placed within the clamshells for the initial time period (i.e., 5 days), and assessed for disease incidence and severity over the second time period (i.e., 6 days) as described in Example 1.

treated inoculated fruits and no growth in 5 mg/clamshell-treated inoculated fruits. For uninoculated fruits, both control and 1 mg/clamshell-treated fruits showed a gray mold severity level of 4.0 by Day 4, while the 5 mg/clamshell-treated uninoculated fruits only showed a gray mold severity level of 3.5 on Day 6. Ultimately, these data demonstrate that treating clamshells with different concentrations of benzoxaborole Compound A significantly inhibited the gray mold infection of *B. cinerea* inoculated in strawberries in a dose dependent manner.

TABLE 4

Dose Response of in-clamshell Compound A application techniques to control growth of *Botrytis cinerea* inoculated in strawberries as compared to uninoculated strawberries.

| Inoculated Fruit | Gray Mold Incidence (%) | | | | | | |
|---|---|---|---|---|---|---|---|
| Rate (mg/clamshell) | Day 0 | Day 1 | Day 2 | Day 3 | Day 4 | Day 5 | Day 6 |
| 5 | 0.0 | 0.0 | 0.0 | 0.0 | 0.0 | 0.0 | 0.0 |
| 1 | 0.0 | 0.0 | 1.3 | 3.8 | 11.3 | 36.3 | 52.5 |
| Control | 6.3 | 72.5 | 100.0 | 100.0 | 100.0 | 100.0 | 100.0 |
| | Gray Mold Severity (0-4) | | | | | | |
| | Day 0 | Day 1 | Day 2 | Day 3 | Day 4 | Day 5 | Day 6 |
| 5 | 0.0 | 0.0 | 0.0 | 0.0 | 0.0 | 0.0 | 0.0 |
| 1 | 0.0 | 0.0 | 0.0 | 0.1 | 0.2 | 0.6 | 1.5 |
| Control | 0.0 | 0.7 | 1.4 | 2.7 | 3.6 | 3.8 | 4.0 |
| Uninoculated Fruit | Gray Mold Incidence (%) | | | | | | |
| Rate (mg/clamshell) | Day 0 | Day 1 | Day 2 | Day 3 | Day 4 | Day 5 | Day 6 |
| 5 | 0.5 | 0.5 | 0.9 | 3.3 | 16.2 | 31.9 | 78.5 |
| 1 | 0.0 | 1.9 | 21.6 | 89.5 | 100.0 | 100.0 | 100.0 |
| Control | 1.0 | 6.0 | 46.0 | 100.0 | 100.0 | 100.0 | 100.0 |
| | Gray Mold Severity (0-4) | | | | | | |
| | Day 0 | Day 1 | Day 2 | Day 3 | Day 4 | Day 5 | Day 6 |
| 5 | 0.1 | 0.1 | 0.3 | 0.5 | 1.0 | 1.4 | 3.5 |
| 1 | 0.0 | 0.5 | 1.8 | 3.6 | 4.0 | 4.0 | 4.0 |
| Control | 0.3 | 1.0 | 2.9 | 4.0 | 4.0 | 4.0 | 4.0 |

The outcome of this in vivo experiment is summarized in Table 4. Results demonstrate good in vivo antimicrobial activity of Compound A against *B. cinerea*, with a reduction in disease incidence and severity with both 5 mg/clamshell and 1 mg/clamshell concentrations applied by spraying. In particular, each concentration of treating clamshells showed inhibition of gray mold incidence and severity in strawberries as compared to control. On Days 1-6, the percentage of gray mold incidence increased from 6.3% to 100% in control inoculated fruits, while there was no growth in 5 mg/clamshell-treated inoculated fruits. Even the 1 mg/clamshell-treated inoculated fruits inhibited gray mold incidence to a 52.5% maximum.

In uninoculated fruit, the percentage of gray mold incidence increased from 0.5% to 78.5% in control fruits, and similarly, from 0% to 100% in 1 mg/clamshell-treated uninoculated fruits. However, the percentage of gray mold incidence only increased from 0.5% to 78.5% in 5 mg/clamshell-treated uninoculated fruits.

In addition, each concentration of active ingredient on treated clamshells showed significant inhibition of gray mold severity in inoculated strawberries as compared to control (see Table 4). More specifically, on Days 1-6, the degree of gray mold severity increased from 0.0 to 4.0 in control fruits as compared to 0 to 1.5 in 1 mg/clamshell- Example 5: Benzoxaborole Compound Treatment of Fruit Clamshells by Sublimation (In Vivo)

This in vivo assay was used to evaluate the ability of Compound A to volatilize from a clamshell in order to control or inhibit fruit infection by pathogenic microorganism, *Botrytis cinerea*. This experiment was conducted exactly as described in Example 1, with a few exceptions. After equilibrating the clamshell overnight at 21° C., Compound A was administered to the clamshell by sublimation only. Compound A was sublimed onto the surface of the clamshell at a final treatment rate of 5 mg/clamshell. Strawberries were inoculated with *Botrytis cinerea*, placed within the clamshell for an initial time period of 6 days, and assessed for disease incidence and severity over a second time period of 7 days as described in Example 1.

The outcome of this in vivo experiment is summarized in Table 5. Results demonstrate good in vivo antimicrobial activity of Compound A against *B. cinerea*, with a reduction in disease incidence and severity with the 5 mg/clamshell concentrations applied by sublimation. In particular, both inoculated and uninoculated 5 mg/clamshell-treated clamshells showed inhibition of gray mold incidence and severity in strawberries as compared to control. On Days 1-7, the percentage of gray mold incidence increased from 14.6% to 100% in control inoculated fruits, while there was a maximum of 18.8% of gray mold incidence in 5 mg/clamshell-treated inoculated fruits observed on Day 6.

In uninoculated fruit, the percentage of gray mold incidence increased from 0% to 100% in control fruits, however, the percentage of gray mold incidence only increased to 54.1% in 5 mg/clamshell-treated uninoculated fruits.

In addition, the 5 mg/clamshell concentration of active ingredient on sublimation-treated clamshells showed significant inhibition of gray mold severity in inoculated strawberries as compared to control (see Table 5). More specifically, on Days 1-7, the degree of gray mold severity increased from 0.1 to 4.0 in control inoculated fruits as compared to 0 to 0.3 in 5 mg/clamshell-treated inoculated fruits. For uninoculated fruits, the control fruits showed a gray mold severity level of 4.0 by Day 5, while the 5 mg/clamshell-treated uninoculated fruits only showed a gray mold severity level of 1.6 on Day 7. Ultimately, this data demonstrate that treating clamshells with 5 mg/clamshell of benzoxaborole Compound A inhibited the gray mold infection of *B. cinerea* inoculated in strawberries.

The outcome of this in vivo experiment is summarized in Table 6. Results demonstrate good in vivo antimicrobial activity of Compound A against *B. cinerea*, with a reduction in disease incidence and severity with the 5 mg/clamshell concentrations applied by painting. In particular, both inoculated and uninoculated 5 mg/clamshell-treated clamshells showed inhibition of gray mold incidence and severity in strawberries as compared to control. On Days 1-7, the percentage of gray mold incidence increased from 0% to 100% in control inoculated fruits, while there was a maximum of 18.8% of gray mold incidence in 5 mg/clamshell base-treated inoculated fruits observed on Day 7. However, inoculated fruits in clamshells painted with 5 mg of Compound A on the lids only or the base and lids showed no incidence of gray mold even by Day 7.

In uninoculated fruit, the percentage of gray mold incidence increased from 0% to 100% in control fruits, however, the percentage of gray mold incidence only increased to 41.1%, 64.4%, and 52.2% in uninoculated fruits painted with 5 mg/clamshell on the base only, the lid only, and the base and lid, respectively.

TABLE 5

Ability of Compound A applied to clamshells by sublimation to control growth of *Botrytis cinerea* inoculated in strawberries.

| Inoculated Fruit | Gray Mold Incidence (%) | | | | | | | |
|---|---|---|---|---|---|---|---|---|
| Treatment | Day 0 | Day 1 | Day 2 | Day 3 | Day 4 | Day 5 | Day 6 | Day 7 |
| 5 mg Compound A | 0.0 | 0.0 | 0.0 | 0.0 | 0.0 | 16.7 | 18.8 | 16.7 |
| Control | 14.6 | 52.1 | 91.7 | 95.8 | 97.9 | 100.0 | 100.0 | 100.0 |
| | Gray Mold Severity (0-4) | | | | | | | |
| Treatment | Day 0 | Day 1 | Day 2 | Day 3 | Day 4 | Day 5 | Day 6 | Day 7 |
| 5 mg Compound A | 0.0 | 0.0 | 0.0 | 0.0 | 0.0 | 0.1 | 0.2 | 0.3 |
| Control | 0.1 | 0.4 | 0.9 | 2.0 | 3.0 | 4.0 | 4.0 | 4.0 |
| Uninoculated Fruit | Gray Mold Incidence (%) | | | | | | | |
| Treatment | Day 0 | Day 1 | Day 2 | Day 3 | Day 4 | Day 5 | Day 6 | Day 7 |
| 5 mg Compound A | 0.0 | 2.6 | 0.1 | 26.3 | 34.1 | 40.0 | 43.3 | 54.1 |
| Control | 0.0 | 23.0 | 0.6 | 95.2 | 100.0 | 100.0 | 100.0 | 100.0 |
| | Gray Mold Severity (0-4) | | | | | | | |
| Treatment | Day 0 | Day 1 | Day 2 | Day 3 | Day 4 | Day 5 | Day 6 | Day 7 |
| 5 mg Compound A | 0.0 | 0.4 | 1.0 | 1.0 | 1.0 | 1.3 | 1.3 | 1.6 |
| Control | 0.1 | 1.0 | 1.0 | 2.0 | 2.8 | 4.0 | 4.0 | 4.0 |

Example 6: Benzoxaborole Compound Treatment to Different Locations of Fruit Clamshells by Painting (In Vivo)

This in vivo assay was used to evaluate the ability of Compound A to volatilize from different locations of a clamshell (i.e., the base and/or the lid of the clamshell) in order to control or inhibit fruit infection by pathogenic microorganism, *Botrytis cinerea*. This experiment was conducted exactly as described in Example 1, with a few exceptions. Compound A was administered to the clamshell by painting only. 5 mg of Compound A was painted onto the surface of the base of the clamshell or the lid of the clamshell (i.e., 5 mg/clamshell treatment rate). 2.5 mg of Compound A was painted onto the base and the lid of the clamshell (for a total of 5 mg/clamshell treatment rate). The clamshell was then permitted to dry for 5 minutes. Strawberries were inoculated with *Botrytis cinerea*, placed within the clamshell for an initial time period of 5 days, and assessed for disease incidence and severity over a second time period of 7 days as described in Example 1.

In addition, the 5 mg/clamshell concentration of active ingredient on painted clamshells showed significant inhibition of gray mold severity in inoculated strawberries as compared to control (see Table 6). More specifically, on Days 1-7, the degree of gray mold severity increased from 0 to 3.6 in control inoculated fruits as compared to 0 to 0.3 in 5 mg/clamshell base-treated inoculated fruits. However, inoculated fruits in clamshells painted with 5 mg of Compound A on the lids only or the base and lids showed no increase in the severity of gray mold even by Day 7.

For uninoculated fruits, the control fruits showed a gray mold severity level of 4.0 by Day 5, while the gray mold severity level was 1.5, 2.5, and 1.5 on Day 7 in uninoculated fruits painted with 5 mg/clamshell on the base only, the lid only, and the base and lid, respectively. Ultimately, these data demonstrate that treating clamshells with/clamshell of benzoxaborole Compound A significantly inhibited the gray mold infection of *B. cinerea* irrespective of the location of the treatment application.

TABLE 6

Ability of Compound A painted on the base, lid, or base and lid
of clamshells to control growth of *Botrytis cinerea* inoculated on strawberries.

Inoculated Fruit

Gray Mold Incidence (%)

| Treatment Location | Rate (mg) | Day 0 | Day 1 | Day 2 | Day 3 | Day 4 | Day 5 | Day 6 | Day 7 |
|---|---|---|---|---|---|---|---|---|---|
| Base | 5 | 0.0 | 0.0 | 12.5 | 12.5 | 0.0 | 0.0 | 18.8 | 18.8 |
| Lid | 5 | 0.0 | 0.0 | 0.0 | 0.0 | 0.0 | 0.0 | 0.0 | 0.0 |
| Base and Lid | 2.5/2.5 | 0.0 | 0.0 | 0.0 | 0.0 | 0.0 | 0.0 | 0.0 | 0.0 |
| Control | 0 | 0.0 | 25.0 | 56.3 | 68.8 | 93.8 | 93.8 | 93.8 | 100.0 |

Gray Mold Severity (0-4)

| Treatment Location | Rate (mg) | Day 0 | Day 1 | Day 2 | Day 3 | Day 4 | Day 5 | Day 6 | Day 7 |
|---|---|---|---|---|---|---|---|---|---|
| Base | 5 | 0.0 | 0.0 | 0.1 | 0.1 | 0.0 | 0.0 | 0.2 | 0.3 |
| Lid | 5 | 0.0 | 0.0 | 0.0 | 0.0 | 0.0 | 0.0 | 0.0 | 0.0 |
| Base and Lid | 2.5/2.5 | 0.0 | 0.0 | 0.0 | 0.0 | 0.0 | 0.0 | 0.0 | 0.0 |
| Control | 0 | 0.0 | 0.1 | 0.5 | 0.8 | 1.5 | 2.7 | 3.3 | 3.6 |

Uninoculated Fruit

Gray Mold Incidence (%)

| Treatment Location | Rate (mg) | Day 0 | Day 1 | Day 2 | Day 3 | Day 4 | Day 5 | Day 6 | Day 7 |
|---|---|---|---|---|---|---|---|---|---|
| Base | 5 | 0.0 | 0.0 | 0.0 | 0.0 | 2.2 | 10.0 | 26.7 | 41.1 |
| Lid | 5 | 0.0 | 0.0 | 0.0 | 1.1 | 18.9 | 27.8 | 45.6 | 64.4 |
| Base and Lid | 2.5/2.5 | 0.0 | 0.0 | 0.0 | 1.1 | 7.8 | 23.3 | 33.3 | 52.2 |
| Control | 0 | 0.0 | 1.1 | 1.1 | 18.9 | 88.9 | 97.8 | 100.0 | 100.0 |

Gray Mold Severity (0-4)

| Treatment Location | Rate (mg) | Day 0 | Day 1 | Day 2 | Day 3 | Day 4 | Day 5 | Day 6 | Day 7 |
|---|---|---|---|---|---|---|---|---|---|
| Base | 5 | 0.0 | 0.0 | 0.0 | 0.0 | 0.3 | 0.8 | 1.2 | 1.5 |
| Lid | 5 | 0.0 | 0.0 | 0.0 | 0.2 | 1.2 | 2.0 | 2.0 | 2.5 |
| Base and Lid | 2.5/2.5 | 0.0 | 0.0 | 0.0 | 0.2 | 0.8 | 1.5 | 1.5 | 1.5 |
| Control | 0 | 0.0 | 0.2 | 0.2 | 1.3 | 3.7 | 4.0 | 4.0 | 4.0 |

Example 7

For testing activity against fungi pathogens, an in vitro inhibition assay for volatile antimicrobial compounds is developed using 12-Well (7 milliliter (mL) volume per well) microtiter plates. A 3-mL volume of full-strength Potato Dextrose Agar (PDA) is added to each well. After cooling, 1 microliter (μL) of 1×10$^6$ per mL *Botrytis cinerea* spore suspension is spot pipetted to the center of the agar. For the first experiment, inoculated plates are allowed to germinate for 5 days at 4° C. For the second experiment, plates are inoculated immediately prior to volatile fungicide treatment. Small Whatman #1 filter disks (Cat. No. 1001-0155) are placed, in duplicate, on the underside of a polyethylene PCR plate sealing film.

TABLE 7

Results of in vitro assay for volatile fungicide

| Rate of Compound A (mg per disk) | *Botrytis* inhibition % (in vitro) |
|---|---|
| 1.25 | 100% |
| 0.63 | 100% |
| 0.31 | 100% |
| 0.16 | 100% |
| 0.08 | 100% |
| 0.04 | 100% |
| 0.023 | 100% |
| 0.01 | 100% |
| 0.005 | 100% |
| 0.0024 | 85% |
| 0.001 | 69% |

TABLE 7-continued

Results of in vitro assay for volatile fungicide

| Rate of Compound A (mg per disk) | *Botrytis* inhibition % (in vitro) |
|---|---|
| 0.0006 | 46% |
| Control | 0% |

For determination of the minimum inhibitory concentration (MIC), Compound A (5-fluoro-1,3-dihydro-1-hydroxy-2,1-benzoxaborole) is diluted in acetone, and the appropriate amount of compound is added to disks in a dose dependent manner (1.25 to 0.0006 milligrams per disk (mg/disk)). The acetone is permitted to evaporate for 5 minutes. The headspace around the *Botrytis cinerea* inoculum is then sealed inside the well by the film with the adhering disk containing the fungicide. Plates are inverted, placed over the treated disks and sealed to prevent any of the chemical from flaking from the disk and falling onto the inoculated agar. After 14 days of storage at 4° C., cultures are evaluated for percent growth relative to control. Regardless of whether the spores had germinated for 5 days, or if the treatment commenced soon after inoculation of the plates (~15 minutes); there is 100% control of the fungal pathogen down to 0.005 mg.

Experimental results are summarized in Table 1. The results suggest that Compound A is able to kill *Botrytis cinerea* spores and inhibit mycelial growth at the same concentration. Thus, Compound A shows 100% efficacy in the in vitro inhibition of fungal growth at a rate of 0.005 mg/disk.

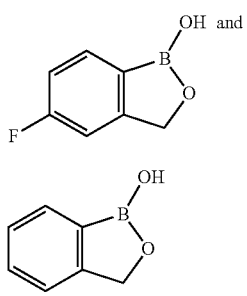

Compound A

Compound B2

Compound B2 (2-(hydroxymethyl)phenylboronic acid cyclic monoester, a des-fluoro analogue of Compound A), is evaluated in a similar manner. The compound is applied to the Whatman filter paper at rates from 0.5 mg to 0.0039 mg/disk. Results show that Compound B2 inhibits 100% *Botrytis cinerea* at a rate of 0.0078 mg/disk.

Example 8

For testing activity against bacteria pathogens, 12-Well (7 mL volume per well) microtiter plates are used for the in vitro inhibition assay for volatile antimicrobial compounds. A 3-mL volume of full-strength LB Agar is added to each well. After cooling, 15 µL of *Escherichia coli*, adjusted to an optical density of 0.02 to 0.035, and further diluted 1/10 is pipetted to the center of the agar and tilted to distribute uniformly. Small Whatman #1 filter disks (Cat. No. 1001-0155) are placed, in duplicate, on the underside of a polyethylene polymerase chain reaction (PCR) plate sealing film. For determination of the minimum inhibitory concentration (MIC), Compound A is diluted in acetone, and 5 mg of compound is added to the disks. The acetone is permitted to evaporate for 5 minutes. The headspace around the *Escherichia coli* inoculum is then sealed inside the well by the film with the adhering disk containing the fungicide. Plates are inverted, placed over the treated disks and sealed to prevent any of the chemical from flaking from the disk and falling onto the inoculated agar. After 3 days of storage at 4° C., cultures are transferred to 23° C. for an additional 2 days, and then evaluated for colony growth relative to control. Experimental results are summarized in Table 2. The results suggest that Compound A is able to inhibit *Escherichia coli*.

TABLE 8

Results of in vitro assay for volatile fungicide

| Rate of Compound A (mg per disk) | Colony Rating |
|---|---|
| 5.00 | 1 |
| Untreated | 3 |
| Not Inoculated | 0 |

Colony Rating:
0 = No colonies
1 = Micro colonies not connected
2 = Small colonies with some merging
3 = Large colonies merging together

Example 9

For testing activities against additional fungi pathogens, 12-Well (6.5 mL volume per well) microtiter plates are used for the in vitro inhibition assay for volatile antimicrobial compounds. A 3-mL volume of full-strength Potato Dextrose Agar (PDA) is added to each well. After cooling, 1 µL of $1\times10^5$ per mL *Botrytis cinerea, Penicillium expansum, Alternaria alternata, Monilinia fructicola* or *Glomerella cingulata* spore suspension is spot-pipetted to the center of the agar. Plates are inoculated immediately prior to volatile fungicide treatment. A Whatman #1 filter disk (Cat. No. 1001-0155) is placed, in duplicate, on the underside of a polyethylene PCR plate sealing film. For determination of the minimum inhibitory concentration (MIC), compounds are diluted in acetone, and the appropriate amount of compound is added to the disks in a dose dependent manner to achieve a final headspace concentration of 1142.9 to 0.6 mg/L. The acetone is permitted to evaporate for 5 minutes. The headspace around the inoculum is then sealed inside the well by the film with the adhering disk containing the fungicide by inverting the plates over the treated disks and sealing to prevent any of the chemical from flaking from the disk and falling onto the inoculated agar. After 3 days of storage at 23° C., the cultures are evaluated for percent growth relative to control based on measurement of fungal colony diameter. Experimental results are summarized in Table 3. The results indicate that benzoxaborole compounds have excellent in vitro activity against five selected fungal pathogens.

TABLE 9

MIC (mg/L, headspace concentration) of numerous benzoxaborole compounds applied as a volatile treatment against numerous fungal pathogens (Compound 10 is the same as Compound A, and Compound 11 is the same as Compound B2).

| Structure | Cmpd # | MIC (mg/L) | | | | |
|---|---|---|---|---|---|---|
| | | BOTRCI | PENIEX | ALTEAL | MONIFC | GLOMCI |
| (structure with O—CH3) | 6 | 2.2 | 17.9 | 4.5 | 8.9 | 17.9 |
| (structure with O—(CH2)3—O—CH3) | 7 | 2.2 | 17.9 | 8.9 | 8.9 | 71.4 |

TABLE 9-continued

MIC (mg/L, headspace concentration) of numerous benzoxaborole compounds applied as a volatile treatment against numerous fungal pathogens (Compound 10 is the same as Compound A, and Compound 11 is the same as Compound B2).

| Structure | Cmpd # | MIC (mg/L) | | | | |
|---|---|---|---|---|---|---|
| | | BOTRCI | PENIEX | ALTEAL | MONIFC | GLOMCI |
| (benzoxaborole-O-CH2CH2-O-CH3) | 8 | 2.2 | 35.7 | 8.9 | 4.5 | 71.4 |
| (benzoxaborole-O-CH(CH3)2) | 9 | 2.2 | 8.9 | 8.9 | 8.9 | 35.7 |
| (5-F-benzoxaborole-OH) | 10 | 2.2 | 2.2 | <0.6 | <0.6 | <0.6 |
| (benzoxaborole-OH) | 11 | 4.5 | 17.9 | 4.5 | 2.2 | 35.7 |
| (5-F-benzoxaborole-O-butyl) | 30 | 2.2 | 8.9 | 2.2 | 2.2 | n/a |
| (5-F-benzoxaborole-O-CH2CH2-NH2) | 34 | <0.6 | 2.2 | 2.2 | n/a | n/a |
| (6-F-benzoxaborole-OH) | 200 | 10.6 | 68.3 | 7.3 | 6.3 | n/a |
| (5-Cl-benzoxaborole-OH) | 201 | 3.8 | 29.5 | 16.1 | 8.5 | 9.3 |

BOTRCI = *Botrytis cinerea*
PENIEX = *Penicillium expansum*
ALTEAL = *Alternaria alternata*
MONIFC = *Monilinia fructicola*
GLOMCI = *Glomerella cingulata*

Example 10

12-Well (6.5 mL volume per well) microtiter plates are used for the in vitro inhibition assay for volatile antimicrobial compounds. A 3-mL volume of full-strength Potato Dextrose Agar (PDA) is added to each well. After cooling, 1 µL of $1\times10^5$ per mL *Botrytis cinerea* and *Penicillium expansum* spore suspension is spot-pipetted to the center of the agar. Plates are inoculated immediately prior to volatile fungicide treatment. A Whatman #1 filter disk (Cat. No. 1001-0155) is placed, in duplicate, on the underside of a polyethylene PCR plate sealing film. For determination of the minimum inhibitory concentration (MIC), compounds are diluted in acetone, and the appropriate amount of compound is added to the disks in a dose dependent manner to achieve a final headspace concentration of 35.7 to 0.03 mg/L. The acetone is permitted to evaporate for 5 minutes. The headspace around the inoculum is then sealed inside the well by the film with the adhering disk containing the fungicide by inverting the plates over the treated disks and sealing to prevent any of the chemical from flaking from the disk and falling onto the inoculated agar. After 3 days of storage at 23° C., the cultures are evaluated for percent growth relative to control based on measurement of fungal colony diameter. Experimental results are summarized in Table 10. The results indicate that numerous benzoxaborole compounds have excellent in vitro activity against two selected fungal pathogens.

TABLE 10

MIC (mg/L) of numerous benzoxaborole compounds applied as a volatile treatment against *Botrytis cinerea* and *Penicillium expansum* fungal pathogens.

| Structure | Cmpd # | MIC (mg/L) BOTRCI | PENIEX |
|---|---|---|---|
| 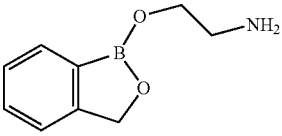 [SMILES: NCCOB1OCc2ccccc21] | 21 | 1.1 | 35.7 |
| 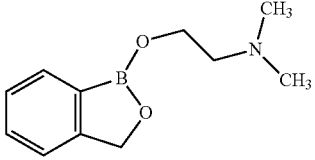 | 22 | 4.5 | 35.7 |
| 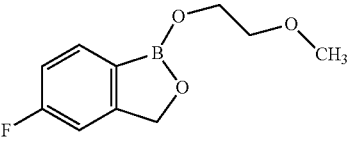 | 38 | 0.6 | 8.9 |
| 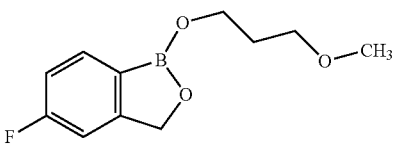 [SMILES: COCCCOB1OCc2cc(F)ccc21] | 39 | 0.6 | 8.9 |
| 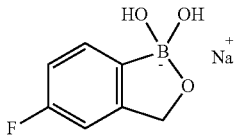 | 54 | 0.6 | 4.5 |
| 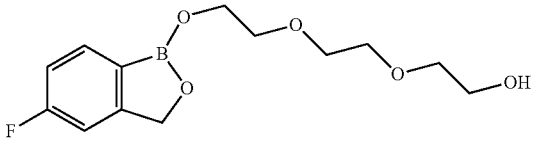 [SMILES: OCCOCCOCCOB1OCc2cc(F)ccc21] | 55 | 4.5 | >35.7 |
| 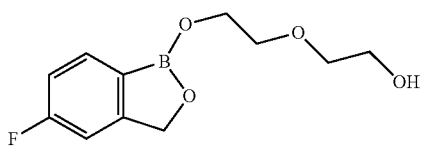 [SMILES: OCCOCCOB1OCc2cc(F)ccc21] | 62 | 2.2 | 8.9 |

TABLE 10-continued

MIC (mg/L) of numerous benzoxaborole compounds applied as a volatile treatment against *Botrytis cinerea* and *Penicillium expansum* fungal pathogens.

| Structure | Cmpd # | MIC (mg/L) BOTRCI | MIC (mg/L) PENIEX |
|---|---|---|---|
| (5-fluorobenzoxaborole-O-CH₂CH₂CH₂-N(CH₃)₂) | 63 | 1.1 | 17.9 |
| (5-fluorobenzoxaborole-O-CH₂CH₂CH₂-NH₂) | 64 | 1.1 | 8.9 |
| (5-fluorobenzoxaborole-O-CH₂CH₂-N(CH₃)CH₂CH₂OH) | 72 | 35.7 | >35.7 |
| (5-fluorobenzoxaborole-O-CH₂CH₂-NH-CH₂CH₂OH) | 73 | 35.7 | >35.7 |
| (5-fluorobenzoxaborole-O-CH₂CH₂-N(CH₃)₂) | 74 | 2.2 | 35.7 |
| (5-fluorobenzoxaborole-O-(CH₂)₅-OH) | 86 | 0.6 | 8.9 |
| (5-fluorobenzoxaborole-O-CH₂CH₂-NH-CH₃) | 87 | 0.6 | 8.9 |
| (5-fluorobenzoxaborole-OH with N(CH₃)₂H adduct) | 105 | 0.6 | 4.5 |

TABLE 10-continued

MIC (mg/L) of numerous benzoxaborole compounds applied as a volatile treatment against *Botrytis cinerea* and *Penicillium expansum* fungal pathogens.

| Structure | Cmpd # | MIC (mg/L) BOTRCI | MIC (mg/L) PENIEX |
|---|---|---|---|
| (structure) | 114 | 17.9 | >35.7 |
| (structure) | 115 | 0.6 | 8.9 |
| (structure) | 116 | 1.1 | 8.9 |
| (structure) | 121 | 4.5 | 17.9 |
| (structure) | 122 | 2.2 | 17.9 |
| (structure) | 124 | 4.5 | 8.9 |
| (structure) | 127 | 2.2 | 4.5 |

TABLE 10-continued

MIC (mg/L) of numerous benzoxaborole compounds applied as a volatile treatment against *Botrytis cinerea* and *Penicillium expansum* fungal pathogens.

| Structure | Cmpd # | MIC (mg/L) BOTRCI | MIC (mg/L) PENIEX |
|---|---|---|---|
| 5-fluoro-1-vinyl-benzoxaborole | 129 | 4.5 | 8.9 |
| 5-fluoro-1,1-dihydroxy-benzoxaborole potassium salt | 130 | 1.1 | 4.5 |
| 5-fluoro-1-hydroxy-1-cyano-benzoxaborole sodium salt | 132 | 1.1 | 4.5 |
| 5-fluoro-1-(4-fluorophenyl)-benzoxaborole | 133 | 8.9 | 35.7 |
| 5-fluoro-1-(3-fluorophenyl)-benzoxaborole | 134 | 17.9 | >35.7 |
| 5-fluoro-1-(4-methoxyphenyl)-benzoxaborole | 135 | 17.9 | >35.7 |
| 5-fluoro-1-(3-methoxyphenyl)-benzoxaborole | 136 | 8.9 | >35.7 |

TABLE 10-continued

MIC (mg/L) of numerous benzoxaborole compounds applied as a volatile treatment against *Botrytis cinerea* and *Penicillium expansum* fungal pathogens.

| Structure | Cmpd # | MIC (mg/L) BOTRCI | MIC (mg/L) PENIEX |
|---|---|---|---|
| (5-fluoro-1-(prop-1-en-2-yl)benzoxaborole structure) | 137 | 0.3 | 1.1 |
| (4-fluoro-1-hydroxybenzoxaborole structure) | 202 | 35.7 | 142.9 |
| (7-fluoro-1-hydroxybenzoxaborole structure) | 203 | 8.9 | 142.9 |
| (5,6-difluoro-1-hydroxybenzoxaborole structure) | 204 | 8.9 | >35.7 |

BOTRCI = *Botrytis cinerea* (gray mold)
PENIEX = *Penicillium expansum* (blue mold)

Example 11

12-Well (6.5 mL volume per well) microtiter plates are used for the in vitro inhibition assay for volatile antimicrobial compounds A and B2 against additional fungal pathogens.

A 3-mL volume of full-strength Potato Dextrose Agar (PDA) is added to each well. After cooling, 1 μL of 1×10$^5$ spores per mL of *Botrytis cinerea*, *Penicillium expansum*, *Alternaria alternata*, *Glomerella cingulata*, *Penicillium digitatum*, *Monilinia fruticola*, *Aspergillus brasiliensis*, *Colletotrichum acutatum*, *Fusarium sambucinum*, *Phytophthora capsici*, *Geotrichum candidum*, *Aspergillus niger*, *Diplodia gossypina* or *Diaporthe citrii* suspension is spotted onto the center of the agar. A Whatman #1 filter disk (Cat. No. 1001-0155) is placed, in duplicate, on the underside of a polyethylene PCR plate sealing film. For determination of the minimum inhibitory concentration (MIC), test compounds are diluted in acetone, and the appropriate amount of compound is added to the disks in a dose dependent manner to achieve a final headspace concentration of 35.7 to 0.03 mg/L. The acetone is permitted to evaporate for five minutes. The headspace around the inoculum is then sealed inside the well by the film with the adhering disk containing the fungicide by inverting the plates over the treated disks and sealing to prevent any of the chemical from flaking from the disk and falling onto the inoculated agar. After 3 days of storage at 23° C., cultures are evaluated for percent growth relative to control. Results shown in Table 11 demonstrate the ability of benzoxaborole compounds A and B2 to control the growth of numerous fungal pathogens through volatile activity.

TABLE 11

MIC (mg/L) of Compounds A and B applied as a volatile against numerous fungal pathogens

| Pathogens | Compound A MIC | Compound B2 MIC |
|---|---|---|
| B. cinerea | 2.2 | 4.5 |
| P. expansum | 1.1 | 8.9 |
| M. fruticola | 2.2 | 1.1 |
| A. alternata | 2.2 | 2.2 |
| G. cingulata | 17.9 | 35.7 |
| P. digitatum | 2.2 | 4.5 |
| A. brasiliensis | 2.2 | 0.6 |
| C. acutatum | 4.4 | 8.9 |
| F. sambucinum | 1.1 | 4.5 |
| P. capsici | 1.1 | n/a |
| G. candidum | 8.9 | 8.9 |
| A. niger | 2.2 | 1.1 |
| M. piriformis | 1.1 | 2.2 |
| D. gossypina | 1.1 | 4.5 |
| D. citrii | 2.2 | 17.9 |

Example 12

12-Well (6.5 mL volume per well) microtiter plates are used for the in vitro inhibition assay for volatile antimicrobial Compound A against additional bacterial pathogens. A 3-mL volume of Nutrient agar is added to each well and allowed to dry before introducing the pathogen. *Escherichia coli, Pectobacterium carotovorum, Xanthomonas axonopodis* and *Salmonella enterica* cell suspensions are adjusted to an optical density of 0.2 to 0.35, and further diluted 1/10, and 15 µL is pipetted to the center of each well and tilted to distribute uniformly. A Whatman #1 filter paper (CAT 1001-0155) is placed on the underside of a polyethylene PCR plate sealing film. For determination of minimum bactericidal concentration (MBC), Compound A is diluted in acetone, and 50 µL are applied to the disks, in duplicate, in a dose dependent manner in order to achieve a final headspace concentration of 71.4 to 0.03 mg/L. The acetone is permitted to evaporate for 5 minutes. The films with the treated disks are then applied over the inoculated plates and sealed. Plates are inverted, and incubated at 23° C. for 48 hours. After the incubation period, the bacteria colonies are dislodged in sterile water containing tween 80 (0.001%) and the optical density (OD; 600 nm) is determined. Results are summarized in Table 6, where the headspace concentration required to control at least 80% of bacterial growth is reported. Compound A shows good antimicrobial activity against numerous bacteria in this in vitro assay.

TABLE 12

Rate (mg/L) of Compound A offering at least 80% control against bacterial pathogens

| E. coli | P. carotovorum | X. axonopodis | S. enterica |
|---|---|---|---|
| 35.7 | 2.2 | 4.5 | 17.9 |

Example 13

An in vitro assay is used to evaluate the ability of Compound A to volatilize from different materials and control fungal growth. PTFE-Coated Fiberglass (8577K81), Fiberglass (8816K1), Silica (8799K3), Aramid and Fiberglass blend (8821K4), Vinyl-Coated Polyester (8843K31), Acrylic-Coated Fiberglass (8838K2), Silicone-Coated Fiberglass (87815K1), Aramid (1206T1) (all McMaster-Carr, Santa Fe Springs, CA), Polyethylene PCR sealing film, Cellulose (Whatman #1, Cat no. 1001-0155), PTFE (Cole Parmer, Cat no. 36229-32), and Category-1 cardboard were cut into disks of 15 mm diameter. 12-Well (6.5 mL volume per well) microtiter plates are used for the in vitro inhibition assay for volatile antimicrobial compounds. A 3-mL volume of full-strength Potato Dextrose Agar (PDA) is added to each well. After cooling, 1 µL of 1×10⁵ per mL *Botrytis cinerea* spore suspension is spot-pipetted to the centre of the agar. Plates are inoculated immediately prior to volatile fungicide treatment.

TABLE 13

Effects of different materials on the volatile release of Compound A and the subsequent in vitro inhibition (MIC) of *Botrytis cinerea*.

| Material | MIC (mg/L) |
|---|---|
| Polyethylene PCR Film | 0.28 |
| PTFE—Coated Fiberglass | 0.56 |
| Fiberglass | 0.56 |
| Cellulose | 0.56 |
| Silica | 0.56 |
| Aramid and Fiberglass | 0.56 |
| Vinyl—Coated Polyester | 0.56 |
| Acrylic—Coated Fiberglass | 0.56 |
| Silicone—Coated Fiberglass | 0.56 |
| PTFE | 1.1 |
| Cardboard | 2.2 |
| Aramid | 2.2 |

The various materials are placed, in duplicate, on the underside of a polyethylene PCR plate sealing film. For determination of the minimum inhibitory concentration (MIC), compounds are diluted in acetone, and the appropriate amount of compound is added to the materials in a dose dependent manner to achieve a final headspace concentration of 35.7 to 0.03 mg/L. The acetone is permitted to evaporate for five minutes. The headspace around the *Botrytis cinerea* inoculum is then sealed inside the well by the film with the adhering disk of material containing the fungicide. Plates are inverted, placed over the treated disks and sealed to prevent any of the chemical from flaking from the disk and falling onto the inoculated agar. After three days of storage at 23° C., the cultures are evaluated for percent growth relative to control based on measurement of fungal colony diameter. Experimental results are summarized in Table 7. The results indicate that Compound A can volatilize from numerous materials to inhibit the in vitro growth of *Botrytis cinerea* with similar levels of control.

Example 14

An in vitro assay is used to evaluate the ability of compound A to volatilize from different materials and control fungal growth. Cardboard box (Category 1), PET plastic (Polyethylene terepthalate—PET) and Polyethylene are used. The materials are cut into equal dimensions (10×19 cm²) and placed inside a 36-L acrylic desiccator cabinet (Fisher Scientific, cat no. 08-642-23C) in duplicate.

TABLE 14

Effects of different materials on the volatile release of Compound A and the subsequent in vitro inhibition of *Botrytis cinerea*

| Material | Incidence (%) | | |
|---|---|---|---|
| Rate (mg/L) | Clamshell | Cardboard | Polyethylene |
| 0.3 | 4.1 | 9.3 | 4.9 |
| 0.06 | 100.0 | 91.7 | 86.7 |
| 0.012 | 100.0 | 100.0 | 99.0 |

Compound A is dissolved in acetone and 100 µL of the solution pipetted into a glass tube. The acetone is allowed to evaporate for 1 minute at 60° C. Compound A is then introduced as a gas into the cabinets by a sublimation device (copper tube heated to 180° C. with fan flow at 0.5 L/min) to achieve a final headspace concentration of 0.3, 0.06 and 0.012 mg/L). The chambers are then incubated at 23° C. for 24 hours, then treated materials are carefully removed and placed inside a clean 10.8 cup SnapWare airtight container (Model #109842) containing a 10-cm diameter Petri dish with PDA and inoculated with 1 µL of 1×10 spores/mL of *B. cinerea*. The containers are then tightly sealed for 3 days at 23° C. After 3 days of storage, cultures are evaluated for percent growth relative to control. Table 14 demonstrates the ability of benzoxaborole compounds A to control the growth of *B. cinerea* through volatile activity.

Example 15

3.20 g of 5-fluoro-1,3-dihydro-1-hydroxy-2,1-benzoxaborole (21.2 mmol) and 3.20 g of ethylene glycol (51.6 mmol) are heated in 40 g of toluene. The toluene water azeotrope is distilled out of the system until the head temperature reached 110° C. The toluene is removed via rotary evaporator and the excess ethylene glycol is removed by kugelrohr distillation at about 20 torr and 100° C. bath temperature. Recrystallization from toluene generates 2.95 g of white crystals, mp 145-149° C. Proton nmr shows spectra and integration consistent with the two to one product below:

Example 16

Preparation of Sample 2

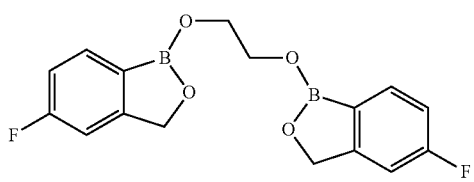 [SMILES: Fc1ccc2c(c1)COB2OCCOB1OCc2cc(F)ccc21]

3.00 g of 1,3-dihydro-1-hydroxy-2,1-benzoxaborole (22.4 mmol) and 3.00 g of ethylene glycol (46.9 mmol) are heated in 40 g of toluene. The toluene water azeotrope is distilled out of the system until the head temperature reached 110° C. The toluene is removed via rotary evaporator and the excess ethylene glycol is removed by kugelrohr distillation at about 20 torr and 100° C. bath temperature. Recrystallization from toluene generates 2.49 g of white crystals, mp 118-120.5° C. Proton NMR shows spectra and integration consistent with the two to one product.

Example 17

Preparation of Sample 3

3.17 g of 5-fluoro-1,3-dihydro-1-hydroxy-2,1-benzoxaborole (21.0 mmol) and 3.22 g of pinacol (27.3 mmol) are heated in 40 g of toluene. The toluene water azeotrope is distilled out of the system until the head temperature reached 110° C. The toluene is removed via rotary evaporator and the excess pinacol is removed by kugelrohr distillation at about 20 torr and 120° C. bath temperature. Recrystallization from hexane generates 3.21 g of white crystals, mp 81-89° C. Proton NMR shows spectra and integration consistent with the two to one product.

Example 18

Preparation of Sample 4

3.0 g of 5-fluoro-1,3-dihydro-1-hydroxy-2,1-benzoxaborole (19.9 mmol) and 2.5 g of 1,2-propanediol (propylene glycol; 32.9 mmol) are heated in 40 g of toluene. The toluene water azeotrope is distilled out of the system until the head temperature reached 110° C. The toluene is removed via rotary evaporator and the excess propylene glycol is removed by kugelrohr distillation at about 20 torr and 110° C. bath temperature. Recrystallization from hexane generates 3.49 g of white crystals, mp 65.5-68.5° C. Proton NMR shows spectra and integration consistent with the two to one product.

Example 19

In Vitro Analysis 12-well (6.5 ml volume per well) microtiter plates are used for the in vitro inhibition assay for volatile antimicrobial compounds. A 3-ml volume of full-strength Potato Dextrose Agar (PDA) is added to each well. After cooling, 1 μL of 1×10$^5$ spores per ml *Botrytis cinerea* (ATCC #204446) spore suspension is spot pipetted to the agar in the centre of the well.

TABLE 15

Antimicrobial activities of Samples 1-4 (50 μl/disk)

| | MIC mg/l | | | | |
|---|---|---|---|---|---|
| ID | Botrytis cinerea | Penicillium expansum | Alternaria alternata | Monilinia fructicola | Glomerella cingulata |
| Sample 1 | <0.6 | 8.9 | 22 | — | — |
| Sample 2 | <0.6 | 8.9 | 8.9 | 35.7 | 142.9 |
| Sample 3 | <0.6 | 4.5 | 2.2 | — | — |
| Sample 4 | <0.6 | 8.9 | 1.1 | — | — |

Whatman #1 filter disks (1.5 cm; Cat. No. 1001-0155) are placed on the underside of a polyethylene PCR plate sealing film. For determination of the minimum inhibitory concentration (MIC), test compounds are diluted in acetone, in duplicate, and 50 μl of the compound solution is added to disks at concentrations that can vary from 0.001 mg/l to 1142.9 mg/l.

TABLE 16

Antimicrobial activities of Samples 1-4 (repeat test; 50 μl/disk)

| | MIC mg/l | | | | |
|---|---|---|---|---|---|
| ID | Botrytis cinerea | Penicillium expansum | Alternaria alternata | Monilinia fructicola | Glomerella cingulata |
| Sample 1 | 0.6 | 8.9 | >2.2 | 2.2 | — |
| Sample 2 | 2.2 | 8.9 | — | — | — |
| Sample 3 | 1.1 | 8.9 | >2.2 | 1.1 | — |
| Sample 4 | 0.6 | 8.9 | >2.2 | 1.1 | — |

The acetone is permitted to evaporate for 5 minutes. The headspace around the *Botrytis cinerea* inoculum is then sealed inside the well by the film with the adhering disk containing the fungicide. Plates are inverted to prevent any possibility of the chemical from flaking from the disk and falling onto the inoculated agar. After 3 days of incubation at 23° C., cultures are evaluated for percent growth relative to control and determination of MIC. Samples 1-4 show good antimicrobial activity against *Botrytis cinerea* and/or other pathogens in this in vitro analysis. Minimum inhibitory concentrations (MIC) are shown in Tables 9 and 10 for results from two separate tests.

Example 20

Antimicrobial Activity Against Bacteria 12-well (6.5 ml volume per well) microtiter plates are used for the in vitro inhibition assay for volatile antimicrobial compounds. A 3-ml volume of full-strength LB Agar is added to each well. After cooling, 15 µL of *Escherichia coli* (ATCC #25922) adjusted to an optical density of 0.02 to 0.035, and further diluted 1/10 is pipetted to the centre of the agar. The plate is tilted to distribute bacteria uniformly. Whatman #1 filter disks (1.5 cm; Cat. No. 1001-0155) are placed on the underside of a polyethylene PCR plate sealing film. For determination of the minimum inhibitory concentration (MIC), test compounds are diluted in acetone, in duplicate, and 50 µl of compound is added to disks at concentrations that can vary from 0.015 to 35.7 mg/l. The acetone is permitted to evaporate for 5 minutes. The headspace around the *Escherichia coli* inoculum is then sealed inside the well by the film with the adhering disk containing the fungicide. Plates are inverted, placed over the treated disks and sealed to prevent any of the chemical from flaking from the disk and falling onto the inoculated agar. After 2 days of incubation at 23° C., cultures were evaluated for colony growth relative to control. Samples 1-4 show good antimicrobial activity against *Escherichia coli* in this in vitro analysis.

Example 21

In order to demonstrate unexpected volatility of compound A (1-hydroxy-5-fluoro-1, 3-dihydro-2, 1-benzoxaborole) and a new method to apply the volatile compound A, another in vivo assay is developed to control *Botrytis cinerea* on strawberry. Eight strawberries (per repetition, in triplicate) are placed in an industry standard 1-lb PET clamshell with the stem-end facing down. A fresh wound on the upwards facing tip of the fruit is then inoculated with 20 µL of 1×10⁵ spores per mL suspension of *B. cinerea*.

Two identically prepared clamshells per repetition and treatment are then placed at the bottom of a 36-L acrylic desiccator cabinet (Fisher Scientific, No. 08-642-23C), and pre-cooled for 2 hours at 1° C. prior to treatment application. Compound A is then mixed with acetone and 100 µL of the mixture is pipetted into a small glass tube. This tube is then placed inside a pre-heated sublimation device (0.5" OD by 6" long thermostatically heated copper tube mounted to a 0.5 L/min low flow fan) set at 60° C. for 1-minute to allow the acetone to evaporate. Compound A is then introduced into the cabinet containing the clamshell by using the sublimation device set at 180° C. to achieve a final headspace concentration of 0.1 mg/L and equilibrated at 1° C. for 0.5 or 1 hour.

TABLE 17

Valatile application of Compound A to control *B. cinerea* infection

| Clamshell Condition | Treatment Time (hour) | Disease Severity (0 to 4) | | |
|---|---|---|---|---|
| | | Day 1 | Day 3 | Day 5 |
| Untreated | 0 | 1.3 | 3.5 | 4.0 |
| Treated | 0.5 | 0.0 | 0.1 | 2.3 |
| | 1 | 0.0 | 0.0 | 0.4 |
| Untreated (fruit transfer) | 0.5 | 0.0 | 2.7 | 3.4 |
| | 1 | 0.0 | 0.1 | 1.6 |

After incubation, both clamshells are removed from the treatment chamber. One clamshell is undisturbed while the fruit from the second clamshell are immediately transferred into a new untreated clamshell. All clamshells are then held at 1° C. for 5 days and then evaluated during an additional 5 days at 21° C. During the 5 days at 21° C., the fruits are evaluated for gray mold severity (scale 0 to 4, with ≤1 indicating marketable fruit and 4 indicating ≥50% of fruit surface covered by pathogen). The results from Table 11 demonstrate the unexpected volatility of Compound A applied to clamshells and its ability to control *B. cinerea* development on strawberry throughout the 5 days of simulated marketing at 21° C. The treated clamshell produces marketable fruit up to 3 days with 0.5 hour treatment (0.1), whereas fruits in new clamshells are unmarketable (2.7). Similarly, the treated clamshell produces marketable fruit up to 5 days with 1 hour treatment (0.4), whereas fruits in new clamshells are unmarketable (1.6). Thus, treatments where berries remain in the treated clamshells have the best level of control due to the compound further volatilizing over time off of the clamshell surface.

Furthermore, berries that are placed into a new clamshell still benefit from the initial volatile treatment and demonstrated better control of *Botrytis cinerea* than untreated fruit, but the control is less than the treated clamshell since there is no longer any new exposure to the volatile substance off of the treated clamshell surface. Therefore, the results from this study provide evidence that a volatile application of Compound A provides control of fungal pathogen growth (untreated fruit transfer) and that Compound A deposited on clamshell surfaces will subsequently volatilize during 5 days at 21° C., providing additional useful control of *Botrytis cinerea* growth (treated).

Example 21

In order to demonstrate unexpected volatility of Compound A, another in vivo assay is developed to evaluate blue mold (*Penicillium expansum*) control on apple. Two apples are placed in a clamshell, and three fresh wounds are made near the equatorial region of each fruit. Each fruit wound is then inoculated with 20 µL of 1×10⁶ spores per mL of *Penicillium expansum* suspension. The inoculum is allowed to dry for two hours prior to treatment application as a volatile or contact.

TABLE 18

Comparison of volatile and contact fungicidal activity of Compound A to control *Penicillim expansum* infection

| Assay | Treatment rate (mg/L) | Browning Rot (diameter; mm) | | | |
|---|---|---|---|---|---|
| | | Day 0 | Day 2 | Day 4 | Day 7 |
| Contact | 0 | 0.0 | 6.4 | 15.7 | 29.6 |
| | 2 | 0.0 | 3.7 | 15.5 | 23.3 |
| | 10 | 0.0 | 2.2 | 8.0 | 20.2 |
| | 50 | 0.0 | 0.7 | 5.7 | 15.0 |
| | 250 | 0.0 | 0.0 | 4.3 | 11.8 |
| Volatile | 0 | 0.0 | 6.6 | 16.1 | 30.5 |
| | 0.02 | 0.0 | 0.9 | 2.8 | 6.9 |
| | 0.1 | 0.0 | 0.0 | 0.3 | 2.0 |
| | 0.5 | 0.0 | 0.0 | 0.0 | 0.4 |
| | 2.5 | 0.0 | 0.0 | 0.0 | 0.0 |

Volatile Assay: Clamshells are then placed at the bottom of a 36-L acrylic desiccator cabinet (Fisher Scientific, No. 08-642-23C). Compound A is mixed with acetone and 250 µL of the mixture is pipetted into a small glass tube. This tube is then placed inside a pre-heated sublimation device (0.5" OD by 6" long thermostatically heated copper tube mounted to a 0.5 L/min low flow fan) set at 60° C. for 1 minute to allow the acetone to evaporate. Compound A is then introduced into the cabinets containing the clamshells by using the sublimation device set at 180° C. to achieve a final headspace concentration of 2.5, 0.5, 0.1 or 0.02 mg/L.

The chambers are then incubated at 1° C. for 5 days. After incubation, fruits are evaluated by measuring the diameter (mm) of rot development (browning) up to 7 days at 21° C.

Contact Assay: Compound A is dissolved in 85% methanol to achieve a final concentration of 250, 50, 10, or 2 mg/L. A 250 mL solution of each concentration is used to dip two inoculated apples, one minute per apple, performed in triplicate per rate. The dipped fruits are then placed back into the clamshells, which are then placed in a secondary container and incubated at 1° C. for 5 days. After incubation, fruits are evaluated for diameter (mm) of rot development (browning) up to 7 days at 21° C. Table 12 demonstrates the unexpected volatility of Compound A to control *Penicillium expansum* on apples during storage even when applied at 100× lower rate (v/v) than as a contact.

Example 23

In order to demonstrate unexpected volatility of Compound A, another in vivo assay is developed to evaluate gray mold (*Botrytis cinerea*) control on strawberry. Eight strawberries (per repetition, in triplicate) are placed in an industry standard 1-lb PET clamshell with the stem-end facing down. A fresh wound on the upwards facing tip of the fruit is then inoculated with 20 µL of 1×10$^5$ spores per mL suspension of *B. cinerea*. The inoculum is allowed to dry for two hours prior to treatment application as a volatile or contact.

TABLE 19

Comparison of volatile and contact fungicidal activity of Compound A to control *Botrytis cinerea* infection

| Assay | Treatment rate (mg/L) | Disease Severity (0 to 4) | | | | |
|---|---|---|---|---|---|---|
| | | Day 0 | Day 1 | Day 2 | Day 3 | Day 4 |
| Contact | 0 | 0.0 | 0.0 | 0.8 | 1.1 | 2.0 |
| | 2 | 0.0 | 0.0 | 0.6 | 1.1 | 1.9 |
| | 10 | 0.0 | 0.0 | 0.0 | 0.3 | 1.0 |
| | 50 | 0.0 | 0.0 | 0.0 | 0.0 | 0.0 |
| | 250 | 0.0 | 0.0 | 0.0 | 0.0 | 0.0 |
| Volatile | 0 | 0.0 | 0.1 | 0.9 | 1.4 | 2.3 |
| | 0.02 | 0.0 | 0.0 | 0.1 | 0.2 | 0.7 |
| | 0.1 | 0.0 | 0.0 | 0.0 | 0.0 | 0.0 |
| | 0.5 | 0.0 | 0.0 | 0.0 | 0.0 | 0.0 |
| | 2.5 | 0.0 | 0.0 | 0.0 | 0.0 | 0.0 |

Volatile Assay: Clamshells are then placed at the bottom of a 36-L acrylic desiccator cabinet (Fisher Scientific, No. 08-642-23C). Compound A is mixed acetone and 250 µL of the mixture is pipetted into a small glass tube. This tube is then placed inside a pre-heated sublimation device (0.5" OD by 6" long thermostatically heated copper tube mounted to a 0.5 L/min low flow fan) set at 60° C. for 1-minute to allow the acetone to evaporate. Compound A is then introduced into the cabinets containing the clamshells by using the sublimation device set at 180° C. to achieve a final headspace concentration of 2.5, 0.5, 0.1 or 0.02 mg/L. The chambers are then incubated at 1° C. for 5 days. After incubation, fruits are evaluated for disease (scale 0 to 4, with ≤1 indicating marketable fruit and 4 indicating ≥50% of fruit surface covered by pathogen) up to 4 days at 21° C.

Contact Assay: Compound A is dissolved in 85% methanol to achieve a final concentration of 250, 50, 10, or 2 mg/L. A 250 mL solution of each concentration is used to dip eight inoculated strawberry fruit for one-minute, performed in triplicate per rate. The dipped fruits are then placed back into the clamshells, which are then placed in a secondary container and incubated at 1° C. for 5 days. After incubation, fruits are evaluated for disease severity (scale 0 to 4, with ≤1 indicating marketable fruit and 4 indicating ≥50% of fruit surface covered by pathogen) up to 4 days at 21° C. Table 19 demonstrates the unexpected volatility of Compound A to control *Botrytis cinerea* on strawberries during storage even when applied at 100× lower rate (v/v) than as a contact.

Example 24

An in vitro assay was performed comparing the volatile and contact activity of various benzoxaborole compounds to demonstrate the activity of compound 10 relative to other similar structures from the chemical class.

Volatile assay: 12-well (6.5 mL volume per well) microtiter plates are used. A 3-mL volume of half strength PDA is added to each well. After cooling, 1 µL of 1×10$^5$ spores per mL of *Botrytis cinerea* or *Penicillium expansum* suspension is spotted to the center of the agar. A Whatman #1 filter disk (Cat. No. 1001-0155) is placed, in duplicate, on the underside of a polyethylene PCR plate sealing film. Test compounds are mixed with acetone and the mixtures are added to disks in a dose dependent manner to achieve a final headspace concentration of 35.7 to 0.03 mg/L. The acetone is permitted to evaporate for 5 minutes. The headspace around the inoculum is then sealed inside the well by the film with the adhering disk containing the fungicide. Plates are inverted, placed over the treated disks, and sealed to prevent any of the chemical from flaking from the disk and falling onto the inoculated agar. After 3 days of incubation at 23° C., cultures are evaluated for percent growth relative to the acetone only control.

TABLE 20

Comparison of contact and volatile activity of selected benzoxaborole compounds

| Compound | Contact MIC (mg/L) | | Volatile MIC (mg/L) | |
|---|---|---|---|---|
| ID | *B. cinerea* | *P. expansum* | *B. cinerea* | *P. expansum* |
| 6 | 2.0 | 2.0 | 4.5 | 17.9 |
| 10* | <0.08 | 0.4 | 0.3 | 2.2 |
| 11* | 10 | 2.0 | 4.5 | 17.9 |
| 31 | 0.4 | 2.0 | 0.6 | 8.9 |
| 33 | 0.4 | 2.0 | 0.6 | 8.9 |
| 34 | 2.0 | 0.4 | 0.6 | 2.2 |
| 121 | 10.0 | 10.0 | 4.5 | 17.9 |
| 124 | 2.0 | 2.0 | 4.5 | 8.9 |
| 130 | 2.0 | 0.4 | 1.1 | 4.5 |
| 132 | 2.0 | 2.0 | 1.1 | 4.5 |
| 135 | 2.0 | 2.0 | 17.9 | >35.7 |

*Compound 10 is identical to Compound A; Compound 11 is identical to Compound B2

Contact assay: 6-well (16.5 mL volume per well) microtiter plates are used for an in vitro inhibition assay. Half-strength Potato Dextrose Agar (PDA) is amended with a mixture of one of the test compounds with acetone or methanol to a final concentration of 50 to 0.08 mg/L. A 7.5-mL volume of the amended media is added to each well of the microtiter plate. After drying, 1 µL of 1×10$^5$ spores per mL of *B. cinerea* or *P. expansum* suspension is spotted to the center of the agar. The plates are sealed with a clear film and incubated for 3 days at 23° C. After incubation, plates are evaluate for percent growth relative to acetone only control. Results are reported as the minimum inhibitory concentration (MIC) required for 100% control of pathogen growth. Table 20 shows the MIC results of numerous benzoxaboroles assayed for both contact and volatile activity.

Results demonstrate that numerous structures in the benzoxaborole class of compounds have both contact and volatile activity.

TABLE 21

Compounds used in this example

| Compound ID | Benzoxaborole structure |
|---|---|
| 6 | |
| 10* | |
| 11* | |
| 31 | |
| 33 | |
| 34 | |
| 121 | |
| 124 | |
| 130 | |
| 132 | |
| 135 | |

*Compound 10 is identical to Compound A;
Compound 11 is identical to Compound B2
Compound 33 is identical to Compound B Example 25

In order to demonstrate unexpected volatility of Compound A, another in vivo assay is developed to evaluate blue mold (*Penicillium expansum*) control on apple and pear, as well as green mold (*Penicillium digitatum*) control on orange. Two apples, pears or oranges are placed in a clamshell, and three fresh wounds are made near the equatorial region of each fruit. Each fruit wound is then inoculated with 20 µL of 1×10$^6$ spores per mL of *Penicillium expansum* or *digitatum* suspension, respectively. The inoculum is allowed to dry for two hours prior to treatment application as a volatile or contact.

TABLE 22

Comparison of Compound A with other fungicides in volatile and contact assays

| | | Apple | | Pear | | Orange |
|---|---|---|---|---|---|---|
| Assay | Test Compound | Browning (mm) | Sporulation (mm) | Browning (mm) | Sporulation (mm) | Sporulation (mm) |
| Volatile | Control (acetone only) | 11.1 | 2.2 | 14.9 | 4.0 | 44.9 |
| | Compound A | 0.4 | 0.0 | 5.7 | 0.0 | 0.0 |
| | Control (ethanol only) | 9.7 | 2.3 | 13.4 | 4.4 | 39.3 |
| | Boscalid | 10.3 | 2.4 | 14.3 | 3.6 | 30.3 |

TABLE 22-continued

Comparison of Compound A with other fungicides in volatile and contact assays

| Assay | Test Compound | Apple Browning (mm) | Apple Sporulation (mm) | Pear Browning (mm) | Pear Sporulation (mm) | Orange Sporulation (mm) |
|---|---|---|---|---|---|---|
| | Fludioxonil | 11.2 | 3.1 | 12.8 | 2.8 | 40.8 |
| | Imazalil | 11.1 | 3.0 | 14.3 | 3.4 | 41.4 |
| | Pyrimethanil | 11.3 | 2.6 | 14.0 | 6.5 | 22.3 |
| | Thiabendazole | 8.4 | 2.0 | 12.9 | 3.0 | >50 |
| Contact | Control (5% PG only) | 10.3 | 2.6 | 15.1 | 5.4 | >50 |
| | Compound A | 9.9 | 2.3 | 18.9 | 8.4 | >50 |
| | Control (ethanol only) | 9.2 | 5.1 | 8.9 | 1.9 | 9.7 |
| | Boscalid | 7.0 | 0.8 | 8.6 | 2.3 | >50 |
| | Fludioxonil | 2.9 | 0.0 | 3.3 | 0.0 | 8.3 |
| | Imazalil | 6.9 | 0.9 | 7.9 | 1.0 | 0.0 |
| | Pyrimethanil | 8.1 | 2.4 | 8.9 | 5.2 | 0.0 |
| | Thiabendazole | 8.2 | 1.9 | 9.1 | 5.4 | 0.0 |

Volatile Assay: Clamshells are then placed at the bottom of a 2.55-L SnapWare airtight container (Model #109842). An appropriate amount of Compound A (dissolved in acetone), Boscalid, Fludioxinil, Imazalil, Pyrimethanil or Thiabendazole (methanol) is solubilized to achieve a treatment rate of 50 mg/L. (Compound A is not soluble in methanol at room temperature). The solutions are pipetted into Whatman filter disks mounted to the inside lid of the container. The chambers are then incubated at 1° C. for 5 days, removed to 21° C., and evaluated on day 3 by determining the diameter (mm) of rot development (browning) or sporulation.

Contact Assay: Compound A is dissolved in 5% propylene glycol, whereas all other actives are dissolved in 85% methanol at a rate to achieve a final concentration of 250, 50, 10, or 2 mg/L (Compound A is not soluble in methanol at room temperature). A 250 mL solution of each concentration is used to dip two inoculated fruits, one minute per fruit, performed in triplicate per rate. The dipped fruits are then placed back into the clamshells and then into the SnapWare container and incubated at 1° C. for 5 days. The containers are then incubated at 1° C. for 5 days, removed to 21° C., and evaluated on day 3 by determining the diameter (mm) of rot development (browning) or sporulation. Table 21 demonstrates the unexpected volatility of Compound A to control *Penicillium expansum* on apples and pears, as well as *Penicillium digitatum* on oranges. Volatile application of Compound A results in excellent inhibition of browning and sporulation, whereas all other active ingredients result in no or little inhibition. However, contact application of Compound A does not provide good inhibition of browning and sporulation as compared to other fungicides, demonstrating that the volatile application is important for the fungicidal activity of Compound A.

Example 26

In order to demonstrate the volatile activity of Compound A and Compound 31 relative to commercially registered fungicides, an in vitro assay is performed comparing the volatile and contact activity of the active ingredients.

Contact Assay: 12-well (6.5 mL volume per well) microtiter plates are used for the in vitro inhibition assay for Compounds A and 31, and compared to other registered fungicides (5-fluorocytosine, Amphotericin B, Caspofungin diacetate, Fluconazole and Itraconazole). Half-strength Potato Dextrose Agar (PDA) is amended with a mixture of one of the test compounds in acetone or methanol to a final concentration of 50, 10, 2, 0.4 or 0.08 mg/L. A 3-mL volume of the amended media is added to each well of the microtiter plate. After drying, a mycelial plug (5 mm diameter) is aseptically obtained from actively growing cultures of *Epidermophyton floccus*, *Trichophyton rubrum*, or *Trichophyton mentagrophytes* and placed at the center of the plate with the mycelial side in contact with the agar. The plates are sealed with a clear film and incubated inverted for 5 days at 28° C. After incubation, cultures are evaluated (mm diameter growth) for percent growth relative to control with results expressed as minimum inhibitory concentration (MIC) required to control 100% of pathogen growth.

TABLE 23

Comparison of Compounds A and 31 together with other fungicide to control selected fungal pathogens

| Assay | Test Compound | MIC (mg/L) Epidermophyton floccus | MIC (mg/L) Trichophyton rubrum | MIC (mg/L) Trichophyton mentagrophytes |
|---|---|---|---|---|
| Contact | Compound A | 2.0 | 2.0 | 2.0 |
| | Compound 31 | n.d. | 10.0 | 2.0 |
| | 5-Fluorocytosine | >50 | >50 | >50 |
| | Amphotericin B | 50.0 | >50 | >50 |
| | Caspofungin Diacetate | 2.0 | 10.0 | 50.0 |
| | Fluconazole | 10.0 | 50.0 | >50 |
| | Itraconazole | >50 | >50 | >50 |
| Volatile | Compound A | 2.0 | 2.0 | 2.0 |
| | Compound 31 | n.d. | 2.0 | 2.0 |
| | 5-Fluorocytosine | >50 | >50 | >50 |
| | Amphotericin B | >50 | >50 | >50 |
| | Caspofungin Diacetate | >50 | >50 | >50 |
| | Fluconazole | >50 | >50 | >50 |
| | Itraconazole | >50 | >50 | >50 | n.d. = not determined.

Volatile assay: 6-well (16.5 mL volume per well) microtiter plates are used in an in vitro inhibition assay for Compounds A and 31, and compared to other registered fungicides (5-fluorocytosine, Amphotericin B, aspofungin diacetate, Fluconazole and Itraconazole). A 7.5-mL volume of half strength PDA is added to each well. After drying, a mycelial plug (5 mm diameter) is aseptically obtained from actively growing cultures of *Epidermophyton floccus, Trichophyton rubrum*, or *Trichophyton mentagrophytes* and placed at the center of the plate with the mycelial side in contact with the agar. A Whatman #1 filter disk (Cat. No. 1001-325) is placed, in duplicate, on the underside of a polyethylene PCR plate sealing film. For determination of unexpected volatility, test compounds are mixed with acetone or methanol, and then added to disks in a dose dependent manner to achieve a final headspace concentration of 50, 10, 2, 0.4 or 0.08 mg/L. The acetone/methanol is permitted to evaporate for 5 minutes. The headspace around the inoculum is then sealed inside the well by the film with the adhering disk containing the fungicide and incubated inverted for 5 days at 28° C. After incubation, cultures are evaluated for percent growth relative to control with results expressed as minimum inhibitory concentration (MIC) required to control 100% of pathogen growth.

Volatile application of benzoxaboroles of Compounds A and 31 show significant fungicidal activities. Table 23 demonstrates the unexpected volatile activity of Compounds A and 31 with a minimum inhibitory concentration (MIC) of 2 mg/L for both Compound A and 31. In comparison, none of the commercial fungicide standards demonstrated any significant volatile activity where little or no fungicidal activity after volatile applications.

Example 27

In order to demonstrate the volatile activity of Compound 10 (i.e., Compound A) on fungal pathogen species causing human yeast infection, an in vitro assay to measure the rate of growth inhibition was performed. More specifically, growth inhibition of yeast infection fungal species *C. albicans* and *C. krusei* (or *I. orientalis*) by volatile treatment of Compound 10 was assessed via a volatile assay.

Volatile assay: 6-well (16.5 mL volume per well) microtiter plates are used in an in vitro inhibition assay for Compound 10 (i.e., Compound A). A 7.5-mL volume of half strength PDA is added to each well. After drying, a mycelial plug (5 mm diameter) is aseptically obtained from actively growing cultures of *C. albicans* and *C. krusei* (or *I. orientalis*) and placed at the center of the plate with the mycelial side in contact with the agar. A Whatman #1 filter disk (Cat. No. 1001-325) is placed, in duplicate, on the underside of a polyethylene PCR plate sealing film. For determination of unexpected volatility, test Compound 10 is mixed with acetone or methanol, and then added to disks in a dose dependent manner to achieve a final headspace concentration of 35.7, 17.9, 8.9, 4.5, 2.2, 1.1, 0.6, 0.3, 0.1, 0.07, 0.035, and 0.017 mg/L (see Table 24). The acetone/methanol is permitted to evaporate for 5 minutes. The headspace around the inoculum is then sealed inside the well by the film with the adhering disk containing the fungicide and incubated inverted for 5 days at 28° C. After incubation, cultures are evaluated for percent growth relative to control with results expressed as minimum inhibitory concentration (MIC) required to control 100% of pathogen growth.

TABLE 24

MIC (mg/L) of Compound 10 (i.e., Compound A) applied as a volatile against *Candida albicans* and *Issatchenkia orientalis*

| | Growth Inhibition (%) | |
| --- | --- | --- |
| MIC mg/L | *C. albicans* | *C. krusei/I. orientalis* |
| 35.7 | 100.0 | 100.0 |
| 17.9 | 100.0 | 30.0 |
| 8.9 | 100.0 | 30.5 |
| 4.5 | 100.0 | 22.0 |
| 2.2 | 100.0 | 18.2 |
| 1.1 | 40.2 | −0.2 |
| 0.6 | 22.2 | −5.2 |
| 0.3 | 18.5 | 1.2 |
| 0.1 | 11.9 | 0.4 |
| 0.07 | 7.9 | 0.5 |
| 0.035 | 1.6 | −1.4 |
| 0.017 | 2.0 | −1.3 |

Volatile application of benzoxaboroles of Compound 10 (i.e., Compound A) shows significant fungicidal activities against yeast infection pathogens, *C. albicans* and *C. krusei*. For example, Table 24 demonstrates the unexpected volatile activity of Compound 10 (i.e., Compound A) with a minimum inhibitory concentration (MIC) of 2.2 mg/L for *C. albicans* and a minimum inhibitory concentration (MIC) of 35.7 mg/L for *C. krusei*.

Example 28

An in vivo assay is used to evaluate the ability of Compound A (1-hydroxy-5-fluoro-1, 3-dihydro-2, 1-benzoxaborole) to control fungal growth of seeds.

TABLE 25

Effect of a 10 mg/L headspace treatment of Compound A in controlling *Aspergillus brasiliensis* growth on grains.

| | Fungal growth on PDA (mm) | | |
| --- | --- | --- | --- |
| Grains | Compound A | Control—Acetone | Control—No Acetone |
| Barley | 0 | 12.8 | 21.7 |
| Corn Dry | 0 | 10.1 | 22.8 |
| Millet | 0 | 7.2 | 19.1 |
| Rice | 0 | 7.5 | 21.6 |
| Rye | 0 | 8.4 | 21 |
| Wheat | 0 | 8.1 | 22.4 |

Grains consisting of corn, wheat, rice, rye, millet and barley are surface sterilized with 0.825% NaOCl for 1 minute and rinsed thrice with sterile distilled water. The grains are inoculated by soaking them in a $1\times10^6$ spores/mL suspension of *Aspergillus brasiliensis* for 1 minute. The excess inoculum is blotted out with a sterile paper towel before plating five seeds in a Petri plate containing 25 mL of PDA. For determination of efficacy, Compound A is diluted in acetone and added to 42.5 mm Whatman #1 filter disks (Cat. No. 1001-042) attached to the inner side of the lid in a dose dependent manner to achieve a final headspace concentration of 0.4, 2, or 10 mg/L. The acetone is permitted to evaporate for five minutes before closing plate and sealing it with parafilm. The plates are incubated at 23° C. for three days. After storage, the grains are evaluated for mycelial colony diameter (mm), with results summarized in Table 25. Results demonstrate 100% control of *Aspergillus brasiliensis* in this in vivo analysis.

The preceding description enables others skilled in the art to utilize the technology in various embodiments and with various modifications as are suited to the particular use contemplated. In accordance with the provisions of the patent statutes, the principles and modes of operation of this disclosure have been explained and illustrated in exemplary embodiments. Accordingly, the present invention is not limited to the particular embodiments described and/or exemplified herein.

It is intended that the scope of disclosure of the present technology be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

The scope of this disclosure should be determined, not only with reference to the above description, but should instead be determined with reference to the appended claims, along with the full scope of equivalents to which such claims are entitled. It is anticipated and intended that future developments will occur in the arts discussed herein, and that the disclosed compositions and methods will be incorporated into such future examples.

Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the disclosure and that the technology within the scope of these claims and their equivalents be covered thereby. In sum, it should be understood that the disclosure is capable of modification and variation and is limited only by the following claims.

What is claimed is:

1. A method of treating a food packaging material with an antimicrobial agent, the method comprising:
   administering a benzoxaborole treatment to one or more surfaces of the food packaging material, wherein the benzoxaborole treatment comprises one or more benzoxaborole compounds,
   drying the one or more surfaces of the food packaging material,
   placing a food product inside of the food packaging material,
   wherein the one or more benzoxaborole compounds are:
   i) of formula (IV), or a salt thereof:

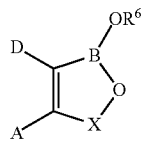

(IV)

wherein A and D together with the carbon atoms to which they are attached form a 5-, 6-, or 7-membered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings;

X is a group —$CR^7R^8$ wherein $R^7$ and $R^8$ are each independently hydrogen, $C_1$-$C_6$-alkyl, nitrile, nitro, aryl, arylalkyl or $R^7$ and $R^8$ together with the carbon atom to which they are attached form an alicyclic ring; and $R^6$ is hydrogen, $C_1$-$C_{18}$-alkyl, $C_1$-$C_{18}$-alkyl substituted by $C_1$-$C_6$-alkoxy, $C_1$-$C_6$-alkylthio, hydroxy, amino, amino substituted by $C_1$-$C_{18}$-alkyl, carboxy, aryl, aryloxy, carbonamido, carbonamido substituted by $C_1$-$C_6$-alkyl, aryl or arylalkyl, arylalkyl, aryl, heteroaryl, cycloalkyl, $C_1$-$C_{18}$-alkyleneamino, $C_1$-$C_{18}$-alkyleneamino substituted by phenyl, $C_1$-$C_6$-alkoxy or $C_1$-$C_6$-alkylthio, carbonyl alkyleneamino or a radical of formula (V):

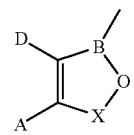

(V)

wherein A, D and X are as defined herein before, or ii) formula (A):

$$R^A\text{-}L^A\text{-}G\text{-}L^B\text{-}R^B \quad (A),$$

wherein
each of $R^A$ and $R^B$ is independently a of $R^A$ and $R^B$ is of formula (E):

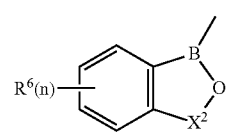

(E)

wherein each $R^6$ is independently hydrogen, alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, halogen, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

n=1, 2, 3, or 4;

B is boron;

$X^2$=$(CR^6_2)_m$ where m=1 or 2;

each of $L^A$ and $L^B$ is independently —O— or

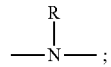

each of R and R' is independently hydrogen, unsubstituted or substituted $C_{1-18}$-alkyl, arylalkyl, aryl, or heterocyclic moiety; and G is a substituted or unsubstituted $C_{1-18}$-alkylene, arylalkylene, arylene, or heterocyclic moiety; and acceptable salts thereof.

2. The method of claim 1, wherein the food product is selected from the group consisting of a strawberry, a raspberry, a blackberry, and a blueberry.

3. The method of claim 1, wherein the benzoxaborole is of formula (IV), or a salt thereof:

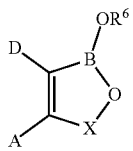

(IV)

wherein A and D together with the carbon atoms to which they are attached form a 5-, 6-, or 7-membered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings;

X is a group —$CR^7R^8$ wherein $R^7$ and $R^8$ are each independently hydrogen, $C_1$-$C_6$-alkyl, nitrile, nitro, aryl, arylalkyl or $R^7$ and $R^8$ together with the carbon atom to which they are attached form an alicyclic ring; and $R^6$ is hydrogen, $C_1$-$C_{18}$-alkyl, $C_1$-$C_{18}$-alkyl substituted by $C_1$-$C_6$-alkoxy, $C_1$-$C_6$-alkylthio, hydroxy, amino, amino substituted by $C_1$-$C_{18}$-alkyl, carboxy, aryl, aryloxy, carbonamido, carbonamido substituted by $C_1$-$C_6$-alkyl, aryl or arylalkyl, arylalkyl, aryl, heteroaryl, cycloalkyl, $C_1$-$C_{18}$-alkyleneamino, $C_1$-$C_{18}$-alkyleneamino substituted by phenyl, $C_1$-$C_6$-alkoxy or $C_1$-$C_6$-alkylthio, carbonyl alkyleneamino or a radical of formula (V):

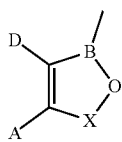

(V)

wherein A, D and X are as defined herein before.

4. The method of claim 3, wherein the benzoxaborole compound is has the structure

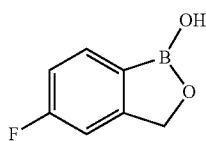

or a salt thereof.

5. The method of claim 1, wherein the benzoxaborole has the structure formula (A):

$R^A$-$L^A$-G-$L^B$-$R^B$   (A), wherein
each of $R^A$ and $R^B$ is independently a of $R^A$ and $R^B$ is of formula (E):

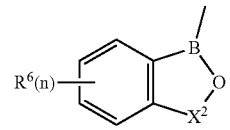

(E)

wherein each $R^6$ is independently hydrogen, alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, halogen, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

n=1, 2, 3, or 4;
B is boron;
$X^2$=$(CR^6{}_2)_m$ where m=1 or 2;
each of $L^A$ and $L^B$ is independently —O— or

each of R and R' is independently hydrogen, unsubstituted or substituted $C_{1-18}$-alkyl, arylalkyl, aryl, or heterocyclic moiety; and
G is a substituted or unsubstituted $C_{1-18}$-alkylene, arylalkylene, arylene, or heterocyclic moiety; and acceptable salts thereof.

6. The method of claim 3, wherein the benzoxaborole has the structure

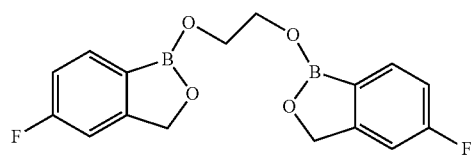 [SMILES: Fc1ccc2c(c1)COB2OCCOB1OCc2cc(F)ccc21]

or a salt thereof.

7. The method of claim 1, wherein administering the benzoxaborole treatment to food packaging material comprises embedding the benzoxaborole compound into the food packaging material, impregnating the food packaging material with the benzoxaborole compound, or coating the food packaging material with the benzoxaborole compound.

8. The method of claim 1, wherein the food packaging material is a chamber.

9. The method of claim 8, wherein the chamber is a clamshell.

10. The method of claim 9, wherein the clamshell comprises polyethylene terephthalate.

11. A large-scale method of treating a plurality of chambers with an antimicrobial agent, the method comprising:
placing a plurality of chambers in a position to be treated wherein each of the chambers comprise one or more surfaces,
administering the antimicrobial treatment to one or more surfaces of the plurality of chambers during preformation, formation, or postformation of the plurality of chambers, wherein the antimicrobial treatment comprises one or more benzoxaborole compounds,
drying the one or more surfaces of the plurality of chambers, and affixing the benzoxaborole compound to the one or more surfaces of the plurality of chambers, wherein the one or more benzoxaborole compounds are:
i) of formula (IV), or a salt thereof:

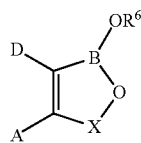

(IV)

wherein A and D together with the carbon atoms to which they are attached form a 5-, 6-, or 7-membered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings;
X is a group —$CR^7R^8$ wherein $R^7$ and $R^8$ are each independently hydrogen, $C_1$-$C_6$-alkyl, nitrile, nitro, aryl, arylalkyl or $R^7$ and $R^8$ together with the carbon atom to which they are attached form an alicyclic ring; and
$R^6$ is hydrogen, $C_1$-$C_{18}$-alkyl, $C_1$-$C_{18}$-alkyl substituted by $C_1$-$C_6$-alkoxy, $C_1$-$C_6$-alkylthio, hydroxy, amino, amino substituted by $C_1$-$C_{18}$-alkyl, carboxy, aryl, aryloxy, carbonamido, carbonamido substituted by $C_1$-$C_6$-alkyl, aryl or arylalkyl, arylalkyl, aryl, heteroaryl, cycloalkyl, $C_1$-$C_{18}$-alkyleneamino, $C_1$-$C_{18}$-alkyleneamino substituted by phenyl, $C_1$-$C_6$-alkoxy or $C_1$-$C_6$-alkylthio, carbonyl alkyleneamino or a radical of formula (V):

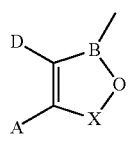

(V)

wherein A, D and X are as defined herein before, or
ii) formula (A):

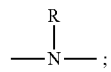

(A), wherein
each of $R^A$ and $R^B$ is independently a of $R^A$ and $R^B$ is of formula (E):

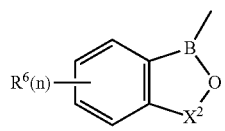

(E)

wherein each $R^6$ is independently hydrogen, alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, halogen, hydroxyl, nitrile, amine,
ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;
n=1, 2, 3, or 4;
B is boron;
$X^2$=$(CR^6{}_2)_m$ where m=1 or 2;
each of $L^A$ and $L^B$ is independently —O— or $$-\underset{\underset{\mid}{N}}{\overset{R}{\mid}}-;$$

each of R and R' is independently hydrogen, unsubstituted or substituted $C_{1-18}$-alkyl, arylalkyl, aryl, or heterocyclic moiety; and
G is a substituted or unsubstituted $C_{1-18}$-alkylene, arylalkylene, arylene, or heterocyclic moiety; and acceptable salts thereof.
12. The method of claim 11, wherein the benzoxaborole is of formula (IV), or a salt thereof:

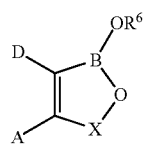

(IV)

wherein A and D together with the carbon atoms to which they are attached form a 5-, 6-, or 7-membered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings;
X is a group —$CR^7R^8$ wherein $R^7$ and $R^8$ are each independently hydrogen, $C_1$-$C_6$-alkyl, nitrile, nitro, aryl, arylalkyl or $R^7$ and $R^8$ together with the carbon atom to which they are attached form an alicyclic ring; and
$R^6$ is hydrogen, $C_1$-$C_{18}$-alkyl, $C_1$-$C_{18}$-alkyl substituted by $C_1$-$C_6$-alkoxy, $C_1$-$C_6$-alkylthio, hydroxy, amino, amino substituted by $C_1$-$C_{18}$-alkyl, carboxy, aryl, aryloxy, carbonamido, carbonamido substituted by $C_1$-$C_6$-alkyl, aryl or arylalkyl, arylalkyl, aryl, heteroaryl, cycloalkyl, $C_1$-$C_{18}$-alkyleneamino, $C_1$-$C_{18}$-alkyleneamino substituted by phenyl, $C_1$-$C_6$-alkoxy or $C_1$-$C_6$-alkylthio, carbonyl alkyleneamino or a radical of formula (V):

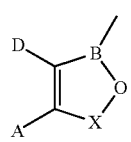

(V)

wherein A, D and X are as defined herein before.
13. The method of claim 12, wherein the benzoxaborole compound is has the structure

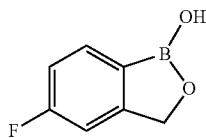

or a salt thereof.

14. The method of claim 11, wherein the benzoxaborole has the structure formula (A):

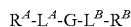

$R^A$-$L^A$-G-$L^B$-$R^B$ (A), wherein each of $R^A$ and $R^B$ is independently a of $R^A$ and $R^B$ is of formula (E):

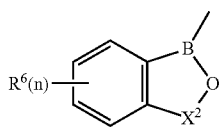

wherein each $R^6$ is independently hydrogen, alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, halogen, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

n=1, 2, 3, or 4;

B is boron;

$X^2$=$(CR^6_2)_m$ where m=1, 2, 3, or 4;

each of $L^A$ and $L^B$ is independently —O— or

each of R and R' is independently hydrogen, unsubstituted or substituted $C_{1-18}$-alkyl, arylalkyl, aryl, or heterocyclic moiety; and G is a substituted or unsubstituted $C_{1-18}$-alkylene, arylalkylene, arylene, or heterocyclic moiety; and acceptable salts thereof.

15. The method of claim 14, wherein the benzoxaborole has the structure

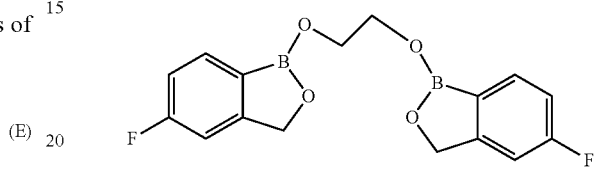

or a salt thereof.

16. The method of claim 11, wherein administering the benzoxaborole treatment to the one or more surfaces of the plurality of chambers during preformation, formation, or postformation of the plurality of chambers further comprises embedding the benzoxaborole compound into the food packaging material, impregnating the food packaging material with the benzoxaborole compound, or coating the food packaging material with the benzoxaborole compound.

17. The method of claim 11, wherein the one or more surfaces of the plurality of chambers further comprise a liquid-absorbing material.

18. The method of claim 17, wherein the liquid-absorbing material provides for quick-release or slow-release of the benzoxaborole treatment over a time period.

19. The method of claim 11, wherein the plurality of chambers are a plurality of clamshells.

20. The method of claim 19, wherein the plurality of clamshells comprise polyethylene terephthalate.

* * * * *